US012649883B2

(12) United States Patent
Trapp et al.

(10) Patent No.: US 12,649,883 B2
(45) Date of Patent: ***Jun. 9, 2026

(54) GASIFICATION OF DENSIFIED TEXTILES AND SOLID FOSSIL FUELS TO PRODUCE ORGANIC COMPOUNDS

(71) Applicant: Eastman Chemical Company, Kingsport, TN (US)

(72) Inventors: William Lewis Trapp, Kingsport, TN (US); Justin William Murphy, Kingsport, TN (US); Nathan Mitchell West, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 1200 days.

This patent is subject to a terminal disclaimer.

(21) Appl. No.: 17/593,628

(22) PCT Filed: Mar. 26, 2020

(86) PCT No.: PCT/US2020/024851
§ 371 (c)(1),
(2) Date: Sep. 22, 2021

(87) PCT Pub. No.: WO2020/205403
PCT Pub. Date: Oct. 8, 2020

(65) Prior Publication Data
US 2022/0177790 A1 Jun. 9, 2022

Related U.S. Application Data

(60) Provisional application No. 62/906,832, filed on Sep. 27, 2019, provisional application No. 62/825,880, filed on Mar. 29, 2019.

(51) Int. Cl.
*C10J 3/46* (2006.01)
*C07C 29/151* (2006.01)
(Continued)

(52) U.S. Cl.
CPC ........... *C10J 3/466* (2013.01); *C07C 29/1518* (2013.01); *C10J 3/84* (2013.01); *C10K 1/101* (2013.01);
(Continued)

(58) Field of Classification Search
None
See application file for complete search history.

(56) References Cited

U.S. PATENT DOCUMENTS 3,817,725 A 6/1974 Sieg et al.
3,841,851 A 10/1974 Kaiser
(Continued)

FOREIGN PATENT DOCUMENTS

CA 2 937 445 A1 1/2018
CN 1102605 C 3/2003
(Continued)

OTHER PUBLICATIONS

Co-pending U.S. Appl. No. 17/310,649, filed Aug. 16, 2021; Trapp et al.
(Continued)

*Primary Examiner* — Joseph D Anthony
(74) *Attorney, Agent, or Firm* — Steven A. Owen; Dennis V. Carmen

(57) ABSTRACT

Densified textile aggregates are co-fed with a fuel into a partial oxidation gasifier. High solids concentrations in the feedstock composition can be obtained without significant impact on the feedstock composition stability and pumpability. A consistent quality of syngas can be continuously produced, including generation of carbon dioxide and a carbon monoxide/hydrogen ratio while stably operating the gasifier and avoiding the high tar generation of fluidized bed or fixed bed waste gasifiers and without impacting the operations of the gasifier. The syngas quality, composition,
(Continued)

and throughput are suitable for produce a wide range of chemicals.

12 Claims, 5 Drawing Sheets

(51) Int. Cl.
  *C10J 3/84* (2006.01)
  *C10K 1/10* (2006.01)

(52) U.S. Cl.
  CPC .................. *C10J 2300/0906* (2013.01); *C10J 2300/0916* (2013.01); *C10J 2300/093* (2013.01); *C10J 2300/0946* (2013.01); *C10J 2300/0959* (2013.01); *C10J 2300/1656* (2013.01); *C10J 2300/1665* (2013.01)

(56) References Cited

U.S. PATENT DOCUMENTS

| | | | |
|---|---|---|---|
| 3,909,364 | A | 9/1975 | Singh |
| 4,052,173 | A | 10/1977 | Schulz |
| 4,152,119 | A | 5/1979 | Schulz |
| 4,225,457 | A | 9/1980 | Schulz |
| 4,886,000 | A | 12/1989 | Hölter et al. |
| 5,323,714 | A | 6/1994 | Cox |
| 5,656,042 | A | 8/1997 | Khan et al. |
| 5,821,111 | A | 10/1998 | Grady et al. |
| 5,922,090 | A | 7/1999 | Fujimura et al. |
| 5,984,985 | A | 11/1999 | Malone |
| 6,063,355 | A | 5/2000 | Fujimura et al. |
| 6,321,666 | B1 | 11/2001 | Tigonen |
| 6,401,635 | B1 | 6/2002 | Nieminen et al. |
| 6,439,135 | B1 | 8/2002 | Pope |
| 7,425,315 | B2 | 9/2008 | Kruesi |
| 7,500,997 | B2 | 3/2009 | Norbeck et al. |
| 8,083,818 | B2 | 12/2011 | Ploeg et al. |
| 8,118,894 | B2 | 2/2012 | Norbeck et al. |
| 8,202,913 | B2 | 6/2012 | Robinson et al. |
| 8,246,700 | B1 | 8/2012 | Kutsin |
| 8,303,676 | B1 | 11/2012 | Weaver et al. |
| 8,349,034 | B2 | 1/2013 | Calabrese et al. |
| 8,349,039 | B2 | 1/2013 | Robinson |
| 8,361,428 | B2 | 1/2013 | Raman et al. |
| 8,580,152 | B2 | 11/2013 | Sutradhar et al. |
| 8,585,789 | B2 | 11/2013 | Sutradhar et al. |
| 8,617,424 | B2 | 12/2013 | Badhe et al. |
| 8,697,924 | B2 * | 4/2014 | Bauldreay ............... C10G 3/49 585/242 |
| 8,722,958 | B2 | 5/2014 | Kashimoto |
| 8,734,547 | B2 | 5/2014 | Rappas et al. |
| 8,759,596 | B2 | 6/2014 | Yie et al. |
| 8,828,105 | B2 | 9/2014 | Calabrese et al. |
| 8,863,518 | B2 | 10/2014 | Koseoglu |
| 8,915,199 | B2 | 12/2014 | Bohlig et al. |
| 8,916,661 | B2 | 12/2014 | Bradin |
| 8,957,275 | B2 | 2/2015 | Stein et al. |
| 8,999,021 | B2 | 4/2015 | Sutradhar et al. |
| 9,023,124 | B2 | 5/2015 | Weaver et al. |
| 9,034,061 | B2 | 5/2015 | Robinson et al. |
| 9,133,405 | B2 | 9/2015 | Abughazaleh |
| 9,139,785 | B2 | 9/2015 | Tsantrizos |
| 9,200,207 | B2 | 12/2015 | Huang et al. |
| 9,416,077 | B2 | 8/2016 | Kelfkens et al. |
| 9,698,439 | B2 | 7/2017 | Weaver et al. |
| 9,702,552 | B2 | 7/2017 | Ali et al. |
| 9,834,728 | B2 | 12/2017 | Fleckner et al. |
| 9,982,205 | B2 | 5/2018 | Pichach |
| 10,329,501 | B2 | 6/2019 | Bai et al. |
| 11,939,406 | B2 * | 3/2024 | Trapp ..................... C08J 11/12 |
| 12,398,328 | B2 * | 8/2025 | DeBruin ................. C08J 11/24 |
| 2001/0006036 | A1 | 7/2001 | Kleiss |
| 2002/0113228 | A1 | 8/2002 | Kim et al. |
| 2004/0031424 | A1 | 2/2004 | Pope |
| 2004/0103831 | A1 | 6/2004 | Pope |
| 2004/0244289 | A1 | 12/2004 | Morozumi et al. |
| 2005/0000162 | A1 | 1/2005 | Bishop et al. |
| 2006/0219139 | A1 | 10/2006 | Pope et al. |
| 2007/0045455 | A1 | 3/2007 | Tuzson et al. |
| 2007/0204512 | A1 | 9/2007 | Self et al. |
| 2008/0245076 | A1 * | 10/2008 | Martin .................. F01K 23/067 241/38 |
| 2009/0094892 | A1 * | 4/2009 | Norbeck ................. C10L 9/086 48/210 |
| 2009/0217587 | A1 | 9/2009 | Raman et al. |
| 2009/0217588 | A1 | 9/2009 | Hippo et al. |
| 2010/0038325 | A1 | 2/2010 | Benson et al. |
| 2010/0042557 | A1 | 2/2010 | Block et al. |
| 2010/0076233 | A1 * | 3/2010 | Cortright ............... C10G 45/08 585/331 |
| 2010/0139534 | A1 | 6/2010 | Tsantrizos |
| 2010/0186291 | A1 | 7/2010 | Yie et al. |
| 2011/0036014 | A1 | 2/2011 | Tsangaris et al. |
| 2011/0185624 | A1 | 8/2011 | Hall |
| 2011/0245543 | A1 * | 10/2011 | Cortright ................. C10G 3/46 585/318 |
| 2011/0318515 | A1 | 12/2011 | Dubois et al. |
| 2012/0032452 | A1 | 2/2012 | Kuku |
| 2012/0266793 | A1 | 10/2012 | Bohlig et al. |
| 2013/0082210 | A1 | 4/2013 | Gautam et al. |
| 2013/0144087 | A1 * | 6/2013 | Arora ..................... B01J 23/626 252/373 |
| 2013/0269252 | A1 | 10/2013 | Tsangaris et al. |
| 2014/0290593 | A1 | 10/2014 | Krammer |
| 2015/0096222 | A1 | 4/2015 | Calabrese et al. |
| 2015/0133700 | A1 * | 5/2015 | Wollrab ............... C07C 29/149 568/884 |
| 2015/0141605 | A1 * | 5/2015 | Bradin ...................... C07C 1/22 585/329 |
| 2015/0211736 | A1 | 7/2015 | Bohlig et al. |
| 2015/0337206 | A1 | 11/2015 | Iwasa |
| 2016/0002546 | A1 | 1/2016 | Bai |
| 2016/0151765 | A1 | 6/2016 | Kamata et al. |
| 2017/0088783 | A1 | 3/2017 | Nawrocki |
| 2017/0226436 | A1 * | 8/2017 | Gillespie .................... C10J 3/66 |
| 2017/0312718 | A1 | 11/2017 | Tawfik |
| 2022/0135893 | A1 * | 5/2022 | Trapp ........................ C10J 3/84 48/197 R |
| 2022/0169931 | A1 * | 6/2022 | Trapp ...................... C10J 3/466 |

FOREIGN PATENT DOCUMENTS

| | | |
|---|---|---|
| CN | 101735011 A | 6/2010 |
| CN | 201626935 U | 11/2010 |
| CN | 101805636 B | 7/2013 |
| CN | 203923112 U | 11/2014 |
| CN | 104212471 A | 12/2014 |
| CN | 104479758 A | 4/2015 |
| CN | 104629806 A | 5/2015 |
| CN | 103205279 B | 7/2015 |
| CN | 105219437 A | 1/2016 |
| CN | 105299712 A | 2/2016 |
| CN | 103979491 B | 7/2016 |
| CN | 106381181 A | 2/2017 |
| CN | 106947509 A | 7/2017 |
| CN | 104789268 B | 12/2017 |
| CN | 107497467 A | 12/2017 |
| CN | 105462615 B | 4/2018 |
| CN | 105779017 B | 7/2018 |
| CN | 108557760 A | 9/2018 |
| DE | 42 00 341 A1 | 5/1993 |
| DE | 44 36 226 A1 | 4/1996 |
| DE | 44 46 803 A1 | 6/1996 |
| DE | 10 2016 002 029 B4 | 10/2018 |
| EP | 0 257 019 A2 | 2/1988 |
| EP | 1 462 505 A1 | 9/2004 |
| EP | 3 392 563 A1 | 10/2018 |
| GB | 2556665 A | 6/2018 |
| JP | 10-236801 A | 9/1998 |
| JP | 10-310783 A | 11/1998 |
| JP | 2000-328070 A | 11/2000 |
| JP | 2001-098276 A | 4/2001 |

(56)                References Cited

FOREIGN PATENT DOCUMENTS

| | | | |
|---|---|---|---|
| JP | 2002-038172 | A | 2/2002 |
| JP | 2003-238966 | A | 8/2003 |
| JP | 2003-246989 | A | 9/2003 |
| JP | 2004-315639 | A | 11/2004 |
| JP | 2006-328328 | A | 12/2006 |
| JP | 3980426 | B2 | 7/2007 |
| JP | 2008-063185 | A | 3/2008 |
| JP | 2008-249212 | A | 10/2008 |
| JP | 2009-235189 | A | 10/2009 |
| JP | 2009-300006 | A | 12/2009 |
| JP | 2011-006619 | A | 1/2011 |
| JP | 2017-180922 | A | 10/2017 |
| JP | 2017-193676 | A | 10/2017 |
| JP | 2017-195742 | A | 10/2017 |
| JP | 6280484 | B2 | 2/2018 |
| JP | 2018-043224 | A | 3/2018 |
| JP | 2018-053012 | A | 4/2018 |
| JP | 2018-123184 | A | 8/2018 |
| JP | 2018-123689 | A | 8/2018 |
| KR | 10-2002-0010902 | A | 2/2002 |
| KR | 10-0639113 | B1 | 10/2006 |
| KR | 10-2011-0000554 | A | 1/2011 |
| KR | 10-1669004 | B1 | 10/2016 |
| KR | 10-1721823 | B1 | 4/2017 |
| WO | WO 94/17161 | A1 | 8/1994 |
| WO | WO 2014/043552 | A1 | 3/2014 |
| WO | WO 2017/080933 | A1 | 5/2017 |
| WO | WO 2017/103527 | A1 | 7/2017 |
| WO | WO 2017/115019 | A1 | 7/2017 |
| WO | WO 2018/052337 | A1 | 3/2018 |

OTHER PUBLICATIONS

Co-pending U.S. Appl. No. 17/310,661 files Aug. 16, 2021; Trapp et al.
Co-pending U.S. Appl. No. 17/593,861, filed Sep. 26, 2021; Trapp et al.
Agrawal; "Compositional Analysis of Solid Waste and Refuse Derived Fuels by Thermogravimetry;" Compositional Analysis by Thermogravimetry; ASTM STP 997; C.M. Earnest, Ed.; American Society for Testing and Materials; Philadelphia; 1988; pp. 259-271.
Alter; "The Origins of Municipal Solid Waste: The Relations Between Residues from Packaging Materials and Food;" Waste Management & Research; 7; 1989; pp. 103-114.
Ashida et al.; "Co-pyrolysis of hydrothermally upgraded brown coal and waste plastics;" The Japan Institute of Energy; pp. 97-98.
Barton; "Processing of Urban Waste to Provide Feedstock for Fuel/Energy Recovery;" CEC International Conference, Pyrolysis and Gasification; Luxembourg; Warren Spring Lab Report No. W89026; May 1989; pp. 57-71.
Behzadi et al.; "Liquid Fuel from Plastic Wastes Using Extrusion—Rotary Kiln Reactors;" Chapter 19; Feedstock Recycling and Pyrolysis of Waste Plastics: Converting Waste Plastics into Diesel and Other Fuels; 2006; pp. 531-548.
Bhaskar et al.; "Pyrolysis studies of PP/PE/PS/PVC/HIPS-Br plastics mixed with PET and dehalogenation (Br, Cl) of the liquid products;" J. Anal. Appl. Pyrolysis; 72; 2004; pp. 27-33.
Blazsó; "Recent trends in analytical and applied pyrolysis of polymers;" Journal of Analytical and Applied Pyrolysis; 39; 1997; pp. 1-25.
Campbell et al.; "The potential for adding plastic waste fuel at a coal gasification power plant;" Waste Manage Res; 2001; 19; ; pp. 526-532.
De Marco et al.; "Recycling polymeric wastes by means of pyrolysis;" J Chem Technol Biotechnol; 77; online: 2002; pp. 817-824.
Elam et al.; "An Integrated Approach to the Recovery of Fuels and Chemicals from Mixed Waste Carpets Through Thermocatalytic Processing;" American Chemical Society, Division of Fuel Chemistry; 1997; 42(4); pp. 993-997.
Encyclopedia of Polymer Science and Technology; Copyright John Wiley & Sons, Inc.; vol. 7; pp. 657-678.

Feng et al.; "Pyrolysis Characteristics and Kinetics of Waste Plastics and Coal Powder;" Journal of Iron and Steel Research; vol. 18; No. 11; Nov. 2006; pp. 11-14, 26.
Fernandez; "La Recuperacion de Los Residuos Plasticos;" Ingenieria Quimica; Octubre 1997; pp. 153-157.
Fernandez; "Reciclado Quimico de Plasticos;" Revista de Plasticos Modernos; No. 477; Marzo 96; pp. 290-301.
García et al.; "Comparison between product yields in the pyrolysis and combustion of different refuse;" J. Anal. Appl. Pyrolysis; 68-69; 2003; pp. 577-598.
Helt et al.; "Liquids from Municipal Solid Waste;" Chapter 8; Soltes and Milne; Pyrolysis Oils from Biomass; ACS Symposium Series; American Chemical Society; Washington, DC; 1988; pp. 79-91.
Huczko et al.; "Plasma Gasification of Surrogate and Real Waste Plastics;" Thermal Solid Waste Utilisation in Regular and Industrial Facilities; 2000; pp. 155-165.
Hujuri et al.; "Modeling pyrolysis kinetics of plastic mixtures;" Polymer Degradation and Stability; 93; 2008; pp. 1832-1837.
Jung; "Pyrolysis and Gasification of Industrial Waste Towards Substitution Fuels Valorisation;" High Temperature Materials and Process Special Issue; vol. 27; No. 5; 2008; pp. 299-304.
Kaminsky; "Chemical Recycling of Mixed Plastics by Pyrolysis;" Advances in Polymer Technology; vol. 14; No. 4; 1995; pp. 337-344.
Kaminsky et al.; "Olefins from polyolefins and mixed plastics by pyrolysis;" Journal of Analytical and Applied Pyrolysis; 32; 1995; pp. 19-27.
Kaminsky et al.; "Pyrolysis of Plastic Waste and Scrap Tires Using a Fluidized-Bed Process;" Chapter 31; Jones and Radding; Thermal Conversion of Solid Wastes and Biomass; ACS Symposium Series; American Chemical Society; Washington, DC; 1995; pp. 423-439.
Kelly et al.; "A Low Cost and High Quality Solid Fuel From Biomass and Coal Fines;" Final Report; DOE Contract No. DE-AC26-99FT40157; Mar. 1, 1999 to May 31, 2000; Altex Technologies Corporation; Jul. 2001; pp. 1-122.
Kim et al.; "Pyrolysis of a fraction of mixed plastic wastes depleted in PVC;" Journal of Analytical and Applied Pyrolysis; 40-41; 1997; pp. 365-372.
Lin; "Recycling Technology of Poly(ethylene Terephthalate) Materials;" Macromol. Symp.; 135; 1998; pp. 129-135.
Luska et al.; "Piroliza jako jedna z metod recyklingu odpadow polimerowych;" Elastomery; Nr 5; pp. 30-36.
Mackey; "A Review of Advanced Recycling Technology;" Chapter 14; Rader et al.; Plastics, Rubber, and Paper Recycling; ACS Symposium Series; American Chemical Society; Washington, DC; 1995; pp. 161-169.
Mallya et al.; "Effects of Feedstock Components on Municipal Solid Waste Pyrolysis;" A.V. Bridgwater et al. (eds.), Research in Thermochemical Biomass Conversion; 1988; pp. 111-126.
Notification of Transmittal of the International Search Report and the Written Opinion of the International Searching Authority, or the Declaration, with Date of Mailing Jun. 30, 2020 received in International Application No. PCT/US2020/024841.
Notification of Transmittal of the International Search Report and the Written Opinion of the International Searching Authority, or the Declaration, with Date of Mailing Jul. 10, 2020 received in International Application No. PCT/US2020/024858.
Notification of Transmittal of the International Search Report and the Written Opinion of the International Searching Authority, or the Declaration, with Date of Mailing Jul. 10, 2020 received in International Application No. PCT/US2020/024851.
Notification of Transmittal of the International Search Report and the Written Opinion of the International Searching Authority, or the Declaration, with Date of Mailing Jul. 10, 2020 received in International Application No. PCT/US2020/024867.
Notification of Transmittal of the International Search Report and the Written Opinion of the International Searching Authority, or the Declaration, with Date of Mailing Jul. 10, 2020 received in International Application No. PCT/US2020/024833.
Notification of Transmittal of the International Search Report and the Written Opinion of the International Searching Authority, or the Declaration, with Date of Mailing Jul. 16, 2020 received in International Application No. PCT/US2020/024836.

(56)                  References Cited

OTHER PUBLICATIONS

Notification of Transmittal of the International Search Report and the Written Opinion of the International Searching Authority, or the Declaration, with Date of Mailing Jul. 17, 2020 received in International Application No. PCT/US2020/024855.

Notification of Transmittal of the International Search Report and the Written Opinion of the International Searching Authority, or the Declaration, with Date of Mailing Jul. 10, 2020 received in International Application No. PCT/US2020/024891.

Notification of Transmittal of the International Search Report and the Written Opinion of the International Searching Authority, or the Declaration, with Date of Mailing Jul. 21, 2020 received in International Application No. PCT/US2020/024887.

Okuwaki; "Feedstock recycling of plastics in Japan;" Polymer Degradation and Stability; 85; 2004; pp. 981-988.

Parra et al.; "Textural characterization of activated carbons obtained from poly(ethylene terephthalate) by carbon dioxide activation;" Studies in Surface Science and Catalysis; 144; pp. 537-543.

Parra et al.; "Textural development and hydrogen adsorption of carbon materials from PET waste;" Journal of Alloys and Compounds; 379; 2004; pp. 280-289.

Piao et al.; "Research and Development on Gasification Technology of Organic Waste Material (OWM) by using Entrained-Flow;" Journal of the Japan Institute of Energy; 82; 2003; pp. 671-678.

Pober et al.; "The Nature of Pyrolytic Oil from Municipal Solid Waste;" Chapter V; Fuels Waste; 1977; pp. 73-85.

Probert et al.; "Harnessing Energy from Domestic, Municipal and Industrial Refuse;" Applied Energy; 27; 1987; pp. 89-168.

Rago et al.; "Torrefaction of textile waste for production of energy-dense biochar using mass loss as a synthetic indicator;" Journal of Environmental Chemical Engineering; 6; 2018; pp. 811-822.

Roy et al.; "Preliminary Feasibility Study of the Biomass Vacuum Pyrolysis Process;" A.V. Bridgwater et al. (eds.); Research in Thermochemical Biomass Conversion; pp. 585-596.

Saha et al.; "Model-free method for isothermal and non-isothermal decomposition kinetics analysis of PET sample;" Thermochimica Acta; 444; 2006; pp. 46-52.

San José et al.; "Fluidodinamica de Los Lechos de Borbor Conicos (Spouted Beds) Para el Tratamiento de REsiduos de Materiales Plasticos;" Informacion Tecnologica; vol. 13; No. 5; 2002; pp. 21-24.

Savage et al.; "Screening Shredded Municipal Solid Waste;" Compost Science Journal of Waste Recycling; Jan./Feb. 1976; pp. 7-11.

Senneca et al.; "Oxidative pyrolysis of solid fuels;" J. Anal. Appl. Pyrolysis; 71; 2004; pp. 959-970.

Shah et al.; "Conversion of Waste Plastic to Oil: Direct Liquefaction versus Pyrolysis and Hydroprocessing;" Energy & Fuels; 13; 1999; pp. 832-838.

Shoji et al.; "Thermal weight analysis of the jet floor gasification process of wasteTen;" Journal of Chemical Engineering; pp. 27-34 (machine translation).

Straka et al.; "Co-pyrolysis of Waste Polymers with Coal;" Macromol. Symp.; 135; 1998; pp. 19-23.

Vasile et al.; "Thermal and catalytic decomposition of mixed plastics;" Journal of Analytical and Applied Pyrolysis; 57; 2001; pp. 287-303.

Vivero et al.; "Effects of plastic wastes on coal pyrolysis behavior and the structure of semicokes;" J. Anal. Appl. Pyrolysis; 74; 2005; pp. 327-336.

Wilkins et al.; "Review of pyrolysis and combustion products of municipal and industrial wastes;" Journal of Environmental Science & Health Part A; 18:6; 1983; pp. 747-772.

Williams et al.; "Interaction of Plastics in Mixed-Plastics Pyrolysis;" Energy & Fuels; 13; 1999; pp. 188-196.

Williams et al.; "The Pyrolysis of Individual Plastics and a Plastic Mixture in a Fixed Bed Reactor;" J. Chem. Tech. Biotechnol.; 70; 1997; pp. 9-20.

Williams et al.; "The pyrolysis of municipal solid waste;" Journal of the Institute of Energy; Dec. 1992; 65; pp. 192-200.

Williams et al.; "Recycling plastic waste by pyrolysis;" Journal of the Institute of Energy; Jun. 1998; 71; pp. 81-93.

Zhiyuan et al.; "The release law of benzene, radon and fife in the process of pyrococosatic and plastic pyrolytic process;" Environmental Chemistry; vol. 27; No. 6; Nov. 2008; pp. 766-769 (machine translation).

Notice of Allowance dated Nov. 20, 2024 received in co-pending U.S. Appl. No. 17/593,861.

* cited by examiner

Net Reactions:

$CO + H_2 \rightarrow CH_3OH$  (methanol)

$CH_3OH + CO \rightarrow CH_3COOH$  (acetic acid)

$CH_3OH + CH_3COOH \rightarrow CH_3CO_2CH_3$  (methyl acetate)

$CO + CH_3CO_2CH_3 \rightarrow (CH_3CO)_2O$  (acetic anhydride)

GASIFICATION OF DENSIFIED TEXTILES AND SOLID FOSSIL FUELS TO PRODUCE ORGANIC COMPOUNDS

CROSS-REFERENCE TO RELATED APPLICATION(S)

This application is a national stage filing under 35 USC § 371 of International Application Number PCT/US2020/024851, filed on, Mar. 26, 2020 which claims the benefit of the filing date to U.S. Provisional Application No. 62/825,880, filed on Mar. 29, 2019 and U.S. Provisional Application No. 62/906,832, filed on Sep. 27, 2019, the entire disclosures of which are incorporated by reference herein.

BACKGROUND

There is a well-known global issue with waste disposal, particularly of large volume consumer products such as size reduced textiles, size reduced textiles, textiles and other polymers that are not considered biodegradable within acceptable temporal limits. There is a public desire to incorporate these types of wastes into new products through recycling, reuse, or otherwise reducing the amount of waste in circulation or in landfills.

A variety of means for the recycle, reuse, or reduction of waste stocks such as biomass, solid municipal waste, and paper have been articulated, among which is the gasification of such waste stocks. In such proposals, waste gasifiers, which typically air supplied fluidized bed gasifiers that can readily accept a variety of component sizes and mixed stock types have been proposed or used. Such waste gasifiers typically operate at low to medium temperatures in the range of 500° C. to 1000° C. using air as an oxidizer, and given the lower operating temperature, incomplete oxidation reactions occur resulting the generating of high quantities of residues that can appear in both the gas phase (syngas stream) and bottoms solid phase; e.g. tarry substances. The types of residues and their quantity will vary depending on the feedstock composition. Further, while waste gasifiers have the advantage of accepting a highly variable sizes and compositions of feedstocks, the resulting syngas compositions are also widely variable over time rendering them unusable for making chemicals without installation of expensive post treatments systems to clean up and purify the syngas streams existing the gasifier vessel. Even with purification processes, the hydrogen/carbon monoxide/carbon dioxide ratios can remain highly variable. As a result of the expense to install systems to purify the syngas stream exiting the gasifier vessel suitable for chemicals synthesis, or their compositional variability, or their low throughput, or by reason of a combination of these factors, waste gasifier generated syngas streams are typically used to generate energy, e.g. steam or electricity or are used as fuel stocks.

Separated portions of mixed solid municipal wastes (MSW) have been investigated as a feed to a gasifier. MSW compositions contain a variety of solids, including bottles, sheets, films, paper, rubber, cardboard, cups, trays, wood, leather, textiles, glass, metal, etc. After separation of combustibles from non-combustibles (e.g. glass, metal, dirt), the mix of combustibles nevertheless remains highly variable in time from hour to hour, day to day, week to week, month to month, season to season, and by the source location. The variability lies both in form, e.g. bottles, garments, other textiles, personal care items, sheets, films, paper, cardboard, cups, trays, etc., and variability in compositional mix, e.g.

polycarbonate, polyethylene, polypropylene, polyethylene terephthalate, polyamides, epoxy resins, acrylonitrilebutadiene, acrylics, alkyds, nylons, polyacetals, polystyrene, polyurethanes, vinyls, styrene acrylonitriles, ureas and melamines, wood, cellulosics, leather, food wastes, etc., variability in source location, and variability in the large variety of mechanical handling processes commercially practiced which employ different physical and chemical separation methods. In fixed bed and fluidized bed gasifiers, this can result in an unacceptable syngas composition variability over time, particularly when the syngas is needed to synthesize chemicals which require a very consistent rate and quality of syngas or syngas ingredients.

Additionally, size reduced textiles and textiles have a fixed carbon content that is lower than solid fossil fuel sources such as coal or petcoke. As a result, size reduced textiles and textiles will combust and generate the syngas components at a more rapid rate than, for example, coal. Carbon monoxide generated from size reduced textiles or textiles will, therefore, have a longer residence time to convert to carbon dioxide under gasification conditions, relative to coal. While size reduced textiles and textiles have a high heat value ("HHV"), even in some cases equal to or exceeding coal, its use can also result in the generation of undesirable amounts of carbon dioxide in the raw syngas stream, particularly at high temperatures and pressures, along with a reduction in the amount of carbon monoxide that could have been produced by feeding only a fossil fuel. In addition, size reduced textiles and textiles have a higher hydrogen content that does, for example, solid fossil fuels, which can lead to the production of higher amounts of hydrogen in the raw syngas stream and affect the carbon monoxide/hydrogen ratio. These issues are not a concern when syngas is used for generating electricity or burned for heat value, but become a concern when making chemicals since the manufacture of chemicals relies on consistent output, ratio of carbon monoxide and/or hydrogen as raw materials for chemicals, and impurity types and profile in the syngas stream, particularly the lack of tarry residues or concentration of soot.

We desire to employ a method for providing a circular life cycle of fibers in textiles that includes recycling postconsumer or post-industrial textiles back to a molecular form suitable for making chemicals. The fixed bed waste gasifiers employed to accept combustible MSW streams are not an attractive alternative for generating a syngas stream for making chemicals for the reasons stated above. Many large-scale commercial gasifiers used to make pure consistent syngas streams at high output have a variety of constraints against accepting MSW or the components of MSW, such constraints depending on the type of gasifier employed. For example, entrained flow gasifiers employing feed injectors are not amenable to injecting the textiles in the form found in MSW. Even if the textiles are reduced to a very small size, their variable composition between natural and synthetic fibers, and different types of synthetic fibers, can cause screening or filtration plugging if co-ground with other solid fuels, or may lead to unstable slurries. The configuration of updraft fixed bed or updraft moving bed gasifiers that have a countercurrent flow of gas through the bed make it difficult to handle fines. For example, fine fibers introduced at the top of a fixed or moving downdraft gasifier may not uniformly settle onto the lower bed to form a fine char and gasify.

Further, textiles introduced into liquid or slurry fed gasifiers may not homogeneously disperse into the slurry, dispersion, or solution fed to the gasifier.

It would be desirable to incorporate textiles into a feedstock to a gasifier producing a syngas stream suitable for making chemicals. We also desire to employ a method of gasification of textiles stream that would generate a syngas stream suitable for chemicals synthesis in which more complete oxidation of waste feedstocks occurs to reduce the quantity of incomplete oxidation residues. It would also be desirable to generate a syngas stream suitable for chemicals synthesis in which more carbon monoxide is formed in the syngas using feedstocks containing textiles relative to lower temperature and/or lower pressure MSW fed fixed bed waste gasifiers, and to reduce the quantity of incomplete oxidation residues (e.g. tar, char, etc.). We also desire to generate a syngas stream output from a gasifier vessel which is sufficiently compositionally consistent over time and suitable for making chemicals, and particularly without the need for blending syngas streams. It is also desirably to conduct the operations efficiently, in a stable manner, and on a commercial scale.

While it is desirable to have minimal syngas compositional variation generated from feedstocks containing textiles and a fossil fuel, it is also desirable to have a flexible process in that the textiles can be fed intermittently (or semi-continuously) without wide variations on the syngas composition between syngas generated from feeds with the textiles and syngas generated from feeds without the recycle material.

Given that textiles can float, or phase separate, or agglomerate, or disrupt the homogeneity of a slurry or solution, there also remains a need to generate a feedstock containing textiles that is stable and pumpable.

A coal-water slurry fed gasifier used to generate syngas for chemical production generally runs at high pressures and utilizes a slurry feed (coal and water) that can be more easily pumped and fed into the gasifier. A small amount of water introduced to the gasification process is helpful and needed (e.g. 5-20%) but more than 30% begins to be detrimental to the performance of the gasifier as the water must be heated and vaporized, using energy, and takes up space in the processing equipment. Therefore, the slurry should be as concentrated in coal as possible but still fluid enough to pump. The practical range for coal/water slurry concentrations is 50%-75% coal. To make these concentrations possible, the coal is finely ground. Introducing a co-feed to the gasifier can be problematic in that the co-feed has to be mixed with the coal/water slurry feed. Since the coal/water slurry is concentrated as much as possible to the edge of pumpability for economic reasons, any introduction of a co-feed can disrupt the delicate balance and cause the slurry to be unstable (solids settle out), too viscous, two-phase, or otherwise unsuitable for feeding to the gasifier safely, reliably, and economically. For example, many plastics and textiles will float, or phase separate, or agglomerate and disrupt the homogeneity of the slurry.

There remains a need to gasify textile material in a slurry that is stable. There also remains a need to ensure that such slurry is pumpable.

There remains a need to gasify textiles that includes coal without generating high amounts of tar, or optionally also high amounts of other incomplete oxidation residues, as would be encountered in fixed or fluidized bed waste gasifiers.

There is also a need to gasify a mixed stream containing textiles to provide a syngas stream with minimal compositional variability over time.

There is also a need to provide an intermittent co-feed of textiles with a solid fossil fuel while maintaining a minimal syngas compositional variability over time frames that includes feedstocks with and without the textile waste material.

There is also a need to generate such syngas streams using textiles as part of a feedstock that are suitable for making chemicals and optionally but desirably without the need to install and operate additional equipment to clean up the syngas stream exiting the gasifier vessel other than acid gas removal processes (e.g. removal of hydrogen sulfide and carbon dioxide) or processes internal to the gasifier vessel (e.g. quench to remove soot).

There is also a need to solve any combination of the above stated needs.

SUMMARY

There is now provided a process for the production of syngas comprising:

a. charging an oxidant and a feedstock composition to a gasification zone within a gasifier, said feedstock composition comprising densified textiles aggregates, optionally also a solid fossil fuel, optionally up to 25 wt. %, or up to 20 wt. %, or up 15 wt. %, or up to 12 wt. %, or up to 10 wt. %, or up to 7 wt. %, or up to 5 wt. %, or less than 5 wt. % densified textiles based on the weight of solids in the feedstock composition; and b. gasifying the feedstock composition together with the oxidant in a gasification zone to produce a syngas composition; and c. discharging at least a portion of the syngas composition from the gasifier.

Desirably the feedstock is a slurry.

There is also provided a process for the production of syngas comprising:

a. charging an oxidant and a feedstock slurry composition to a gasification zone within a gasifier, said feedstock slurry composition comprising densified textile aggregates and least 90 wt. % of the densified textile aggregates have a particle size in the largest dimension of not more than 2 mm;

b. gasifying the feedstock composition together with the oxidant in a gasification zone to produce a syngas composition; and c. discharging at least a portion of the syngas composition from the gasifier.

There is also provided a process for the production of syngas comprising:

a. charging an oxidant and a feedstock slurry composition to a gasification zone within a gasifier, said feedstock slurry composition comprising densified textile aggregates;

b. gasifying the feedstock composition together with the oxidant in a gasification zone to produce a syngas composition; and c. discharging at least a portion of the syngas composition from the gasifier, wherein at least one of the following conditions is present:

(i) gasification within the gasification zone is conducted at a temperature of at least 1000° C., or (ii) the pressure within the gasification zone greater than 2.7 MPa, or (iii) the feedstock composition comprises a slurry, or (iv) the densified textile aggregates are pre-ground to particles, or (v) no steam is introduced to the gasifier that flows into the gasification zone, or (vi) the particle size of the size reduced textiles is such that at least 90% of the particles have a particle size of less than 2 mm, or (vii) the tar yield is less than 4 wt. %, or (viii) the gasifier contains no membrane wall in the gasification zone, or (ix) a combination of two or more of the above conditions.

There is further provided a composition comprising:

a. densified textile aggregates; and b. solid fossil fuel.

There is also provided a composition comprising:

a. densified textile aggregates, and b. a hydrocarbon liquid that is liquid at 25° C. and 1 atmosphere.

There is also provided a feedstock slurry composition comprising densified textile aggregates, a solid fossil fuel, and water, wherein densified textile aggregates has a particle size of not more than 2 mm, and the solid fossil fuel in the feedstock composition has a particle size of less than 2 mm, the solids content in the slurry is at least 62 wt. % (or at least 65 wt. %, or at least 68 wt. %, or at least 69 wt. %, or at least 70 wt. %), the amount of densified textile aggregates present in the feedstock stream slurry composition is 0.1 wt. % to up to 25 wt. %, or up to 20 wt. %, or up 15 wt. %, or up to 12 wt. %, or up to 10 wt. %, or up to 7 wt. %, or up to 5 wt. %, or less than 5 wt. % based on the weight of all solids in the slurry, and the water is at least 20 wt. % based on the weight of the feedstock slurry composition, and wherein either:

a. the slurry is stable as determined by having an initial viscosity of 100,000 cP or less at 5 minutes, or 10 minutes, or 15 minutes, or 20 minutes, or 25 minutes, or even for 30 minutes using a Brookfield R/S Rheometer equipped with V80-40 vane operating at a shear rate of 1.83/ s or a Brookfield viscometer with an LV-2 spindle rotating at a rate of 0.5 rpm, measured at ambient conditions; or b. the slurry is pumpable as determined by having a viscosity of less than 30,000 cP, or 25,000 cP or less, or not more than 23,000 cP, or not more than 20,000 cP, or not more than 18,000 cP, or not more than 15,000 cP, or not more than 13,000 cP, after mixing to obtain a homogeneous distribution of solids throughout the slurry and using a Brookfield R/S Rheometer equipped with V80-40 vane an LV-2 spindle rotating at a rate of 0.5 rpm, measured at ambient conditions, or c. both.

There is also provided a syngas composition discharged from a gasifier and obtained by gasifying a feedstock composition comprising densified textile aggregates, and said syngas stream contains no tar or less than 4 wt. % (or less than 3 wt. %, or not more than 2 wt. %, or not more than 1 wt. %, or not more than 0.5 wt. %, or not more than 0.2 wt. %, or not more than 0.1 wt. %, or not more than 0.08 wt. %, or not more than 0.05 wt. %, or not more than 0.02 wt. %, or not more than 0.01 wt. %, or nor more than 0.005 wt. %) tar, based on the weight of all condensable solids in the syngas composition.

There is further provided a syngas stream composition produced by gasifying in a gasifier, as well as a process for making a syngas stream by gasifying in a gasifier, a feedstock comprising densified textile aggregates wherein said syngas stream has a compositional variability that is 5% or less measured over a time period that is the lesser of 12 days or the time period the feedstock is fed to the gasifier, said syngas compositional variability satisfied against at least one of the following gaseous compounds (in moles):

a. CO amount, or b. H2 amount, or c. CO2 amount, or d. CH4 amount, or e. H2S amount, or f. COS amount, or g. H2+CO amount, or its molar ratio in sequence (e.g. H2: CO ratio), or h. H2+CO+CO2 amount, or its molar ratio in sequence, or i. H2+CO+CH4 amount, or its molar ratio in sequence, or j. H2+CO+CO2+CH4 amount, or its molar ratio in sequence, or k. H2S+COS amount, or its molar ratio in sequence, or l. H2+CO+CO2+CH4+H2S+COS.

There is also provided a syngas composition stream having a switching variability that is negative, zero, or not more than 15%, wherein the switching frequency is at least 1 time every two years, and the switching variability is determined by the following equation:

$$\% \; SV = \frac{V_{dt} - V_{\mathit{ffl}}}{V_{\mathit{ffl}}} \times 100$$

where % SV is percent syngas switching variability on one or more measured ingredients in the syngas composition; and $V_{dt}$ is the syngas compositional variability of a gaseous compound(s) using a feedstock comprising densified textile aggregates; and $V_{\mathit{ffl}}$ is the syngas compositional variability of the same gaseous compound(s) using a fossil fuel only stream or a liquid stream only as the feedstock, and where the feedstocks are gasified under the same conditions, other than temperature fluctuations which may autogenously differ as a result of having densified textile aggregates in the feedstock, and the variabilities are measured and satisfied against at least one of the following gaseous compounds (in moles):

a. CO amount, or b. H2 amount, or c. CO2 amount, or d. CH4 amount, or e. H2S amount, or f. COS amount, or g. H2+CO amount, or its molar ratio in sequence (e.g. H2: CO ratio), or h. H2+CO+CO2 amount, or its molar ratio in sequence, or i. H2+CO+CH4 amount, or its molar ratio in sequence, or j. H2+CO+CO2+CH4 amount, or its molar ratio in sequence, or k. H2S+COS amount, or its molar ratio in sequence, or l. H2+CO+CO2+CH4+H2S+COS.

Ideally, a densified textile aggregates includes densified textile particles that, within a particle, contains a thermoplastic polymer or a combination of thermoplastic polymers and natural fibers.

DETAILED DESCRIPTION

Figure 1:
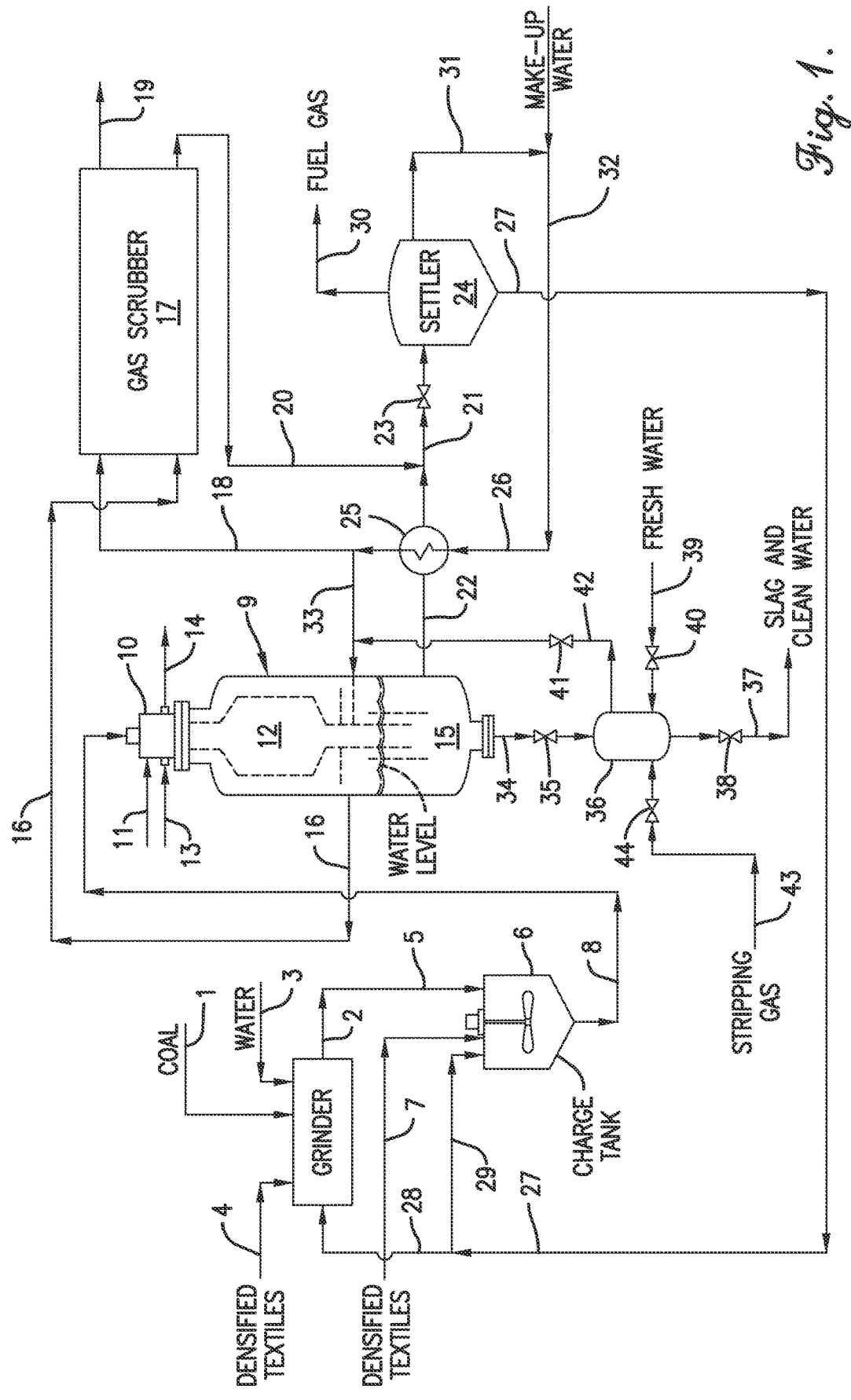
FIG. 1 is a schematic plant design for combining densified textile aggregates and solid fossil fuel as a feedstock to a gasification process to produce syngas.

Unless otherwise stated, reference the weight of the feedstock composition or stream includes all solids, and if present liquids, fed to the gasifier, and unless otherwise stated, does not include the weight of any gases in the feedstock composition as fed to the injector or gasifier. A composition or a stream are used interchangeably.

A feedstock stream or composition is used interchangeably with a fuel feedstock stream or composition, and contains at least a fossil fuel in the form or a solid or liquid, and a size reduced textile. When weight percentages are express based on the feedstock stream or fuel feedstock, they exclude the oxidant.

A PIA or PIA reactant or composition or compound is associated with, or originates from, a recycle textile, size reduced textiles, densified textiles, or densified textile derived syngas if any one of them are subjected to partial oxidation gasification, regardless of when the allotment is taken, realized, or consumed. For example, a PIA can be associated with a densified textile that is gasified even though the allotment is taken and deposited into a recycle inventory or transferred to a PIA when recycle textiles are received or possessed or owned by a syngas manufacturer and even though the densified textile is not gasified at the time the allotment is taken. Further, an allotment that is associated with or originates from gasifying a densified textile does not limit the timing of taking or recognizing the allotment or depositing the allotment into a recycle inventory. An allotment taken when a recycle textile (textile, size reduced textile, or densified textile) is owned, possessed, or receiving by a syngas manufacturer and deposited into a recycle inventory is an allotment that is associated with or originates from gasifying a densified textile even though, at the time of taking or depositing the allotment, the densified textile has not yet been gasified.

As used throughout, the phrase "originates" or "origin" is synonymous to "associated with."

For purposes of classifying materials in the feedstock stream or composition, a solid fossil fuel used can be coal, petcoke, or any other solid at 25° C. and 1 atmosphere that is a byproduct from refining oil or petroleum. The fossil fuel portion of the feedstock composition is to be distinguished from densified textile aggregates, even if the densified textile aggregates are carbonaceous and in part derived from raw materials obtained from refining crude oil. A fossil fuel can include liquid fossil fuels, such as liquid hydrocarbons or streams obtained from refining crude oil, or waste streams from chemical synthetic processes.

Generally, in a synthesis gas operation one or more feedstock composition(s) comprised of fossil fuel sources (e.g. coal, petcoke, liquid hydrocarbons) and densified textile aggregates as an individual stream or combined with the fossil fuel source streams, and optionally water and other chemical additives, are fed or injected along with an oxidizer gas into a gasification reaction zone or chamber of a synthesis gas generator (gasifier) and gasified in the presence of an oxidizer such as oxygen, also fed to the gasifier. A hot gas stream is produced in the gasification zone, optionally refractory lined, at high temperature and high pressure generating a molten slag, soot, ash and gases including hydrogen, carbon monoxide, carbon dioxide and can include other gases such as methane, hydrogen sulfide and nitrogen depending on the fuel source and reaction conditions. The hot gas stream is produced in the reaction zone is cooled using a syngas cooler or in a quench water bath at the base of the gasifier which also solidifies ash and slag and separates solids from the gases. The quench water bath also acts as a seal to maintain the internal temperature and pressure in the gasifier while the slag, soot and ash are removed into a lock hopper. The cooled product gas stream removed from the gasifier (the raw syngas stream) can be further treated with water to remove remaining solids such as soot, and then further treated to remove acid gas (e.g. hydrogen sulfide) after optionally further cooling and shifting the ratio of carbon monoxide to hydrogen.

The densified textile aggregates employed in the feedstock stream to the gasifier are solid at 25° C. at 1 atm. The densified textile aggregates are a collection of particles, briquettes, agglomerates, pellets, or rods, or any other shape or size that different from the native shape of the textile from which the densified textile aggregate is made. The densified textile and/or plastic aggregates can be agglomerates, or they can be extrudates or pellets.

Textiles as used herein are natural and/or synthetic fibers, rovings, yarns, nonwoven webs, cloth, fabrics and products made from or containing any of the aforementioned items, provided that the textiles are either post-consumer or post-industrial textiles. Textiles can be woven, knitted, knotted, stitched, tufted, pressing of fibers together such as would be done in a felting operation, embroidered, laced, crocheted, braided, or nonwoven webs and materials. Textiles as used herein include fabrics, and fibers separated from a textile or other product containing fibers, scrap or off spec fibers or yarns or fabrics, or any other source of loose fibers and yarns. A textile also includes staple fibers, continuous fibers, threads, tow bands, twisted and/or spun yarns, grey fabrics made from yarns, finished fabrics produced by wet processing gray fabrics, and garments made from the finished fabrics or any other fabrics. Textiles include apparels, interior furnishings, and industrial types of textiles. Textiles also include post-industrial textiles or post-consumer textiles or both.

Examples of textiles in the apparel category (things humans wear or made for the body) include sports coats, suits, trousers and casual or work pants, shirts, socks, sportswear, dresses, intimate apparel, outerwear such as rain jackets, cold temperature jackets and coats, sweaters, protective clothing, uniforms, and accessories such as scarves, hats, and gloves. Examples of textiles in the interior furnishing category include furniture upholstery and slipcovers, carpets and rugs, curtains, bedding such as sheets, pillow covers, duvets, comforters, mattress covers; linens, tablecloths, towels, washcloths, and blankets. Examples of industrial textiles include transportation (auto, airplanes, trains, buses) seats, floor mats, trunk liners, and headliners; outdoor furniture and cushions, tents, backpacks, luggage, ropes, conveyor belts, calendar roll felts, polishing cloths, rags, soil erosion fabrics and geotextiles, agricultural mats and screens, personal protective equipment, bullet proof vests, medical bandages, sutures, tapes, and the like.

The nonwoven webs that are classified as textiles do not include the category of wet laid nonwoven webs and articles made therefrom. While a variety of articles having the same function can be made from a dry or wet laid process, the article made from the dry laid nonwoven web is classified as a textile. Examples of suitable articles that may be formed from dry laid nonwoven webs as described herein can include those for personal, consumer, industrial, food service, medical, and other types of end uses. Specific examples can include, but are not limited to, baby wipes, flushable wipes, disposable diapers, training pants, feminine hygiene products such as sanitary napkins and tampons, adult incontinence pads, underwear, or briefs, and pet training pads. Other examples include a variety of different dry or wet wipes, including those for consumer (such as personal care or household) and industrial (such as food service, health care, or specialty) use. Nonwoven webs can also be used as padding for pillows, mattresses, and upholstery, batting for quilts and comforters. In the medical and industrial fields, nonwoven webs of the present invention may be used for medical and industrial face masks, protective clothing, caps, and shoe covers, disposable sheets, surgical gowns, drapes, bandages, and medical dressings. Additionally, nonwoven webs as described herein may be used for environmental fabrics such as geotextiles and tarps, oil and chemical absorbent pads, as well as building materials such as acoustic or thermal insulation, tents, lumber and soil covers and sheeting. Nonwoven webs may also be used for other consumer end use applications, such as for, carpet backing, packaging for consumer, industrial, and agricultural goods, thermal or acoustic insulation, and in various types of apparel. The dry laid nonwoven webs as described herein may also be used for a variety of filtration applications, including transportation (e.g., automotive or aeronautical), commercial, residential, industrial, or other specialty applications. Examples can include filter elements for consumer or industrial air or liquid filters (e.g., gasoline, oil, water), including nanofiber webs used for microfiltration, as well as end uses like tea bags, coffee filters, and dryer sheets. Further, nonwoven webs as described herein may be used to form a variety of components for use in automobiles, including, but not limited to, brake pads, trunk liners, carpet tufting, and under padding.

The textiles can include single type or multiple type of natural fibers and/or single type or multiple type of synthetic fibers. Examples of textile fiber combinations include all natural, all synthetic, two or more type of natural fibers, two or more types of synthetic fibers, one type of natural fiber and one type of synthetic fiber, one type of natural fibers and two or more types of synthetic fibers, two or more types of natural fibers and one type of synthetic fibers, and two or more types of natural fibers and two or more types of synthetic fibers.

Polymers used to make the synthetic fibers can be thermoplastic or thermosetting polymers. The polymer number average molecular weight can be at least 300, or at least 500, or at least 1000, or at least 5,000, or at least 10,000, or at least 20,000, or at least 30,000, or at least 50,000 or at least 70,000 or at least 90,000 or at least 100,000 or at least 130,000. The weight average molecular weight of the polymers can be at least 300, or at least 500, or at least 1000, or at least 5,000, or at least 10,000, or at least 20,000, or at least 30,000 or at least 50,000, or at least 70,000, or at least 90,000, or at least 100,000, or at least 130,000, or at least 150,000, or at least 300,000.

Natural fibers include those that are plant derived or animal derived. Natural fibers can be cellulosics, hemicellulosics, and lignins. Examples of plant derived natural fibers include hardwood pulp, softwood pulp, and wood flour; and other plant fibers including those in wheat straw, rice straw, abaca, coir, cotton, flax, hemp, jute, bagasse, kapok, papyrus, ramie, rattan, vine, kenaf, abaca, henequen, sisal, soy, cereal straw, bamboo, reeds, esparto grass, bagasse, Sabai grass, milkweed floss fibers, pineapple leaf fibers, switch grass, lignin-containing plants, and the like. Examples of animal derived fibers include wool, silk, mohair, cashmere, goat hair, horsehair, avian fibers, camel hair, angora wool, and alpaca wool.

Synthetic fibers are those fibers that are, at least in part, synthesized or derivatized through chemical reactions, or regenerated, and include, but are not limited to, rayon, viscose, mercerized fibers or other types of regenerated cellulose (conversion of natural cellulose to a soluble cellulosic derivative and subsequent regeneration) such as lyocell (also known as Tencel), Cupro, Modal, acetates such as polyvinylacetate, polyamides including nylon, polyesters such as those polyethylene terephthalate (PET), copolyesters including those made with IPA, CHDM and/or 2,2,4,4-tetramethyl-1,3-cyclobutanediol, polycyclohexylenedimethylene terephthalate (PCT) and other copolymers, olefinic polymers such as polypropylene and polyethylene, polycarbonates, poly sulfates, poly sulfones, polyethers such as polyether-urea known as Spandex or elastane, polyacrylates, acrylonitrile copolymers, polyvinylchloride (PVC), polylactic acid, polyglycolic acid, sulfopolyester fibers, and combinations thereof.

The densified textile aggregates are obtained from post-consumer textiles and/or post-industrial textiles (also commonly known as pre-consumer textiles). Post-consumer textiles are those that have been used at least once for its intended application for any duration of time regardless of wear. Post-industrial densified textile aggregates include rework, regrind, scrap, trim, out of specification textiles (e.g. fibers, yarns, webs, cloths, fabrics, finished textiles) that have not been used for their intended application, or any textiles that have not been used by the end consumer.

The form of the textiles useful to make densified textile aggregates are not limited, and can include any of the forms of articles or materials used to make textiles described above; e.g. fibers, yarns, fabrics, cloths, finished article forms, or pieces thereof. The densified textile aggregates can be of varying age and composition.

The source of the post-consumer or postindustrial textiles is not limited, and can include textiles present in and separated from municipal solid waste streams ("MSW"). For example, an MSW stream can be processed and sorted to several discrete components, including textiles, fibers, papers, wood, glass, metals, etc. Other sources of textiles include those obtained by collection agencies, or by or for or on behalf of textile brand owners or consortiums or organizations, or from brokers, or from postindustrial sources such as scrap from mills or commercial production facilities, unsold fabrics from wholesalers or dealers, from mechanical and/or chemical sorting or separation facilities, from landfills, or stranded on docks or ships.

In one embodiment, the textiles used to make the densified textiles are within one of the components or streams that are separated from an MSW source.

The densified textile aggregates are fed as a fuel for gasification, or to a gasifier neat, or slurried and fed to a gasifier.

To obtain the densified textile aggregates, the textiles are reduced in size by any means, including by chopping, grinding, shredding, harrowing, confrication, pulverizing, or cutting a feed of textiles to make size reduced textiles. Optionally, the size reduced textiles can continue to be ground, comminuted, pulverized or otherwise size reduced to obtain the desired average particle size if one desires to obtain finer particles. The form of the size reduced textiles will depend on the desired method of densification. For example, the size reduced textiles can be in the form of coarse or fine particles, even a powder (of any shape other than the original shape of the textile feed). Alternatively, the size reduced textiles can be in the form of a viscous mass that does not have discrete particles. Fluidized bed granulators can be used, optionally with a drying gas, as well as tumbling granulators of disc or drum design connected to high speed mixers having cutting blades on a horizontal or vertical shaft. Examples of different kinds of suitable size reducing processes and equipment as stand-alone or coupled together include air swept mills, knife cutting, fine grinders that can have multiple grinding zones with internal classification systems, choppers with finer knives at the end, disintegrators that can handle shredding of textiles even high moisture feeds and then optional fine cutting or milling into smaller size such as a powder, high speed cutting blades that can have multiple zones for moving coarser material to finer material. The size reducing equipment can also include drying before cutting or simultaneous with drying Following or simultaneous with the process of size reducing the textile feed, the size reduced textiles are treated to make a densified textile aggregates in which the individual particles in densified textile aggregates have a bulk density that is higher than the bulk density of the textile feed used to make the size reduced textiles. The densification process increases the bulk density of the textiles. In one embodiment or in combination with any of the mentioned embodiments, the bulk density of the densified textile aggregates is higher than the bulk density of the textiles fed to the process for size reduction. In one embodiment or in combination with any of the mentioned embodiments, the bulk density of the densified textile aggregates is higher than the bulk density of an isolated size reduced textiles.

The densification process is accomplished by forming agglomerates without application of external heat source (the "agglomeration process"), or by applying external heat energy in a process for forming particles ("heat treated process"). In one embodiment or in combination with any of the mentioned embodiments, the densified textile aggregates are obtained by an agglomeration process that includes pressure. In one embodiment or in combination with any of the mentioned embodiments, the densified textile aggregates are obtained by an agglomeration process that does not include application of pressure. In one embodiment or in combination with any of the mentioned embodiments, the densified textile aggregates are obtained by a heat-treated process that includes that application of pressure.

Examples of pressure agglomeration include compactors (roll, roll press, double roll press). Compactors roll the material into a sheet, and then feed the material to a flake breaker and granulator. The process is generally a dry process. Another example of pressure agglomeration includes briquetters which produce pillow shape agglomerates in the roll press or double roll press.

Examples of non-pressure agglomeration processes include forming agglomerates with disc pelletizers (also called pan pelletizers or granulators), agglomeration drums, pin mixers, and paddle mixers (pug mills).

Generally, the size of the agglomerates is higher than the size of the size reduced textiles by, for examples, combining or consolidating smaller particles into larger particles to make granules, tablets, briquettes, pellets, or the like. Since agglomerates are consolidated or pressure compacted rather than fused, they can break apart into smaller sizes more easily than extrudates in grinding or milling equipment, such as those used in a coal or petcoke grinder or mill. Agglomerates also produce fewer fines and dust and can easily flow.

The agglomerates, after formed, can be cured, dried, or fired by application of external heat sources.

In one embodiment or in combination with any of the mentioned embodiments, the size reduction process and the densification process in an agglomeration process can be in different zones in the same equipment, or in the same zone in the same equipment, or the size reduced textiles are not discharged and isolated before the application of a densification process. For example, a single equipment can both reduce the size of the textile feed and densify either in two zones within the body of the agglomerator or even in one zone within the body of the agglomerator.

In one embodiment or in combination with any of the mentioned embodiments, the size reduced textiles are discharged from equipment and isolated prior to feeding the size reduced textiles to a process for densification.

As noted, the densified textile aggregates can be formed by an agglomeration method. This can be accomplished in an agglomerator (also called a densifier) in a batch or continuous mode. The agglomeration method does not include application of external heat energy. In one embodiment or in combination with any of the mentioned embodiments, the agglomeration occurs with the application of frictional heat, or frictional heat only. There are many types of commercial agglomerators available capable of densifying plastics by similar processes. In one embodiment or in combination with any of the mentioned embodiments, the formation of size reduction and densification can occur in the same zone by feeding loose textiles to a chamber of spinning blades that shred the material for a time sufficient to frictionally heat the mass of shredded textiles to a softening point $T_g$ of thermoplastic polymer contained in the mass of shredded textiles, or otherwise to at least soften or create a tacky or viscous shredded mass. The softened size reduced viscous mass can optionally be densified and solidified by application of water onto the mass. This process does not isolate the size reduced textiles as particles before densification. The process of size reduction and densification can occur simultaneously. This process can also occur without applied pneumatic or hydraulic pressure during the shredding and densification process. The action of the spinning blades provides the motive force for discharging the densified textile aggregates. Pressure may be applied to discharge the material from the densification zone.

Size reduced textiles are any textiles which have been subjected to a process of cutting, shredding, pulverizing, chopping, or other means to reduce the size of textile from one size to a smaller size.

In another embodiment, the size reduced textiles are fed by a means such as a pneumatic conveyor to a hopper that can be stirred and then fed to an optional discharge auger or screw mounted perpendicular to the hopper or in line and parallel in the vertical plane to the hopper. The rotational speed of the auger or screw is determined by the desired throughput of the agglomeration screw. Optionally, the discharge port, screw, or any location between the hopper and agglomeration screw can be configured to check metal and removed, such as by way of magnets.

The discharge screw or auger feeds the size reduced textiles to an agglomeration zone containing a chamber in which the size reduced textiles are softened, plasticized, sintered, or otherwise compacted. One example of such a chamber is a single or double screw that either is tapered having a diameter that narrows through at least a portion of the shaft length toward the die head or outlet or a variable pitch and/or variable flight straight screw that provides compaction as the textile material moves toward the die head, or any other screw design that provides compaction. The chamber can optionally be vented. The shearing action of the screw and compaction of the textile material as it travels down the screw creates frictional heat to soften the textiles to a temperature effective to create an agglomerate. The screw can be a variable or constant pitch screw or have variable or constant flights. If a die is use, the holes can be configured to any shape and size. A set of rotating knives cut the agglomerated textile material exiting the die to form the densified textile aggregates.

In one embodiment or in combination with any of the mentioned embodiments, the textiles, size reduced textiles, and/or densified textile aggregates can be fed to chamber or process that applies heat energy to the textiles to melt at least a portion of the textiles. Examples include a hot melt granulator or extruder with a die.

In one embodiment or in combination with any of the mentioned embodiments, there is provided a molten blend of size reduced textiles obtained by any conventional melt blending techniques. A molten blend includes textiles completely melted or textiles containing a portion of material that is melted and a portion of material that is not melted. Some material in textiles will not melt before they thermally degrade, such as some natural fibers.

The melt blend can be cooled into sheet or pellet form. For example, the melt blend can be extruded into any form, such pellets, droplets, or other particles, strands, rods, or sheets, which can, if desired, be further granulated and/or pulverized to the desired size.

The type of densified textile aggregates is not limited, and can be any one of those mentioned below, but at least a portion of the textiles contain thermoplastic polymer. Thermoplastic polymers assist to retain the shape and particle integrity, allow their processing, and avoid excessive energy costs. Densified textile aggregates that do not contain any or insufficient thermoplastic polymer content will not retain a consistent discrete shape in downstream size reducing processes, will generate excessive fines, and can have a wide size variation. The amount of thermoplastic polymer, or thermoplastic fibers, in any one of the textile feed, size reduced textiles, or densified textile aggregates agglomerates is at least 5 wt. %, or at least 10 wt. %, or at least 25 wt. %, or at least 50 wt. %, or at least 75 wt. %, or at least 90 wt. %, or at least 98 wt. %, or 100 wt. %, based on the weight of the corresponding textile, i.e. textile feed, size reduced textiles, or densified textile agglomerates.

The source of thermoplastic polymer in the textiles, size reduced textiles, or densified agglomerates can be contained in the textiles and optionally no additional source of thermoplastic polymer is added to the textiles in the agglomeration zone or the melt zone of heat applied densification. If the textiles do not contain thermoplastic polymer or insufficient amount of thermoplastic polymer, a source of thermoplastic polymer can be combined with the textiles or size reduced textiles. An example of a source of thermoplastic polymer includes binder powder. Desirably, a source of thermoplastic polymer is a source of recycle plastics other than textiles, whether virgin textiles or recycle textiles ("recycle plastics"). This has the advantage of ensuring that the densified textile agglomerates have a recycle source content of 100%. The source of thermoplastic polymer can be added to the textile feed prior to size reduction, to the size reduced textiles as a feed to the densification process, or as a separate feed stream into the densification process, At least a portion of the source of recycle plastics can be from the same facility or from a part of the same separation train used to separate the textiles (that are densified) from MSW. For example, a separation facility processing MSW can separate glass, metal, plastics, and textile components from each other and isolate those components. The recycle plastics components and textile components from that facility can be combined in the densification process to provide a densified textile aggregates containing 100% recycle content. Alternatively, a separation facility processing MSW can be configured to separate a plastics and textiles as one component from an MSW stream, to further reduce the cost of mechanical separation. In each of these embodiments, the recycle plastics provide a convenient source of thermoplastic polymer as a material that both binds textiles, and in particular natural fibers, allows the agglomerate or hot melt granules to be further comminuted if desired, and provide a good source of fuel along with textiles in the gasification process.

In one embodiment or in combination with any of the mentioned embodiments, the recycle source content in the densified textile agglomerates is at least 50%, or at least 60%, or at least 70%, or at least 80%, or at least 85%, or at least 90%, or at least 92%, or at least 95%, or at least 97%, or at least 98%, or at least 99%, or at least 99.5%, or at even 100%, in each case wt. % based on the weight of the densified textile agglomerates.

If a binder is employed, it can be natural or synthetic. Any conventional thermoplastics known as binders are suitable, as well as whey (or waste whey), sugar, or ligno sulfonates (or waste lignosulfates). The binder desirably is one which can be granulated without disintegrating, and accordingly, thermoplastic textiles binders are more desirable.

In one embodiment or in combination with any of the mentioned embodiments or in any of the mentioned embodiments, the textiles or size reduced textiles are densified without combining them with a feed containing thermoplastic polymer (e.g. binder powders or recycle plastics). Some size reduced textiles contain sufficient thermoplastic textiles synthetic fibers to allow the fibers to be densified by heat energy (whether indirect by frictional energy or external application of a heat energy source) above the $T_g$ of the thermoplastic fibers in the size reduces textiles. Some size reduced textiles contain at least 25 wt. %, or at least 50 wt. %, or at least 75 wt. %, or at least 90 wt. %, or at least 95 wt. % thermoplastic textiles fibers.

In one embodiment or in combination with any of the mentioned embodiments, the median average size of the size reduced textiles in their longest dimension are smaller than the median average size of the densified textile aggregates in their longest dimension. This can be the case when the textiles are size reduced down to a fine powder and the agglomerate or hot melt particles are larger. Alternatively, the median average size of the reduced size textiles in their longest dimension are larger than the median average size of the densified textile aggregates particles.

In one embodiment or in combination with any of the mentioned embodiments, the densification step includes the application of heat or are processed by a heat-treated process. The size reduced textiles are subjected to an external source of heat energy at or above the $T_g$ of the thermoplastic polymer in the synthetic fibers contained in the size reduced fiber stream, causing the softened or melted thermoplastic textiles to flow around and bind the natural fibers and any thermoset synthetic fibers. Upon cooling, the partially or fully molten textiles are solidified into a desired shape, and optionally further granulated or pulverized to a final desired size in one or more steps), or in the final granulate shape suitable for (i) shipping to a gasification facility for further granulation to a size suitable for introducing into the gasifier or (ii) use as a feed to the gasifier without further granulation.

In one embodiment or in combination with any of the mentioned embodiments, at least a portion or all of the densified textile aggregates in the feedstock composition or stream, or the feedstock composition or stream fed to a gasifier or into the gasification zone, are obtained from textiles or contain textile fibers. In one embodiment or in combination with any of the mentioned embodiments, the densified textiles aggregates contain, or as fed to a gasifier or a feedstock to a gasifier contain, at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. %, or at least 70 wt. %, or at least 75 wt. %, or at least 80 wt. %, or at least 85 wt. %, or at least 90 wt. %, or at least 95 wt. % or at least 97 wt. % or at least 98 wt. % or at least 99 wt. % or at least 99.5 wt. % material obtained from textiles or textile fibers, based on the weight of the densified textile aggregates in the feedstock stream.

In one embodiment or in combination with any of the mentioned embodiments, which includes densified textile aggregates obtained from textiles or containing textile fibers, at least 20%, or at least 30%, or at least 50%, or at least 75%, or at least 80%, or at least 90%, or at least 95%, or at least 98% of the fibers in the textiles feedstock have an aspect ratio L:D of at least 1.5:1, or at least 1.75:1, or at least 2:1, or at least 2.25:1, or at least 2.5:1, or at least 2.75:1, or at least 3:1, or at least 3.25:1, or at least 3.5:1, or at least 3.75:1, or at least 4:1, or at least 4.5:1, or at least 5:1, or at least 5.5:1, or at least 6:1.

Non-combustible inorganic matter such as metals and minerals that prevent the densified textile aggregates from being incinerated and emitted may be contained in the densified textile aggregates for gasification. Examples include tin, cobalt, manganese, antimony, titanium, sodium, calcium, sulfur, zinc, and aluminum, their oxides and other compounds thereof may be present in the densified textile aggregates because a gasifier, and especially slagging gasifiers, are well equipped to handle minerals and metals in a feedstock. Advantageously, titanium and calcium that may be present in the densified textile aggregates can be slag modifiers.

In one embodiment or in combination with any of the mentioned embodiments, the amount of calcium compounds present in the ash densified textile aggregates is at least 30 wt. %, or at least 40 wt. %, or at least 50 wt. %, or at least 55 wt. %, or at least 60 wt. %, or at least 63 wt. %, based on the weight of densified textile aggregates ash. The upper amount is desirably not more than 90 wt. %, or not more than 80 wt. %, or not more than 75 wt. %, based on the weight of densified textile aggregates ash.

In another embodiment, the amount of sodium compounds present in the ash of densified textile aggregates is at least 2 wt. %, or at least 3 wt. %, or at least 4 wt. %, or at least 5 wt. %, or at least 6 wt. %, or at least 7 wt. %, based on the weight of the densified textile aggregates ash. The upper amount is desirably not more than 20 wt. %, or not more than 17 wt. %, or not more than 15 wt. %, based on the weight of densified textile aggregates ash.

In another embodiment, the amount of titanium compounds present in the ash of densified textile aggregates is at least 30 wt. %, or at least 40 wt. %, or at least 50 wt. %, or at least 60 wt. %, or at least 70 wt. %, or at least 75 wt. %, based on the weight of densified textile aggregates ash. The upper amount is desirably not more than 96 wt. %, or not more than 90 wt. %, or not more than 86 wt. %, based on the weight of the densified textile aggregates ash.

In another embodiment, the amount of iron compounds present in the ash of densified textile aggregates used in the feedstock is not more than 5 wt. %, or not more than 3 wt. %, or not more than 2 wt. %, or at least 1.5 wt. %, or at least 2 wt. %, based on the weight of densified textile aggregates ash.

In another embodiment, the amount of aluminum compounds present in the ash of densified textile aggregates used in the feedstock is not more than 20 wt. %, or not more than 15 wt. %, or not more than 10 wt. %, or not more than 5 wt. %, or not more than 3 wt. %, or not more than 2 wt. %, or not more than 1.5 wt. %, based on the weight of the densified textile aggregates ash.

In another embodiment, the amount of silicon compounds present in the ash of densified textile aggregates used in the feedstock is not more than 20 wt. %, or not more than 15 wt. %, or not more than 10 wt. %, or not more than 8 wt. %, or not more than 6 wt. %, based on the weight of the densified textile aggregates ash.

Desirably, the densified textile aggregates contain low levels or no halide containing polymers, in particular polyvinyl chloride, polyvinyl fluoride, polyvinylidene fluoride, and polytetrafluoroethane, and other fluorinated or chlorinated polymers, especially if the densified textile aggregates are fed to a refractory lined gasifier. The release of chlorine or fluorine elements or radicals over time can impact the longevity of refractory lining on gasifiers operating at high temperature and pressure. In one embodiment or in combination with any of the mentioned embodiments, the densified textile aggregates contain less than 10 wt. %, or not more than 8 wt. %, or not more than 6 wt. %, or not more than 5 wt. %, or not more than 4 wt. %, or not more than 3.5 wt. %, or not more than 3 wt. %, or not more than 2.5 wt. %, or not more than 2 wt. %, or not more than 1.5 wt. %, or not more than 1 wt. %, or not more than 0.5 wt. %, or not more than 0.25 wt. %, or not more than 0.1 wt. %, or not more than 0.05 wt. %, or not more than 0.01 wt. %, or not more than 0.005 wt. %, or not more than 0.001 wt. %, or not more than 0.0005 wt. %, or not more than 0.0001 wt. %, or not more than 0.00005 wt. % halide containing polymers, based on the weight of the densified textile aggregates. Desirably, the halide minimized or excluded is chlorine or fluorine.

In one embodiment or in combination with any mentioned embodiments, the densified textile aggregates (those ground to the final size as combined into the feedstock composition) are desirably not pyrolyzed or torrefied prior to their introduction into the gasifier, and desirably, the densified textile aggregates are not obtained from a source of textiles which have been pyrolyzed or torrefied.

In another embodiment, the densified textile aggregates, once made, are not thereafter melted or extruded prior to their entry into the gasifier. In another embodiment, the densified textile aggregates are not melted or extruded or do not receive a pyrolysis thermal treatment, or do not receive a thermal treatment above 225° C., or above 210° C., or above 200° C., or above 195° C., or above 190° C., or above 175° C., or above 160° C., or above 150° C., or above 140° C., or above 130° C., or above 120° C., or above 110° C., or above 100° C., or above 90° C., or above 80° C., or above 60° C., or above 58° C. or above their nominal temperature at their ambient conditions prior to their introduction into the gasification zone. It is to be noted that the densified textile aggregates can be dried before their introduction into the solid fossil fuel feedstock composition, however, this would not be necessary in a slurry-based feedstock composition such as in water, or a petroleum-based oil, hydrocarbon or oxygenated hydrocarbon fuel feedstock.

There is also provided a circular manufacturing process comprising:

1. providing a recycle textile, and 2. densifying said recycle textile to form a densified textile aggregates, and 3. gasifying said densified textile aggregates to produce a recycle textile derived syngas, and 4. either (i) reacting said recycle textile derived syngas to make a recycle content intermediate, polymer, or article (Recycle PIA) each of which have their origin at least in part to said recycle textile derived syngas or (ii) assigning a recycle content allotment, obtained from said recycle textile, to an intermediate, polymer, or article to produce a Recycle PIA; and 5. optionally, taking back at least a portion of said Recycle PIA as a feedstock to said gasification process step (i), or (ii), or (iii).

In the above described process, an entirely circular or closed loop process is provided in which textiles can be recycled multiple times to make the same family or classification of textiles.

Examples of articles that are included in PIA are fibers, yarns, tow, continuous filaments, staple fibers, rovings, fabrics, textiles, flake, sheet, compounded sheet, and consumer articles.

In this or in combination with any of the mentioned embodiments, the allotment can be assigned to an intermediate, polymer, or article to produce a Recycle PIA directly from a recycle content value taken from the recycle textile or densified textile aggregates or from the step of gasifying a feedstock containing a fossil fuel and densified textile aggregates, or the allotment can be assigned to the intermediate, polymer, or article to product a recycle PIA indirectly by assigning the recycle content value taken from a recycle inventory into which recycle content value is deposited from the recycle content present in the recycle textile or in the densified textile aggregates or the step of gasifying a feedstock containing a fossil fuel and densified textile aggregates.

In one embodiment, the Recycle PIA is a polymer or article (e.g. fiber) of the same family or classification of polymers or articles (e.g. fibers) contained in or one the recycle textile used in step (i).

In one embodiment, a Recycle PIA can be made by a process in which densified textile aggregates are gasified according to any of the processes described herein.

There is also provided a circular manufacturing process comprising:

1. a manufacturer of syngas, or one among its Family of Entities, or an entity contracted with either of them (collectively the "Recipient"), receiving recycle textiles (whether postindustrial or post-consumer), optionally and desirably from an industrial supplier of said articles (e.g. textiles) or fibers contained in or on said textile, and 2. one or more of the Recipients size reducing said textile or fibers to make a densified textile aggregates, and

3. one or more of the Recipients gasifying said densified textile aggregates to produce a recycle textile derived syngas, and 4. either (i) reacting said recycle textile derived syngas to make a recycle content intermediate, polymer, or article (Recycle PIA) each of which have their origin at least in part to said recycle textile derived syngas or (ii) assigning a recycle content allotment, obtained from said recycle textile or said densified textile aggregates, to an intermediate, polymer, or article to thereby produce a Recycle PIA; and 5. optionally, furnishing at least a portion of said Recycle PIA to said industrial supplier, or to an entity contracted with said industrial supplier or with one among the Family of Entities of the industrial supplier for the supply of said Recycle PIA or an article made with said Recycle PIA.

In this or in combination with any of the mentioned embodiments, the allotment can be assigned to an intermediate, polymer, or article to produce a Recycle PIA directly from a recycle content value taken from the recycle textile or densified textile aggregates or from the step of gasifying a feedstock containing a fossil fuel and recycle textiles or densified textile aggregates, or the allotment can be assigned to the intermediate, polymer, or article to product a recycle PIA indirectly by assigning the recycle content value taken from a recycle inventory into which recycle content value is deposited from the recycle content present in the recycle textile or in the densified textile aggregates or the step of gasifying a feedstock containing a fossil fuel and densified textile aggregates.

In the above described process, an entirely circular or closed loop process is provided in which textiles can be recycled multiple times to make the same family or classification of textiles. The industrial supplier may furnish a processor entity with the textile or articles containing the textile to process those textiles or articles into a form suitable or more suitable for gasification as further described herein to make densified textile aggregates, and in turn, the processor entity supplies the densified textile aggregates or precursors thereof to the manufacturer of syngas or one among its Family of Entities who can either feed to densified textile aggregates as such to a feedstock stream to a gasifier, or can further process the precursors or densified textile aggregates into a final size suitable for gasification by any suitable process, such as pulverization or grinding. The gasification processes, equipment, and designs used can be any of those mentioned herein. The syngas made using feedstocks containing the densified textile aggregates can then either by converted through a reaction scheme to make Recycle PIA, or the allotments created by such gasification step or obtained from the recycle textiles or densified textile aggregates can be stored in an inventory of allotments, and from the inventory of allotments from any source, a portion thereof can be withdrawn and assigned to an intermediate, polymer or article to make Recycle PIA. To close the circularity of the textile, at least a portion of the Recycle PIA can by furnished to the supplier of the textiles, or it can be supplied to any entity contracted with the supplier to process the Recycle PIA into a different form, different size, or to combine with other ingredients or textiles (e.g. compounders and/or sheet extruders), or to make articles containing the PIA, for supply to or on behalf of the supplier. The Recycle PIA furnished to the industrial supplier or one of its contracted entities is desirably in the same family or type of textile as the textile or article containing the textile was supplied by the industrial supplier to the Recipient.

A "recycle content allotment" or "allotment" means a recycle content value that is:

a. transferred from a recycle waste (which is any recycle waste stream whether or not it contains recycle textiles) to a receiving composition (e.g., compound, polymer, article, intermediate, feedstock, product, or stream) that may or may not have a physical component that is traceable to the recycle waste; or b. deposited into a recycle inventory at least a portion of which originates from recycle waste.

An allotment can be an allocation or a credit. A recycle waste is any one of waste streams identified throughout this disclosure, including the size reduced textiles, densified textiles, the textiles from which they originate, or the feedstock composition containing the densified textiles.

The recycle content value (whether by mass or percentage or any other unit of measure) can optionally be determined according to a standard system for tracking, allocating, and/or crediting recycle content among various compositions.

A "recycle content value" is a unit of measure representative of a quantity of material having its origin in recycle textile or densified textile aggregates. The recycle content value can have its origin in any type of recycled textile or any recycle textile processed in any type of process before being gasified.

The particular recycle content value can be determined by a mass balance approach or a mass ratio or percentage or any other unit of measure and can be determined according to any system for tracking, allocating, and/or crediting recycle content among various compositions. A recycle content value can be deducted from a recycle inventory and applied to a product or composition to attribute recycle content to the product or composition. A recycle content value does not have to originate from gasifying recycle textile, and can be a unit of measure having its known or unknown origin in any technology used to process recycle textile. In one embodiment, at least a portion of the recycle textiles from which an allotment is obtained is also gasified as described throughout the one or more embodiments herein; e.g. combined with a fossil fuel and subjected to gasification.

In one embodiment, at least a portion of the recycle content allotment or allotment or recycle value deposited into a recycle content inventory is obtained from recycle textile or densified textile aggregates. Desirably, at least 60%, or at least 70%, or at least 80%, or at least 90% or at least 95%, or up to 100% of the:

a. allotments or b. deposits into the recycle inventory, or c. recycle content value in the recycle inventory, or d. recycle content value applied to compositions to make Recycle PIA are obtained from recycle textile or densified textile aggregates.

A recycle content allotment can include a recycle content allocation or a recycle content credit obtained with the transfer or use of a raw material. In one embodiment or in combination with any of the mentioned embodiments, the polymer, intermediate, composition, article or stream receiving the recycle content allotment can be or contain a portion of a non-recycle composition (e.g., compound, polymer, feedstock, product, or stream). A "non-recycle" means a composition (e.g., compound, polymer, feedstock, product, or stream) none of which was directly or indirectly derived from recycled waste of any kind, including textile.

A "recycle content allocation" and "allocation" mean a type of recycle content allotment, where the entity or person supplying a composition sells or transfers the composition to the receiving person or entity, and the person or entity that made the composition has an allotment at least a portion of which can be associated with the composition sold or transferred by the supplying person or entity to the receiving person or entity. The supplying entity or person can be controlled by the same entity or person(s) or a variety of affiliates that are ultimately controlled or owned at least in part by a parent entity ("Family of Entities"), or they can be from a different Family of Entities. Generally, a recycle content allocation travels with a composition and with the downstream derivates of the composition. An allocation may be deposited into a recycle inventory and withdrawn from the recycle inventory as an allocation and applied to a composition to make a Recycle PIA.

A "recycle content credit" and "credit" mean a type of recycle content allotment, where the allotment is available for sale or transfer or use, or is sold or transferred or used, either:

a. without the sale of a composition, or b. with the sale or transfer of a composition but the allotment is not associated the sale or transfer of the composition, or c. is deposited into or withdrawn from a recycle inventory that does not track the molecules of a recycle content feedstock to the molecules of the resulting compositions which were made with the recycle content feedstocks, or which does have such tracking capability but which did not track the particular allotment as applied to a composition.

In one embodiment or in combination with any of the mentioned embodiments, an allotment may be deposited into a recycle inventory, and a credit may be withdrawn from the inventory and applied to a composition to make a Recycle PIA. This would be the case where an allotment is created from a recycle textile and deposited into a recycle inventory, and deducting a recycle content value from the recycle inventory and applying it to a composition to make a Recycle PIA that either has no portion originating from syngas or does have a portion originating from syngas but such syngas making up the portion of the composition was not a recycle content syngas. In this system, one need not trace the source of a reactant compound or composition back to the manufacture of densified textile derived syngas stream or back to any atoms contained in the densified textile derived syngas stream, but rather can use any reactant compound or composition made by any process and have associated with such reactant compound or composition, or have associated with the Recycle PIA, a recycle content allotment. In an embodiment, the Recycle PIA reactants (the compositions used to make Recycle PIA or the compositions to which an allotment is applied) do not contain recycle content.

In one embodiment, the composition receiving an allotment to make a Recycle PIA originates in part from a syngas stream obtained by any gasification process. The feedstock to the gasification process may optionally contain fossil fuel such as coal. The feedstock may optionally also contain a combination of fossil fuel and recycle textiles or densified textile aggregates. In one embodiment, there is provided a process in which:

a. a recycle textile is obtained, b. a recycle content value (or allotment) is obtained from the recycle textile, and i. deposited into a recycle inventory, and an allotment (or credit) is withdrawn from the recycle inventory and applied to a composition to obtain a Recycle PIA, or ii. applied to a composition to obtain a Recycle PIA; and c. at least a portion of the recycle textile is subjected to a gasification process, optionally by combining it with a fossil fuel as a feedstock to a gasifier, optionally according to any of the designs or processes described herein; and d. optionally at least a portion of the composition in step b. originates from a syngas stream, optionally the syngas stream having been obtained by any of the feedstocks and methods described herein.

The steps b. and c. do not have to occur simultaneously. In one embodiment, they occur within a year of each other, or within six (6) months of each other, or within three (3) months of each other, or within one (1) month of each other, or within two (2) weeks of each other, or within one (1) week of each other, or within three (3) days of each other. The process allows for a time lapse between the time an entity or person receiving the recycle textile and creating the allotment (which can occur upon receipt or ownership of the recycle textile) and the actual processing of the recycle textile in a gasifier.

As used herein, "recycle inventory" and "inventory" mean a group or collection of allotments (allocations or credits) from which deposits and deductions of allotments in any units can be tracked. The inventory can be in any form (electronic or paper), using any or multiple software programs, or using a variety of modules or applications that together as a whole tracks the deposits and deductions. Desirably, the total amount of recycle content withdrawn (or applied to the Recycle PIA) does not exceed the total amount of recycle content allotments or credits on deposit in the recycle inventory (from any source, not only from gasification of recycle textiles). However, if a deficit of recycle content value is realized, the recycle content inventory is rebalanced to achieve a zero or positive recycle content value available. The timing for rebalancing can be either determined and managed in accordance with the rules of a particular system of accreditation adopted by the densified textile derived syngas manufacturer or by one among its Family of Entities, or alternatively, is rebalanced within one (1) year, or within six (6) months, or within three (3) months, or within one (1) month of realizing the deficit. The timing for depositing an allotment into the recycle inventory, applying an allotment (or credit) to a composition to make a Recycle PIA, and gasifying a recycle textile, need not be simultaneous or in any particular order. In one embodiment, the step of gasifying a particular volume of recycle textiles occurs after the recycle content value or allotment from that volume of recycle textile is deposited into a recycle inventory. Further, the allotments or recycle content values withdrawn from the recycle inventory need not be traceable to recycle textiles or gasifying recycle textiles, but rather can be obtained from any waste recycle stream, and from any method of processing the recycle waste stream. Desirably, at least a portion of the recycle content value in the recycle inventory is obtained from recycle textiles, and optionally at least a portion of recycle textiles are processed in the one or more gasification processes as described herein, optionally within a year of each other and optionally at least a portion of the volume of recycle textiles from which a recycle content value is deposited into the recycle inventory is also processed by any or more of the gasification processes described herein.

The determination of whether a Recycle PIA is derived directly or indirectly from recycled waste is not on the basis of whether intermediate steps or entities do or do not exist in the supply chain, but rather whether at least a portion of the recycle textile molecules fed to the gasifier can be traced into a Recycle PIA. The Recycle PIA is considered to be directly derived from recycle textile or have direct contact with recycle textile if at least a portion of the molecules in the Recycle PIA can be traced back, optionally through one or more intermediate steps or entities, to at least a portion of the densified textile derived syngas molecules. Any number of intermediaries and intermediate derivates can be made before the Recycle PIA is made.

A Recycle PIA can be indirectly derived from recycled textiles if no portion of its molecules are obtained from densified textile derived syngas molecules or some portion of is molecules are obtained from densified textile derived syngas molecules but the Recycle PIA has a recycle content value that exceeds the recycle content value associated with the densified textile derived syngas molecules, and in this latter case, a Recycle PIA can be both directly and indirectly derived from recycle textile.

In one embodiment or in combination with any of the mentioned embodiments, the Recycle PIA is indirectly derived from recycle textile or recycle content syngas. In another embodiment, the Recycle PIA is directly derived from recycle textile or recycle content syngas. In another embodiment, the Recycle PIA is indirectly derived from recycle textile or densified textile derived syngas and no portion of the Recycle PIA is directly derived from the recycle textile or recycle content syngas.

In another embodiment, there is provided a variety of methods for apportioning the recycle content among the various Recycle PIA compositions made by any one entity or a combination of entities among the Family of Entities of which the densified textile derived syngas manufacturer is a part. For example, the densified textile derived syngas manufacturer, of any combination or the entirety of its Family of Entities, or a Site, can:

a. adopt a symmetric distribution of recycle content values among its product(s) based on the same fractional percentage of recycle content in one or more feedstocks, or based on the amount of allotment received. For example, if 5 wt. % of the gasification feedstock is densified textile aggregates, or if the recycle content value is 5 wt. % of the entire gasifier feedstock, then all Recycle PIA compositions may contain 5 wt. % recycle content value. In this case, the amount of recycle content in the products is proportional to the amount of recycle content in the feedstock to make the products; or b. adopt an asymmetric distribution of recycle content values among its product(s) based on the same fractional percentage of recycle content in the one or more feedstocks, or based on the amount of allotment received. For example, if 5 wt. % of the gasifier feedstock is recycle textile, or if the allotment value is 5 wt. % of the entire gasifier feedstock, then one volume or batch of Recycle PIA can receive a greater amount of recycle content value that other batches or volume of Recycle PIA. One batch of PVA can contain 20% recycle content by mass, and another batch can contain zero 0% recycle content, even though both volumes may be compositionally the same, provided that the amount of recycle content value withdrawn from a recycle inventory and applied to the Recycle PIA does not exceed the amount of recycle content value deposited into the recycle inventory, or if a deficit is realized, the overdraft is rebalanced to zero or a positive credit available status as described above. In the asymmetric distribution of recycle content, a manufacturer can tailor the recycle content to volumes of Recycle PIA sold as needed among customers, thereby providing flexibility among customers some of whom may need more recycle content than others in a PVA volume.

Both the symmetric distribution and the asymmetric distribution of recycle content can be proportional on a Site wide basis, or on a multi-Site basis. In one embodiment or in combination with any of the mentioned embodiments, the recycle content input (recycle textiles or allotments) can be within a Site, and recycle content values from said inputs are applied to one or more compositions made at the same Site to make Recycle PIA. The recycle content values can be applied symmetrically or asymmetrically to one or more different compositions made at the Site.

In one embodiment or in combination with any of the mentioned embodiments, the recycle content input or creation (recycle content feedstock or allotments) can be to or at a first Site, and recycle content values from said inputs are transferred to a second Site and applied to one or more compositions made at a second Site. The recycle content values can be applied symmetrically or asymmetrically to the compositions at the second Site.

In an embodiment, the Recycle PIA has associated with it, or contains, or is labelled, advertised, or certified as containing recycle content in an amount of at least 0.01 wt. %, or at least 0.05 wt. %, or at least 0.1 wt. %, or at least 0.5 wt. %, or at least 0.75 wt. %, or at least 1 wt. %, or at least 1.25 wt. %, or at least 1.5 wt. %, or at least 1.75 wt. %, or at least 2 wt. %, or at least 2.25 wt. %, or at least 2.5 wt. %, or at least 2.75 wt. %, or at least 3 wt. %, or at least 3.5 wt. %, or at least 4 wt. %, or at least 4.5 wt. %, or at least 5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. % and/or the amount can be up to 100 wt. %, or up to 95 wt. %, or up to 90 wt. %, or up to 80 wt. %, or up to 70 wt. %, or up to 60 wt. %, or up to 50 wt. %, or up to 40 wt. %, or up to 30 wt. %, or up to 25 wt. %, or up to 22 wt. %, or up to 20 wt. %, or up to 18 wt. %, or up to 16 wt. %, or up to 15 wt. %, or up to 14 wt. %, or up to 13 wt. %, or up to 11 wt. %, or up to 10 wt. %, or up to 8 wt. %, or up to 6 wt. %, or up to 5 wt. %, or up to 4 wt. %, or up to 3 wt. %, or up to 2 wt. %, or up to 1 wt. %, or up to 0.9 wt. %, or up to 0.8 wt. %, or up to 0.7 wt. %. The recycle content associated with the Recycle PIA can be associated by applying an allotment (credit or allocation) to any polymer and/or article made or sold. The allotment can be contained in an inventory of allotments created, maintained or operated by or for the Recycle PIA manufacturer. The allotment can be obtained from any source along any manufacturing chain of products provided that its origin is in gasifying a feedstock containing a fossil fuel and densified textile aggregates.

The amount of recycle content in a reactant compound or composition, or the amount of recycle content applied to the Recycle PIA, or the amount of densified textile aggregates needed to feed the gasifier to claim a desired amount of recycle content in the Recycle PIA in the event that all the recycle content from the recycle textile feedstock is applied to the Recycle PIA, can be determined or calculated by any of the following methods:

(i) the amount of an allotment associated with the Recycle PIA is determined by the amount certified or declared by the supplier of transferred Recycle PIA, or (ii) the amount of allotment declared by the entity using Recycle PIA, or (iii) using a mass balance approach to back-calculate the minimum amount of recycle content in the feedstock from an amount of recycle content declared, advertised, or accounted for by the manufacturer, whether or not accurate, as applied to the Recycle PIA product, (iv) blending of non-recycle content with densified textile aggregates feedstock, or associating recycle content to a portion of the feedstock, using pro-rata mass approach In one embodiment, the Recycle PIA manufacturer can make Recycle PIA, or process a reactant compound or composition and make a Recycle PIA, or make Recycle PIA by obtaining any source of a reactant compound or composition from a supplier, whether or not such reactant compound or composition has any recycle content, and either:

i. from the same supplier of the reactant compound or composition, also obtain a recycle content allotment applied to either syngas or to any product, article, polymer, or composition, or ii. from any person or entity, obtaining a recycle content allotment without a supply of a reactant compound or composition from said person or entity transferring said recycle content allotment.

The allotment in (i) can be obtained from a supplier of the reactant compound or composition used to make Recycle PIA, and the supplier also supplies and transfers the reactant compound or composition to the Recycle PIA manufacturer or within its Family of Entities. The circumstance described in (i) allows a Recycle PIA manufacturer to obtain a supply of a reactant compound or composition that has non-recycle content, yet obtain a recycle content allotment from the reactant compound or composition. In one embodiment, the reactant compound or composition supplier transfers a recycle content allotment to the Recycle PIA manufacturer as well as a supply of reactant compound or composition to the Recycle PIA manufacturer, where the recycle content allotment is not associated with the reactant compound or composition supplied, provided that the recycle content allotment transferred has its origins in gasifying recycle densified textile aggregates. The recycle content allotment does not have to be tied to an amount of recycle content in a reactant compound or composition or to any monomer used to make Recycle PIA, but rather the recycle content allotment transferred by the reactant compound or composition supplier can be associated with other products having their origin in a densified textile derived syngas stream other than those in a reaction scheme to make polymer and/or articles. This allows flexibility among the reactant compound or composition supplier and Recycle PIA manufacturer to apportion a recycle content among the variety of products they each make. In each of these cases, however, the recycle content allotment has its origins in gasifying recycle textiles.

In one embodiment, the reactant compound or composition supplier transfers a recycle content allotment to the Recycle PIA manufacturer and a supply of reactant compound or composition to the Recycle PIA manufacturer, where the recycle content allotment is associated with reactant compound or composition. Optionally, the reactant compound or composition being supplied can be derived from recycle textile feedstock and at least a portion of the recycle content allotment being transferred can be the recycle content in the reactant compound or composition. The recycle content allotment transferred to the Recycle PIA manufacturer can be up front with the reactant compound or composition supplied, optionally in installments, or with each reactant compound or composition portion supplier, or apportioned as desired among the parties.

The allotment in (ii) is obtained by the Recycle PIA manufacturer (or its Family of Entities) from any person or entity without obtaining a supply of reactant compound or composition from the person or entity. The person or entity can be a reactant compound or composition manufacturer that does not supply reactant compound or composition to the Recycle PIA manufacturer or its Family of Entities, or the person or entity can be a manufacturer that does not make a reactant compound or composition. In either case, the circumstances of (ii) allows a Recycle PIA manufacturer to obtain a recycle content allotment without having to purchase any reactant compound or composition from the entity supplying the recycle content allotment. For example, the person or entity may transfer a recycle content allotment through a buy/sell model or contract to the Recycle PIA manufacturer or its Family of Entities without requiring purchase or sale of an allotment (e.g. as a product swap of products that are not reactant compound or composition), or the person or entity may outright sell the allotment to the Recycle PIA manufacturer or one among its Family of Entities. Alternatively, the person or entity may transfer a product, other than a reactant compound or composition, along with its associated recycle content allotment to the Recycle PIA manufacturer. This can be attractive to a Recycle PIA manufacturer that has a diversified business making a variety of products other than Recycle PIA requiring raw materials other than a reactant compound or composition that the person or entity can supply to the Recycle PIA manufacturer.

The allotment can be deposited into a recycle inventory (e.g. an inventory of allotments). In one embodiment, the allotment is an allotment created by the manufacturer of the densified textile derived syngas stream. The Recycle PIA manufacturer can also make a polymer and/or article, whether or not a recycle content is applied to the polymer and/or article and whether or not recycle content, if applied to the polymer and/or article, is drawn from the inventory. For example, either the densified textile derived syngas stream manufacturer and/or the Recycle PIA manufacturer may:

a. deposit the allotment into an inventory and merely store it; or b. deposit the allotment into an inventory and apply allotments from the inventory to products other than:

i. any products derived directly or indirectly from the densified textile derived syngas stream, or ii. to a polymer and/or articles made by the Recycle PIA manufacturer, or c. sell or transfer an allotment from the inventory into which at least one allotment, obtained as noted above, was deposited.

If desired, however, from that inventory, any recycle content allotment can be deducted in any amount and applied to a polymer and/or article to make a Recycle PIA. For example, a Recycle inventory of allotments can be generated having a variety of sources for creating the allotments. Some recycle content allotments (credits) can have their origin in methanolysis of recycle waste, or from mechanical recycling of waste textile or metal recycling, and/or from pyrolyzing recycle waste, or from any other chemical or mechanical recycling technology. The recycle inventory may or may not track the origin or basis of obtaining a recycle content value, or the inventory may not allow one to associate the origin or basis of an allotment to the allotment applied to Recycle PIA. It is sufficient that an allotment is deducted from an allotment inventory and applied to Recycle PIA regardless of the source or origin of the allotment, provided that a recycle content allotment derived from a recycle textile feedstock containing a fossil fuel and densified textile aggregates is present in the allotment inventory as the time of withdrawal, or a recycle content allotment is obtained by the Recycle PIA manufacturer as specified in step (i) or step (ii), whether or not that recycle content allotment is actually deposited into the inventory. In one embodiment, the recycle content allotment obtained in step (i) or (ii) is deposited into an inventory of allotments. In one embodiment, the recycle content allotment deducted from the inventory and applied to the Recycle PIA originates from recycle textiles or densified textile aggregates, whereby the densified textile aggregates are ultimately gasified with a fossil fuel.

As used throughout, the inventory of allotments can be owned by the densified textile derived syngas manufacturer, or by the Recycle PIA manufacturer, or operated by either of them, or owned or operated by neither but at least in part for the benefit of either of them, or licensed by either of them. Also, as used throughout, the densified textile derived syngas manufacturer or the Recycle PIA manufacturer may also include either of their Family of Entities. For example, while either of them may not own or operate the inventory, one among its Family of Entities may own such a platform, or license it from an independent vendor, or operate it for either of them. Alternatively, an independent entity may own and/or operate the inventory and for a service fee operate and/or manage at least a portion of the inventory for either of them.

In one embodiment, the Recycle PIA manufacturer obtains a supply of reactant compound or composition from a supplier, and also obtains an allotment from the supplier, where such allotment is derived from gasifying a feedstock containing a fossil fuel and densified textile aggregates, and optionally the allotment is associated with the reactant compound or composition supplied. In one embodiment, at least a portion of the allotment obtained by the Recycle PIA manufacturer is either:

a. applied to Recycle PIA made by the supply of reactant compound or composition;

b. applied to Recycle PIA not made by the supply of reactant compound or composition, such as would be the case where Recycle PIA is already made and stored in inventory or future made Recycle PIA; or c. deposited into an inventory from which is deducted an allotment applied to Recycle PIA (the Recycle PIA applied allotment) and the deposited allotment either does, or does not, contribute to the amount of allotments from which the Recycle PIA applied allotment is drawn.

d. deposited into an inventory and stored.

It is not necessary in all embodiments that recycle textile feedstock is used to make Recycle PIA composition or that the Recycle PIA was obtained from a recycle content allotment associated with a reactant compound or composition. Further, it is not necessary that an allotment be applied to the recycle textile feedstock for making the Recycle PIA to which recycle content is applied. Rather, as noted above, the allotment, even if associated with a reactant compound or composition when the reactant compound or composition is obtained, can be deposited into an electronic inventory. In one embodiment, however, the reactant compound or composition associated with the allotment is used to make the Recycle PIA compound or composition. In one embodiment, the Recycle PIA is obtained from a recycle content allotment associated with densified textile aggregates, or with gasifying densified textile aggregates. In one embodiment, at least a portion of the allotments obtained from recycle textile made into densified textile aggregates, or the densified textile aggregates, or gasifying densified textile aggregates are applied to Recycle PIA to make a Recycle PIA.

In one embodiment, the densified textile derived syngas stream manufacturer generates an allotment by gasifying a combination of a fossil fuel and densified textile aggregates, and either:

a. applies the allotment to any compound or composition (whether liquid or solid or polymer in any form, including pellets, sheet, fibers, flake, etc.) made directly or indirectly (e.g. through a reaction scheme of several intermediates) from the densified textile derived syngas stream; or b. applies the allotment to a compound or composition not made directly or indirectly from the densified textile derived syngas stream, such as would be the case where reactant compounds or compositions are already made and stored in inventory or future made non-recycle content reactant compounds or compositions; or c. deposited into an inventory from which is deducted any allotment that is applied to reactant compounds or compositions; and the deposited allotment either is or is not associated with the particular allotment applied to the reactant compounds or compositions; or d. is deposited into an inventory and stored for use at a later time.

In any of the embodiments described throughout, the timing for taking the allotment, or depositing the allotment into a recycle inventory, can be as early as when a recycle textile is received or owned by a Recipient or one among its Family of Entities, or when it is converted to a densified textile aggregates, or when a Recipient or one among its Family of Entities receives or owns densified textile aggregates, or when they are combined with a fossil fuel, or when gasified, or when a densified textile derived syngas is made. For clarification, an allotment is deemed generated or obtained by or originating from gasifying densified textile aggregates even though the timing of taking or recognizing the allotment is earlier or later than the actual time the densified textile aggregates are gasified, provided that the densified textile aggregates are subjected to gasification.

There is now also be provided a package or a combination of a Recycle PIA and a recycle content identifier associated with Recycle PIA, where the identifier is or contains a representation that the Recycle PIA contains, or is sourced from or associated with a recycle content. The package can be any suitable package for containing a polymer and/or article, such as a drum, railroad car, isotainer, totes, polytote, bale, IBC totes, compressed bale, jerrican, polybag, spools, roving, winding, or cardboard packaging. The identifier can be a certificate document, a product specification stating the recycle content, a label, a logo or certification mark from a certification agency representing that the article or package contains contents or the Recycle PIA contains, or is made from sources or associated with recycle content, or it can be electronic statements by the Recycle PIA manufacturer that accompany a purchase order or the product, or posted on a website as a statement, representation, or a logo representing that the Recycle PIA contains or is made from sources that are associated with or contain recycle content, or it can be an advertisement transmitted electronically, by or in a website, by email, or by television, or through a tradeshow, in each case that is associated with Recycle PIA. The identifier need not state or represent that the recycle content is derived from gasifying a feedstock containing a fossil fuel and densified textile aggregates. Rather, the identifier can merely convey or communicate that the Recycle PIA has or is sourced from a recycle content, regardless of the source. However, the Recycle PIA has a recycle content allotment that, at least in part, originates from gasifying densified textile aggregates.

In one embodiment, one may communicate recycle content information about the Recycle PIA to a third party where such recycle content information is based on or derived from at least a portion of the allocation or credit. The third party may be a customer of the densified textile derived syngas manufacturer or Recycle PIA manufacturer or supplier, or may be any other person or entity or governmental organization other than the entity owning the either of them. The communication may electronic, by document, by advertisement, or any other means of communication.

In one embodiment, there is provided a system or package comprising:

a. Recycle PIA or article made thereby, and b. an identifier such as a credit, label or certification associated with said Recycle PIA or article made thereby, where the identifier is a representation that the polymer and/or article or article made thereby has, or is sourced from, a recycle content provided that the Recycle PIA or article made thereby has an allotment, or is made from a reactant compound or composition, at least in part originating directly or indirectly from gasifying fossil fuels and densified textile aggregates.

The system can be a physical combination, such as package having at least Recycle PIA as its contents and the package has a label, such as a logo, that the contents such as the Recycle PIA has or is sourced from a recycle content. Alternatively, the label or certification can be issued to a third party or customer as part of a standard operating procedure of an entity whenever it transfers or sells Recycle PIA having or sourced from recycle content. The identifier does not have to be physically on the Recycle PIA or on a package, and does not have to be on any physical document that accompanies or is associated with the Recycle PIA. For example, the identifier can be an electronic credit transferred electronically by the Recycle PIA manufacturer to a customer in connection with the sale or transfer of the Recycle PIA product, and by sole virtue of being a credit, it is a representation that the Recycle PIA has recycle content. The identifier itself need only convey or communicate that the Recycle PIA has or is sourced from a recycle content, regardless of the source. In one embodiment, articles made from the Recycle PIA may have the identifier, such as a stamp or logo embedded or adhered to the article. In one embodiment, the identifier is an electronic recycle content credit from any source. In one embodiment, the identifier is an electronic recycle content credit having its origin in gasifying a feedstock containing a fossil fuel and densified textile aggregates.

The Recycle PIA is made from a reactant compound or composition, whether or not the reactant is a recycle content reactant (recycle textile feedstock). Once a Recycle PIA composition is made, it can be designated as having recycle content based on and derived from at least a portion of the allotment, again whether or not the recycle textile feedstock is used to make the Recycle PIA composition. The allotment can be withdrawn or deducted from inventory. The amount of the deduction and/or applied to the Recycle PIA can correspond to any of the methods described above, e.g. a mass balance approach.

In an embodiment, a Recycle PIA compound or composition can be made by having an inventory of allotments, and reacting a reactant compound or composition a synthetic process to make a Recycle PIA, and applying a recycle content to that Recycle PIA to thereby obtain a Recycle PIA by deducting an amount of allotment from an inventory of allotments. A Recycle PIA manufacturer may have an inventory of allotments by itself or one among its Family of Entities owning, possessing, or operating the inventory, or a third party operating at least a portion of the inventory for the Recycle PIA manufacturer or its Family of Entities or as a service provided to the Recycle PIA manufacturer or one among its Family of Entities. The amount of allotment deducted from inventory is flexible and will depend on the amount of recycle content applied to the Recycle PIA. It should be at least sufficient to correspond with at least a portion if not the entire amount of recycle content applied to the Recycle PIA. The method of calculation can be a mass balance approach, or the methods of calculation described above. The inventory of allotments can be established on any basis and may be a mix of basis, provided that at least some amount of allotment in the inventory is attributable to gasifying a feedstock containing a fossil fuel and densified textile aggregates. The recycle content allotment applied to the Recycle PIA does not have to have its origin in gasifying a feedstock containing a fossil fuel and densified textile aggregates, and instead can have its origin in any other method of generating allotments from recycle waste, such as through methanolysis or gasification of recycle waste, provided that the inventory of allotments also contains an allotment or has an allotment deposit having its origin in gasifying a feedstock containing a fossil fuel and densified textile aggregates. In one embodiment, however, the recycle content applied to the Recycle PIA is an allotment obtained from gasifying a feedstock containing at least densified textile aggregates.

The following are examples of designating or declaring a recycle content to Recycle PIA or a recycle content to a reactant compound or composition:

1. A Recycle PIA manufacturer applies at least a portion of an allotment to a polymer and/or article composition where the allotment is associated with a densified textile derived syngas stream, and the reactant compound or composition used to make the Recycle PIA did not contain any recycle content or it did contain recycle content; or
  2. A Recycle PIA manufacturer applies at least a portion of an allotment to a polymer and/or article composition where the allotment is derived directly or indirectly with a recycle content reactant compound or composition, whether or not such reactant compound or composition volume is used to make the Recycle PIA; or
  3. A Recycle PIA manufacturer applies at least a portion of an allotment to a Recycle PIA composition where the allotment is derived directly or indirectly from a recycle textile feedstock used to make the Recycle PIA to which the allotment is applied, and:

a. all of the recycle content in the recycle textile feedstock is applied to determine the amount of recycle content in the Recycle PIA, or
  b. only a portion of the recycle content in the recycle textile feedstock is applied to determine the amount of recycle content applied to the Recycle PIA, the remainder stored in inventory for use to future Recycle PIA, or for application to other existing Recycle PIA made from recycle textile feedstock not containing any recycle content, or to increase the recycle content on an existing Recycle PIA, or a combination thereof, or
  c. none of the recycle content in the recycle textile feedstock is applied to the Recycle PIA and instead is stored in an inventory, and a recycle content from any source or origin is deducted from the inventory and applied to Recycle PIA; or
  4. A Recycle PIA manufacturer applies at least a portion of an allotment to a reactant compound or composition used to make a Recycle PIA to thereby obtain a Recycle PIA, where the allotment was obtained with the transfer or purchase of the same reactant compound or composition used to make the Recycle PIA and the allotment is associated with the recycle content in a reactant compound or composition; or
  5. A Recycle PIA manufacturer applies at least a portion of an allotment to a reactant compound or composition used to make a Recycle PIA to thereby obtain a Recycle PIA, where the allotment was obtained with the transfer or purchase of the same reactant compound or composition used to make the Recycle PIA and the allotment is not associated with the recycle content in a reactant compound or composition but rather on the recycle content of a monomer used to make the reactant compound or composition; or
  6. A Recycle PIA manufacturer applies at least a portion of an allotment to a reactant compound or composition used to make a Recycle PIA to thereby obtain a Recycle PIA, where the allotment was not obtained with the transfer or purchase of the reactant compound or composition and the allotment is associated with the recycle content in the reactant compound or composition; or
  7. A Recycle PIA manufacturer applies at least a portion of an allotment to a reactant compound or composition used to make a Recycle PIA to thereby obtain a Recycle PIA, where the allotment was not obtained with the transfer or purchase of the reactant compound or composition and the allotment is not associated with the recycle content in the reactant compound or composition but rather with the recycle content of any monomers used to make the reactant compound or composition; or
  8. a Recycle PIA manufacturer obtains an allotment having it origin in gasifying a feedstock containing a fossil fuel and densified textile aggregates, and:
  a. no portion of the allotment is applied to a reactant compound or composition to make Recycle PIA and at least a portion is applied to Recycle PIA to make a Recycle PIA; or
  b. less than the entire portion is applied to a reactant compound or composition used to make Recycle PIA and the remainder is stored in inventory or is applied to future made Recycle PIA or is applied to existing Recycle PIA in inventory.

In one embodiment, the Recycle PIA, or articles made thereby, can be offered for sale or sold as Recycle PIA containing or obtained with recycle content. The sale or offer for sale can be accompanied with a certification or representation of the recycle content claim made in association with the Recycle PIA or article made with the Recycle PIA.

The obtaining of an allotment and designating (whether internally such as through a bookkeeping or an inventory tracking software program or externally by way of declaration, certification, advertising, representing, etc.) can be by the Recycle PIA manufacturer or within the Recycle PIA manufacturer Family of Entities. The designation of at least a portion of the Recycle PIA as corresponding to at least a portion of the allotment (e.g. allocation or credit) can occur through a variety of means and according to the system employed by the Recycle PIA manufacturer, which can vary from manufacturer to manufacturer. For example, the designation can occur internally merely through a log entry in the books or files of the Recycle PIA manufacturer or other inventory software program, or through an advertisement or statement on a specification, on a package, on the product, by way of a logo associated with the product, by way of a certification declaration sheet associated with a product sold, or through formulas that compute the amount deducted from inventory relative to the amount of recycle content applied to a product.

Optionally, the Recycle PIA can be sold. In one embodiment, there is provided a method of offering to sell or selling polymer and/or articles by:

a. A Recycle PIA manufacturer or its Family of Entities obtaining or generating a recycle content allotment, and the allotment can be obtained by any of the means described herein and can be deposited into inventory, the recycle content allotment having its origin in recycle textiles made into densified textile aggregates or in the densified textile aggregates, b. converting a reactant compound or composition in a synthetic process to make a compound, composition, polymer and/or article composition, c. designating (e.g. assigning or associating) a recycle content to at least a portion of the compound, composition, polymer and/or article composition from an inventory of allotments, where the inventory contains at least one entry that is an allotment associated with gasification of a feedstock containing densified textile aggregates. The designation can be the amount of allotment deducted from inventory, or the amount of recycle content declared or determined by the Recycle PIA manufacturer in its accounts. Thus, the amount of recycle content does not necessarily have to be applied to the Recycle PIA product in a physical fashion. The designation can be an internal designation to or by the Recycle PIA manufacturer or its Family of Entities or a service provider in contractual relationship to the Recycle PIA manufacturer or its Family of Entities, and d. offering to sell or selling the compound, composition, polymer and/or article composition as containing or obtained with recycle content corresponding at least in part with such designation. The amount of recycle content represented as contained in the Recycle PIA sold or offered for sale has a relationship or linkage to the designation. The amount of recycle content can be a 1:1 relationship in the amount of recycle content declared on a Recycle PIA offered for sale or sold and the amount of recycle content assigned or designated to the Recycle PIA by the Recycle PIA manufacturer.

The steps described need not be sequential, and can be independent from each other. For example, the step a) of obtaining an allotment and the step of making Recycle PIA from a reactant compound or composition can be simultaneous.

As used throughout, the step of deducting an allotment from an inventory of allotments does not require its application to a Recycle PIA product. The deduction also does not mean that the quantity disappears or is removed from the inventory logs. A deduction can be an adjustment of an entry, a withdrawal, an addition of an entry as a debit, or any other algorithm that adjusts inputs and outputs based on an amount recycle content associated with a product and one or a cumulative amount of allotments on deposit in the inventory. For example, a deduction can be a simple step of a reducing/debit entry from one column and an addition/credit to another column within the same program or books, or an algorithm that automates the deductions and entries/additions and/or applications or designations to a product slate. The step of applying an allotment to a Recycle PIA product where such allotment was deducted from inventory also does not require the allotment to be applied physically to a Recycle PIA product or to any document issued in association with the Recycle PIA product sold. For example, a Recycle PIA manufacturer may ship Recycle PIA product to a customer and satisfy the "application" of the allotment to the Recycle PIA product by electronically transferring a recycle content credit to the customer.

In one embodiment, the amount of recycle content in the recycle textile feedstock or in the Recycle PIA will be based on the allocation or credit obtained by the manufacturer of the Recycle PIA composition or the amount available in the Recycle PIA manufacturer's inventory of allotments. A portion or all of the allocation or credit obtained by or in the possession of a manufacturer of Recycle PIA can be designated and assigned to a recycle textile feedstock or Recycle PIA on a mass balance basis. The assigned value of the recycle content to the recycle textile feedstock or Recycle PIA should not exceed the total amount of all allocations and/or credits available to the manufacturer of the Recycle PIA or other entity authorized to assign a recycle content value to the Recycle PIA.

There is now also provided a method of introducing or establishing a recycle content in a compound, composition, polymer and/or article without necessarily using reactant compound or composition having recycle content. In this method, a. a syngas manufacturer makes a recycle textile derived syngas stream and b. a polymer and/or article manufacturer:

i. obtains an allotment associated with gasifying densified textile aggregates, ii. makes a polymer and/or article from any reactant compound or composition, and iii. associates at least a portion of the allotment with at least a portion of the polymer and/or article, whether or not the reactant compound or composition used to make the polymer and/or article contains a recycle content.

In this method, the polymer and/or article manufacturer need not purchase a recycle reactant compound or composition from a particular source or supplier, and does not require the polymer and/or article manufacturer to use or purchase a reactant compound or composition having recycle content in order to successfully establish a recycle content in the polymer and/or article composition. The polymer or article manufacturer may use any source of reactant compound or composition and apply at least a portion of the allocation or credit to at least a portion of the reactant compound or composition feedstock or to at least a portion of the polymer and/or article product. The association by the polymer and/or article manufacturer may come in any form, whether by on in its inventory, internal accounting methods, or declarations or claims made to a third party or the public.

There is also provided a use for a reactant compound or composition, the use including converting densified textile aggregates in any synthetic process, such as gasification, to make syngas and/or Recycle PIA.

There is also provided a use for a recycle densified textile aggregates that includes converting a reactant compound or composition in a synthetic process to make polymer and/or articles and applying at least a portion of an allotment to the polymer and/or article to the reactant compound or composition, where the allotment is associated with gasifying a feedstock containing a fossil fuel and densified textile aggregates or has its origin in an inventory of allotments where at least one deposit made into the inventory is associated with gasifying a feedstock containing a fossil fuel and recycle densified textile aggregates.

In one embodiment, there is provided a polymer and/or article composition that is obtained by any of the methods described above.

The reactant compound or composition, such a reactant compound or composition can be stored in a storage vessel and transferred to a Recycle PIA manufacturing facility by way of truck, pipe, or ship, or as further described below, the reactant compound or composition production facility can be integrated with the Recycle PIA facility. The reactant compound or composition may be shipped or transferred to the operator or facility that makes the polymer and/or article.

In an embodiment, the process for making Recycle PIA can be an integrated process. One such example is a process to make Recycle PIA by:

a. gasifying a feedstock containing a fossil fuel and recycle densified textile aggregates to make a densified textile derived syngas stream; and b. reacting said densified textile derived syngas or a non-densified textile derived syngas made in the gasifier in a reaction scheme to make a reactant compound or composition;

c. reacting any reactant compound or composition in a synthetic process to make a polymer and/or article;

d. depositing an allotment into an inventory of allotments, said allotment originating from gasifying a feedstock containing a fossil fuel and recycle densified textile aggregates; and e. applying any allotment from said inventory to the polymer and/or article to thereby obtain a recycle content polymer and/or article composition.

In one embodiment, one may integrate two or more facilities and make Recycle PIA. The facilities to make Recycle PIA, the reactant compound or composition, or the syngas can be stand-alone facilities or facilities integrated to each other. For example, one may establish a system of producing and consuming a reactant compound or composition, as follows:

a. provide a reactant compound or composition manufacturing facility configured to produce a reactant compound or composition;

b. provide a polymer and/or article manufacturing facility having a reactor configured to accept a reactant compound or composition from the reactant compound or composition manufacturing facility and making a polymer and/or article; and c. a supply system providing fluid communication between these two facilities and capable of supplying a reactant compound or composition from the reactant compound or composition manufacturing facility to the polymer and/or article manufacturing facility, wherein the reactant compound or composition manufacturing facility generates or participates in a process to generate allotments and gasifies a feedstock containing fossil fuel and recycle densified textile aggregates, and:

(i) said allotments are applied to the reactants compounds or compositions or to the polymer and/or article reactant, or (ii) are deposited into an inventory of allotments, and any allotment is withdrawn from the inventory an applied to the reactant compounds or compositions or to the polymer and/or article.

The reactant compound or composition manufacturing facility can make Recycle PIA by accepting any reactant compound or composition from the reactant compound or composition manufacturing facility and applying a recycle content to a polymer and/or article made with the reactant compound or composition by deducting allotments from its inventory and applying them to the Recycle PIA, optionally in amounts using the methods described above. The allotments withdrawn from inventory and applied can be allotments obtained by any source of recycle content, and need not necessarily be allotments associated with gasifying densified textile aggregates.

In one embodiment, there is also provided a system for producing Recycle PIA as follows:

a. provide a gasification manufacturing facility configured to produce an output composition comprising a densified textile derived syngas stream;

b. provide a reactant compound or composition manufacturing facility configured to accept a recycle textile derived syngas stream from the gasification manufacturing facility and making, through a reaction scheme one or more downstream products of said syngas to make an output composition comprising a reactant compound or composition;

c. provide a polymer and/or article manufacturing facility having a reactor configured to accept a reactant compound or composition and making an output composition comprising a recycle content Recycle PIA; and d. a supply system providing fluid communication between at least two of these facilities and capable of supplying the output composition of one manufacturing facility to another one or more of said manufacturing facilities.

The polymer and/or article manufacturing facility can make Recycle PIA. In this system, the gasification manufacturing facility can have its output in fluid communication with the reactant compound or composition manufacturing facility which in turn can have its output in fluid communication with the polymer and/or article manufacturing facility. Alternatively, the manufacturing facilities of a) and b) alone can be in fluid communication, or only b) and c). In the latter case, the polymer and/or article manufacturing facility can make Recycle PIA directly by having the recycle textile content syngas produced in the gasification manufacturing facility converted all the way to Recycle PIA, or indirectly by accepting any reactant compound or composition from the reactant compound or composition manufacturing facility and applying a recycle content to Recycle PIA by deducting allotments from its inventory and applying them to the Recycle PIA, optionally in amounts using the methods described above. The allotments obtained and stored in inventory can be obtained by any of the methods described above.

The fluid communication can be gaseous or liquid or both. The fluid communication need not be continuous and can be interrupted by storage tanks, valves, or other purification or treatment facilities, so long as the fluid can be transported from the manufacturing facility to the subsequent facility through an interconnecting pipe network and without the use of truck, train, ship, or airplane. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment, the integrated process includes at least two facilities co-located within 5, or within 3, or within 2, or within 1 mile of each other (measured as a straight line). In one embodiment, at least two facilities are owned by the same Family of Entities.

In an embodiment, there is also provided an integrated Recycle PIA generating and consumption system. This system includes:

a. Provide a gasification manufacturing facility configured to produce an output composition comprising a recycle textile derived syngas stream obtained by gasifying fossil fuel and recycle densified textile aggregates;

b. provide a reactant compound or composition manufacturing facility configured to accept a densified textile derived syngas stream from the gasification manufacturing facility and making, through a reaction scheme, one or more downstream products of said syngas to make an output composition comprising a reactant compound or composition;

c. provide a polymer and/or article manufacturing facility having a reactor configured to accept said reactant compound or composition and making an output composition comprising a polymer and/or article; and d. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. For example, the densified textile derived syngas can be delivered to the reactant compound or composition facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the reactant compound or composition reactor or the cracker, but rather to a delivery and receiving point at the respective facilities. The interconnecting pipework need not connect all three facilities to each other, but rather the interconnecting pipework can be between facilities a)-b), or b)-c), or between a)-b)-c).

In one embodiment or in combination with any of the mentioned embodiments, the total amount of carbon in the densified textile aggregate is at least 60 wt. %, or at least 65 wt. %, or at least 70 wt. %, or at least 75 wt. %, or at least 80 wt. %.

In one embodiment or in combination with any of the mentioned embodiments, the total amount of hydrogen in the densified textiles is desirably at least 5 wt. %, or at least 8 wt. %, or at least 10 wt. %.

In another embodiment, the ratio of total hydrogen to total carbon in the densified textile aggregates feed is higher than that of the other source of fuel. In one embodiment or in combination with any of the mentioned embodiments, the ratio of total hydrogen to total carbon in the densified textile aggregates used in the gasifier feedstock is at least 0.075, or at least 0.08, or at least 0.085, or at least 0.09, or at least 0.095, or at least 0.1, or at least 0.11, or at least 0.12, or at least 0.13 by weight.

In another embodiment, the densified textile aggregates used in the feedstock composition have an average fixed carbon content of less than 75 wt. %, or not more than 70 wt. %, or not more than 65 wt. %, or not more than 60 wt. %, or not more than 55 wt. %, or not more than 45 wt. %, or not more than 40 wt. %, or not more than 35 wt. %, or not more than 30 wt. %, or not more than 25 wt. %, or not more than 20 wt. %, or not more than 15 wt. %, or not more than 10 wt. %, or not more than 8 wt. %, or not more than 6 wt. %, or not more than 5 wt. %, or not more than 4 wt. %, or not more than 3 wt. %, or not more than 2 wt. %, or not more than 1 wt. %, based on the weight of the densified textile aggregates. The fixed carbon content is the combustible solids remaining (other than ash) after the material is heated and volatiles removed. It can be determined by subtracting the percentages of moisture, volatile matter, and ash from a sample.

If a large amount of densified textile aggregates is employed, which have a large mismatch in fixed carbon content compared to the fossil fuel used, variations in the syngas composition can be experienced outside of desirable limits. For example, a densified textile aggregate solid that has a very low fixed carbon content could, in an entrainment flow high temperature gasifier, gasify more readily than coal and proceed to generate more carbon dioxide within the residence time experienced by coal, while a co-feed of solids having a much higher fixed carbon content that coal would take longer to gasify and generate more unconverted solids. The degree of syngas compositional variations that can be tolerated will depend on the use of the syngas, and in the case of making chemicals, it is desirably to minimize the factors that could cause wider syngas compositional variations. In the process, syngas compositional variations attributable to the use of densified textile aggregates can be negligible by keeping the size reduced textiles concentration in the solids low.

The amount of densified textile aggregates present in the feedstock stream are up to 25 wt. %, or up to 20 wt. %, or up 15 wt. %, or up to 12 wt. %, or up to 10 wt. %, or up to 7 wt. %, or up to 5 wt. %, or less than 5 wt. % based on the weight of the solids in the fuel feedstock stream or composition, or can range from 0.1 wt. % to 25 wt. %, or from 0.1 wt. % to 20 wt. %, or from 0.1 wt. % to 15 wt. %, or from 0.1 wt. % to 12 wt. %, or from 0.1 wt. % to 7 wt. %, or from 0.1 wt. % to 5 wt. %, or from 0.1 wt. % to less than 5 wt. %, or from 0.1 wt. % to 4 wt. %, or from 0.1 wt. % to 3 wt. %, or from 0.1 wt. % to 2.5 wt. %, or from 0.1 wt. % to 2 wt. %, or from 0.1 wt. % to less than 2 wt. %, or from 0.1 wt. % to 1.5 wt. %, 0.5 wt. % to 25 wt. %, or from 0.5 wt. % to 20 wt. %, or from 0.5 wt. % to 15 wt. %, or from 0.5 wt. % to 12 wt. %, or from 0.5 wt. % to 7 wt. %, or from 0.5 wt. % to 5 wt. %, or from 0.5 wt. % to less than 5 wt. %, or from 0.5 wt. % to 4 wt. %, or from 0.5 wt. % to 3 wt. %, or from 0.5 wt. % to 2.5 wt. %, or from 0.5 wt. % to 2 wt. %, or from 0.5 wt. % to less than 2 wt. %, or from 0.5 wt. % to 1.5 wt. %, 1 wt. % to 25 wt. %, or from 1 wt. % to 20 wt. %, or from 1 wt. % to 15 wt. %, or from 1 wt. % to 12 wt. %, or from 1 wt. % to 7 wt. %, or from 1 wt. % to 5 wt. %, or from 1 wt. % to less than 5 wt. %, or from 1 wt. % to 4 wt. %, or from 1 wt. % to 3 wt. %, or from 1 wt. % to 2.5 wt. %, or from 1 wt. % to 2 wt. %, or from 1 wt. % to less than 2 wt. %, or from 1 wt. % to 1.5 wt. %, in each case based on the weight of all fuel feedstock fed to the gasifier, whether solid or liquid, or alternatively based on the weight of all solids in the feedstock stream or composition fed to the gasifier or in the gasification zone. Since densified textile aggregates have, on average, a much lower fixed carbon content than solid fossil fuels, the amount of carbon dioxide they generate will be more than that of the solid fossil fuels at the same residence time as the solid fossil fuels in the gasification zone and on the same weight basis. Desirably, the amount of the densified textile aggregates is low to obtain the advantage of minimizing an increase of carbon dioxide content over that generated by the solid fossil fuels alone. For example, the amount of densified textile aggregate relative to all sources of fuel (solid, liquid, or gas), or relative to solids, fed to the gasifier is not more than 10 wt. %, or not more than 9 wt. %, or not more than 8 wt. %, or not more than 7 wt. %, or not more than 6 wt. %, or not more than 5 wt. %, or not more than 4 wt. %, or not more than 3.5 wt. %, or not more than 3 wt. %, or not more than 2.75 wt. %, or not more than 2.5 wt. %, or not more than 2.25 wt. %, or not more than 2 wt. %, or not more than 1.75 wt. %, or not more than 1.5 wt. %, or not more than 1.25 wt. %, or not more than 1 wt. %, based on the weight of all gasifier fuel fed to the gasifier (and fuel does not include the oxidizer, steam, water, or carbon dioxide gas), or based on the weight of all solids fed. Examples of the content of densified textile aggregates present in the feedstock composition include 0.25 wt. % to less than 5 wt. %, or from 0.25 wt. % to 4 wt. %, or from 0.25 wt. % to 3 wt. %, or from 0.25 wt. % to 2.5 wt. %, or from 0.5 wt. % to 5 wt. %, or from 0.5 wt. % to 4 wt. %, or from 0.5 wt. % to 3 wt. %, or from 0.5 wt. % to 2.5 wt. %, or from 1 wt. % to 5 wt. %, or from 1 wt. % to 4 wt. %, or from 1 wt. % to 3 wt. %, or from 1 wt. % to 2.5 wt. % each based on the weight of the fuel or solids in the feedstock composition.

In another embodiment, the densified textile aggregates used in the gasifier feedstock composition have an average fixed carbon content that is at least 3% less, or at least 5% less, or at least 7% less, or at least 9% less, or at least 10% less, or at least 13% less, or at least 15% less, or at least 17% less, or at least 20% less, or at least 23% less, or at least 25% less, or at least 27% less, or at least 30% less, or at least 32% less, or at least 35% less, or at least 38% less, or at least 40% less, or at least 43% less, or at least 45% less, or at least 47% less, or at least 50% less, or at least 55% less, or at least 60% less, or at least 70% less, or at least 80% less, or at least 90% less, or at least 95% less, than the fixed carbon content of coal, or optionally all solid fossil fuel employed in the feedstock composition, or optionally any solids other that densified textile aggregates, or any other fuel fed to the gasifier.

The densified textile aggregates can have an average sulfur content that is fairly sizable since the high temperature or slagging gasifiers are well equipped to handle sulfur, although in practice textiles have a very low or only trace amounts of sulfur. The densified textile aggregates can have an average sulfur content of up to 1 wt. %, or up to 0.5 wt. %, or up to 0.25 wt. %, or up to 0.1 wt. %, or up to 0.05 wt.

%, or up to 0.01 wt. %, or up to 0.005 wt. %, or up to 0.0001 wt. %, based on the weight of the densified textile aggregates.

The densified textile aggregates may have a widely varying ash content depending on the type of textile they are made from and the purity the densified textile aggregates stream to the select densified textile aggregates. The densified textile aggregates may have an average ash content of at least 1 wt. %, or at least 2 wt. %, or at least 3 wt. %, or at least 4 wt. %, or at least 5 wt. %, or at least 5.5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. % based on the weight of the densified textile aggregates. The densified textile aggregates may have an average ash content of not more than 60 wt. %, or not more than 55 wt. %, or not more than 55 wt. %, or not more than 55 wt. %, or not more than 55 wt. %, or not more than 40 wt. %, or not more than 30 wt. %, or not more than 20 wt. %, or not more than 15 wt. %, or not more than 10 wt. %, desirably not more than 8 wt. %, or not more than 7 wt. %, or not more than 6 wt. %, or not more than 5.5 wt. %, or not more than 5 wt. %, or not more than 4.5 wt. %, or not more than 4 wt. %, or not more than 3 wt. %, or not more than 2.5 wt. %, based on the weight of the densified textile aggregates.

In another embodiment, the average oxygen content in the densified textile aggregates can be at zero or at least 0.1 wt. %, or at least 0.5 wt. %, or at least 1 wt. %, or at least 2 wt. %, or at least 4 wt. %, or at least 6 wt. %, or at least 8 wt. %, or at least 10 wt. %, or at least 13 wt. %, or at least 15 wt. %, or at least 18 wt. %, or at least 20 wt. %, based on the weight of the densified textile aggregates. Desirably, to improve the HHV, the amount of oxygen is kept low, such as not more than 20 wt. %, or not more than 15 wt. %, or not more than 10 wt. %, or not more than 8 wt. %, or not more than 5 wt. %, or not more than 4 wt. %, or not more than 2 wt. %, or not more than 1 wt. %, based on the weight of the densified textile aggregates.

The content of minerals, metals and elements other than carbon, hydrogen, oxygen, nitrogen, and sulfur, in the densified textile aggregates can be at least 0.01 wt. %, or at least 0.1 wt. %, or at least 0.5 wt. %, or at least 1 wt. %, or at least 1.5 wt. %, or at least 1.8 wt. %, or at least 2 wt. %, or at least 2.3 wt. %, or at least 2.5 wt. %, or at least 2.8 wt. %, or at least 3 wt. %, based on the weight of the densified textile aggregates. The upper amount is not particularly limited, and generally would not exceed 8 wt. %, or not exceed 7 wt. %, or not exceed 6 wt. %, or not exceed 5 wt. %, or not exceed 4.5 wt. %, or not exceed 4 wt. %, or not exceed 3.8 wt. %.

The particle size of the densified textile aggregates is desirably not larger than the maximum size the gasifier in use can accept. Many coal fed gasifiers can grind or mill the coal to a desired size before feeding them to the gasification zone. Relying upon such grinding or milling operations to achieve the desired densified textile aggregate particle size that are densified by a heat treatment process is not advisable since the elasticity or variability of elasticity of the densified textile aggregates can lead them to pancake, form platelets, or otherwise smear when co-granulating or co-grinding with the more hard and brittle carbonaceous fuel sources like coal or pet coke. However, In one embodiment or in combination with any of the mentioned embodiments, densified textile agglomerates can be fed to a solid fossil fuel milling or grinding operation along with a solid fossil fuel to reduce the size of the agglomerates since agglomerates are more friable and break apart easier than do particles made through a heat treatment process. In this embodiment, the size of the agglomerates fed to the mill or grinder are larger than the maximum size the gasifier in use can accept, or are larger than the average particle size of the solid fossil fuel after milling or grinding or as fed to the gasifier, in each case as measured in the largest dimensions and as an average median particle size. If desired, however, due to the variability in thermoplastic content and types of polymers in the densified textile aggregates, the densified textile aggregate, whether in the form of an agglomerate or heat treated particles, can be of a size not to exceed the maximum size the gasifier in use can accept, or not to exceed or be smaller than the average target particle size of the solid fossil fuel after milling or grinding or as fed to the gasifier, in each case as measured in the largest dimensions and as an average median particle size.

The actual particle size of the densified textile aggregates can vary with the type of gasifier used. For example, particles having an average particle size of ¼ inch or less in their largest dimension cannot be processed through an entrained flow coal gasifier. However, fixed bed or moving bed gasifiers can accept larger particle sizes. Examples of suitable sizes of densified textile aggregates fed to a fixed bed or moving bed gasifier are not more than 12 inches, or not more than 8 inches, or not more than 6 inches, or not more than 5 inches, or not more than 4 inches, or not more than 3.75 inches, or not more than 3.5 inches, or not more than 3.25 inches, or not more than 3 inches, or not more than 2.75 inches, or not more than 2.5 inches, or not more than 2.25 inches, or not more than 2 inches, or not more than 1.75 inches, or not more than 1.5 inches, or not more than 1.25 inches. The size can be at least 2 mm, or at least ⅛ inches, or at least ¼ inches, or at least ½ inches, or at least 1 inch, or at least 1.5 inches, or at least 1.75 inches, or at least 2 inches, or at least 2.5 inches, or at least 3 inches, or at least 3.5 inches, or at least 4 inches, or at least 4.5 inches, or at least 5 inches, or at least 5.5 inches. Such relatively large densified textile aggregates are better suited for use in fixed or moving bed gasifiers, especially those that are updraft fixed or moving bed gasifiers.

With many gasifier designs, the fossil fuel (coal or pet-coke) and the densified textile aggregates are size reduced for multiple purposes. The densified textile aggregates are of a small size as is the fossil fuel source to (i) allow for faster reaction once inside the gasifier due to mass transfer limitations, (ii) to create a slurry that is stable, fluid and flowable at high concentrations of solids to water in slurry fed gasifiers, (iii) to pass through processing equipment such as high-pressure pumps, valves, and feed injectors that have tight clearances, (iv) to flow through screens between the mills or grinders and the gasifier, or (v) to be conveyed with gases used for conveying solid fossil fuels to dry fed gasifiers.

In one embodiment or in combination with any of the mentioned embodiments, the densified textile aggregate particle sizes are desirably not more than 5 inches, or not more than 4 inches, or not more than 1 inch, or not more than ¼ inch, or not more than 2 mm. The larger sizes are useful for addition to a fixed bed or moving bed gasifier, particularly in updraft gasifiers to provide sufficient density to allow them to contact the bed as a solid that has not fully charred or be converted to ash.

In one embodiment or in combination with any of the mentioned embodiments, the solids in the gasifier feedstock, including the densified textile aggregates, have a particle size of 2 mm or smaller. This embodiment is particularly attractive to entrained flow gasifiers, including dry feed and slurry fed gasifiers, and to fluidized bed gasifiers. As used throughout, unless a different basis is expressed (e.g. a mean), a stated size means that at least 90 wt. % of the particles have a largest dimension in the stated size, or alternatively that 90 wt. % pass through sieve designated for that particle size. Either conditions satisfy the particle size designation. Densified textile aggregates sized larger than 2 mm for an entrained flow gasifier have the potential for being blown through the gasification zone of entrained flow gasifiers without completely gasifying, particularly when the gasification conditions are established to gasify solid fossil fuel having a particle dimension of 2 mm or smaller.

In one embodiment or in combination with any of the mentioned embodiments, the size of the densified textile aggregates as such or as combined with a fossil fuel, or in the gasifier feed, or injected into the gasification zone, is 2 mm or smaller or constitute those particles passing through a 10 mesh, or 1.7 mm or smaller (those particles passing through a 12 mesh), or 1.4 mm or smaller (those particles passing through a 14 mesh), or 1.2 mm or smaller (those particles passing through a 16 mesh), or 1 mm or smaller (those particles passing through a 18 mesh), or 0.85 mm or smaller (those particles passing through a 20 mesh), or 0.7 mm or smaller (those particles passing through a 25 mesh) or 0.6 mm or smaller (those particles passing through a 30 mesh), or 0.5 mm or smaller (those particles passing through a 35 mesh), or 0.4 mm or smaller (those particles passing through a 40 mesh), or 0.35 mm or smaller (those particles passing through a 45 mesh), or 0.3 mm or smaller (those particles passing through a 50 mesh), or 0.25 mm or smaller (those particles passing through a 60 mesh), or 0.15 mm or smaller (those particles passing through a 100 mesh), or 0.1 mm or smaller (those particles passing through a 140 mesh), or 0.07 mm or smaller (those particles passing through a 200 mesh), or 0.044 mm or smaller (those particles passing through a 325 mesh), or 0.037 mm or smaller (those particles passing through a 400 mesh). In another embodiment, the size of the densified textile aggregates particles is at least 0.037 mm (or 90% retained on a 400 mesh).

In one embodiment or in combination with any of the mentioned embodiments, the densified textile aggregates have a particle size that, after optional sieving, is acceptable for gasifying within the design parameters of the type of gasifier used. The particle sizes of densified textile aggregates and the solid fossil fuels can be sufficiently matched to retain the stability of the slurry and avoid a coal/densified textile aggregates separation at high solids concentrations prior to entering the gasification zone in the gasifier. A feedstock composition that phase separates, whether between solids/liquid or solid/solids in a slurry, or solids/ solids in a dry feed, or solid/liquid in a liquid feedstock, can plug lines, created localized zones of gasified densified textile aggregates, create inconsistent ratios of fossil fuel/ densified textile aggregates, and can impact the consistency of the syngas composition. Variables to consider for determining the stability of the feedstock composition include setting an optimal particle size of the densified textile aggregates, and variables for determining the optimal particle sizes include the bulk density of the ground coal, the concentration of all solids in the slurry if a slurry is used or the solid/solid concentration in a dry feed, the effectiveness of any additives employed such as surfactants/stabilizers/ viscosity modifiers, and the velocity and turbulence of the feedstock composition to the gasifier and through the injector nozzles.

In one embodiment or in combination with any of the mentioned embodiments, the bulk density of the densified textile aggregates after final grinding is within 150%, or within 110%, or within 100%, or within 75%, or within 60%, or within 55%, or within 50%, or within 45%, or within 40%, or within 35% of the bulk density of the ground fossil fuel that is used as a feed introduced to the gasification zone. For example, if the granulated coal has a bulk density of 40 lbs./ft³ and the densified textile aggregates have a bulk density of 33 lbs./ft³, the bulk density of the densified textile aggregates would be within 21% of the ground coal. For measurement purposes, the bulk density of the densified textile aggregates and the fossil fuel after final grinding is determined on a dry basis (without addition of water) even if they are ultimately used as a slurry.

In one embodiment or in combination with any of the mentioned embodiments, the maximum particle size of the densified textile aggregates is selected to be similar (below or above) to the maximum particle size of the ground solid fossil fuel. The maximum particle size of the densified textile aggregates used in the gasifier feedstock can be not more than 50% larger than the maximum solid fossil fuel size in the gasifier feedstock, or not more than 45%, or not more than 40%, or not more than 35%, or not more than 30%, or not more than 25%, or not more than 20%, or not more than 15%, or not more than 10%, or not more than 5%, or not more than 3%, or not more than 2%, or not more than 1% larger than the maximum solid fossil fuel size in the gasifier feedstock, or not larger than, or smaller than the maximum solid fossil fuel size in the gasifier feedstock. Optionally, the maximum particle size of the densified textile aggregates used in the gasifier feedstock as stated above can be within (meaning not larger than and not smaller than) the stated values. The maximum particle size is not determined as the maximum size of the particle distribution but rather by sieving through meshes. The maximum particle size is determined as the first mesh which allows at least 90 volume % of a sample of the particles to pass. For example, if less than 90 volume % of a sample passes through a 300 mesh, then a 100 mesh, a 50 mesh, a 30 mesh, a 16 mesh, but succeeds at a 14 mesh, then the maximum particle size of that sample is deemed to correspond to the first mesh size that allowed at least 90 volume % to pass through, and in this case, a 14 mesh corresponding to a maximum particle size of 1.4 mm.

The densified textile aggregates are desirably isolated as a densified textile aggregates feed for ultimate destination to be fed to a gasifier. In one embodiment or in combination with any of the mentioned embodiments, at least 80 wt. %, or at least 85 wt. %, or at least 90 wt. %, or at least 95 wt. %, or at least 96 wt. %, or at least 97 wt. %, or at least 98 wt. %, or at least 99 wt. %, or at least 99.5 wt. %, or 100 wt. % of all solid feedstock other than solid fossil fuels and sand fed to the gasifier is densified textile aggregate, based on the cumulative weight of all streams containing solids fed to the gasifier.

The densified textile aggregates are combined with one or more fossil fuel components of the feedstock stream at any location prior to introducing the feedstock stream into gasification zone within the gasifier. Solid fossil fuel grinding equipment will provide an excellent source of energy for mixing densified textile aggregates with the solid fossil fuel while reducing the size of the solid fossil fuel particles. Therefore, one of the desirable locations for combining densified textile aggregates having a target size for feeding into the gasifier is into the equipment used for grinding the other solid fossil fuel sources (e.g. coal, pet-coke). This location is particularly attractive in a slurry fed gasifier because it is desirable to use a feed having the highest stable solids concentration possible, and at higher solids concentration, the viscosity of the slurry is also high. The torque and shear forces employed in fossil fuel grinding equipment is high, and coupled with the shear thinning behavior of a solid fossil fuel (e.g. coal) slurry, good mixing of the densified textile aggregates with the ground fossil fuel can be obtained in the fossil fuel grinding equipment.

Other locations for combining densified textile aggregates with fossil fuel sources can be onto the fossil fuel loaded on the main fossil fuel belt feeding a mill or grinder, or onto the main fossil fuel before the fossil fuel is loaded onto the belt to the mill or grinder, or into a fossil fuel slurry storage tank containing a slurry of fossil fuel ground to the final size, particularly if the storage tank is agitated.

Figure 5:
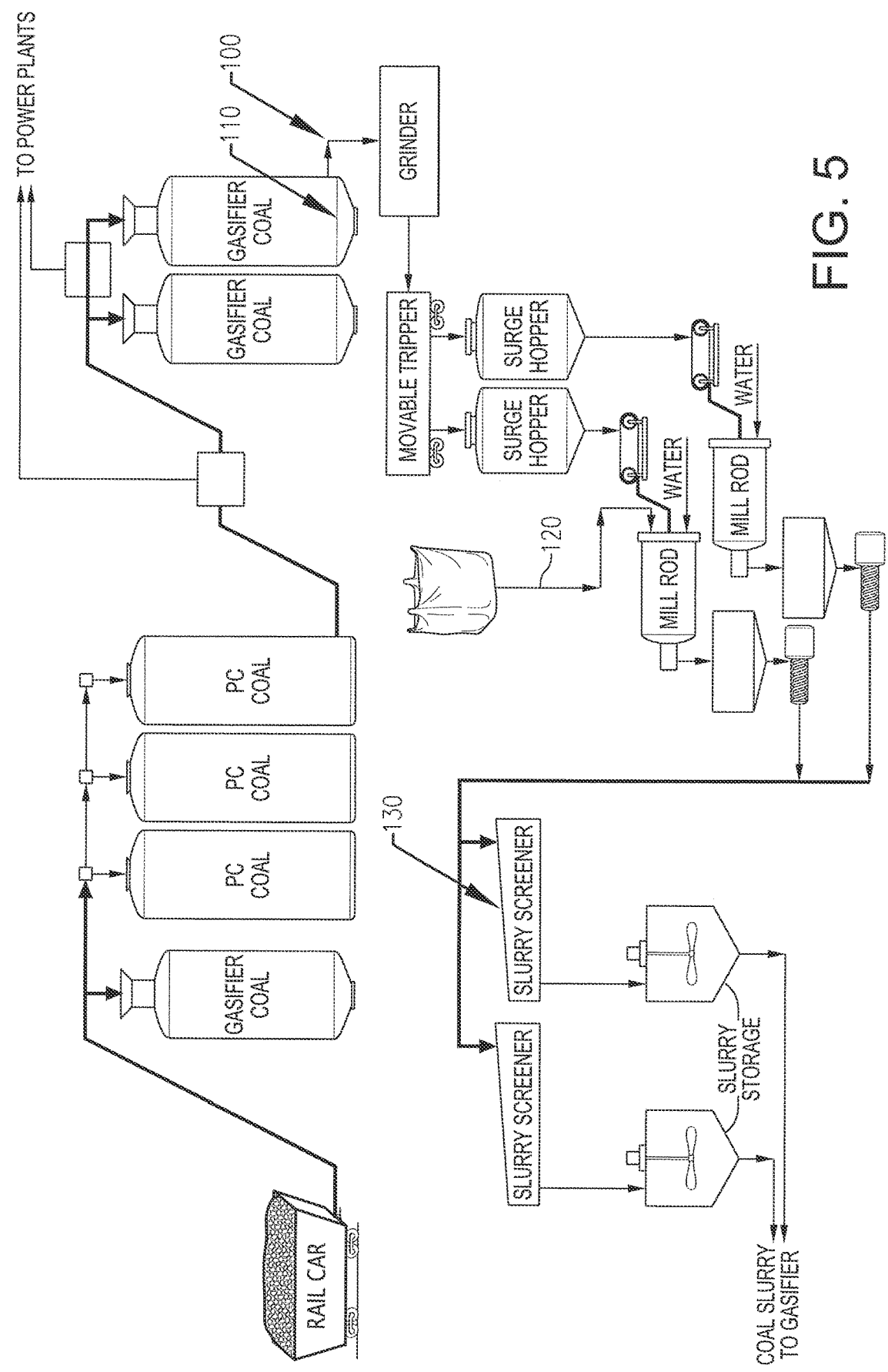
FIG. 5 is a detailed view of the locations for adding size reduced textiles to a solid fossil fuel.

More particularly, there are several locations that provide a safe, economic and effective way to introduce densified textile aggregates to a slurry fed coal gasifier. In additional embodiments of the invention, FIG. 5 shows four locations where post-consumer densified textile aggregates can be introduced. All of these points are in the low-pressure section (lower than the pressure within the gasifier or gasification zone) of the process thus reducing the cost of modifications.

In an embodiment of the invention shown in FIG. 5, the densified textile aggregates can be introduced at location 100, the main fossil fuel belt (e.g. coal feed belt). For purposes of convenience, reference is made to coal in FIG. 5 although it is to be understood that any solid fossil fuel can be employed. The densified textile aggregates are metered onto the main coal feed belt as it moves past with the coal already loaded onto the belt. The densified textile aggregates are added to the belt using a weigh belt feeder, or other similar device, to measure the mass of the material, and the speed of the belt to determine addition rate. The coal is similarly added to the same belt and would be underneath the densified textile aggregates. The combined solid mixture of the coal and densified textile aggregates in the proper ratio are then conveyed to surge hoppers and other storage and conveying equipment until it is ultimately fed to the coal grinding mill. In the coal grinding mill, the coal, densified textile aggregates, water and viscosity modifiers are mixed thoroughly, and the coal is reduced in size to the target grind size distribution and the mixture becomes a viscous slurry. The densified textile aggregates undergo very little or no size reduction since it is a softer material, but benefits from the extreme mixing in the mill due to its inclusion into the slurry production process. The densified textile aggregates have been size reduced the same average size as introduced into the gasification zone and do not need any further size reduction after addition to the solid fossil fuel or water used to make the slurry.

In another embodiment of the invention, densified textile aggregates can be introduced as shown in FIG. 5 location number 110. This is the same process as described in location number 100 above, except that the densified textile aggregates are added to the main coal belt first, before the coal is added. In this manner, the coal is on top. Since the densified textile aggregates may have a lower bulk density than coal or other solid fossil fuel, it may be easier for the densified textile aggregates to be blown off of the belt in a strong wind upon deposition or as it moves down the belt, or otherwise when screened. With the more dense solid fossil fuel covering the densified textile aggregates, this dusting and loss of material can be greatly reduced.

In another embodiment the invention, the densified textile aggregates can be added at location number 120, the grinding mill. The existing equipment, coal, water and viscosity modifiers are already added to the grinding mill to reduce the particle size of the coal or petcoke and produce a viscous slurry high in solids. The densified textile aggregates can be independently conveyed to the entry point of the mill and added directly to the mill in the proper ratio. The mill will then grind the solid fossil fuel, produce the slurry and thoroughly mix in the densified textile aggregates in the process. This avoids wind and weather effects on the coal, recycled material mixture.

In yet another embodiment of the invention the densified textile aggregates can be introduced at location number 130, the slurry storage tank. Since the densified textile aggregates are pre-ground to the proper particle size for introduction into the gasifier, it can be added to the slurry storage tank directly after the grinding/slurry operation. Alternatively, densified textile aggregates can be added to the tank through a separate screen or the screen used by the slurry to ensure no excessively large densified textile aggregates are passed to the tank. This is the last low-pressure addition point before the slurry is pumped at pressure to the gasifier. This will minimize the amount of material in process that is mixed together. The agitation in the slurry tanks will mix in the densified textile aggregates densified textile aggregates to ensure they are evenly distributed.

Granulators can be used to obtain the desired size reduction. These can include systems for shredding the textiles using high capacity shredders, and if necessary, a fine/powder granulator can be used in a last step. For the last step, the fine/powder granulators can be in communication with a conveying system to transport the densified textile aggregates to a storage vessel from which the densified textile aggregates particles can be fed to any location for making the feedstock stream, or the particles can be fed continuously from the fine granulator to the desired location for making the feedstock stream. The feed of granulated densified textile aggregates particles from a storage vessel can be in a batch mode or in a continuous mode.

In one embodiment or in combination with any mentioned embodiments, the feedstock materials, e.g. fossil fuel and densified textile aggregates are advantageously loose and not densified by mechanical or chemical means after the densified textile aggregates are combined with the solid fossil fuel such as coal (other than natural compaction that may result from storage under its own weight). For example, once densified textile aggregates are contacted with coal, the combination is not densified.

The solid fossil fuel is typically ground to a size of 2 mm or less, and can be ground to any of the sizes noted above with respect to the densified textile aggregates of less than 2 mm. The small size of the coal and densified textile aggregates particles is advantageous to enhance a uniform suspension in the liquid vehicle which will not settle out, to allow sufficient motion relative to the gaseous reactants, to assure substantially complete gasification, and to provide pumpable slurries of high solids content with a minimum of grinding.

In one embodiment or in combination with any of the mentioned embodiments, both densified textile aggregates and recycle plastic particles are fed to the gasifier. For example, a single feedstock composition can contain the densified textile aggregate and recycle plastic particles, or they may be contained in separate streams fed to the gasifier. In one embodiment or in combination with any of the mentioned embodiments, at least 80 wt. %, or at least 85 wt.

%, or at least 90 wt. %, or at least 95 wt. %, or at least 96 wt. %, or at least 97 wt. %, or at least 98 wt. %, or at least 99 wt. %, or at least 99.5 wt. %, or 100 wt. % of all solid feedstock, other than solid fossil fuels, fed to the gasifier is densified textile aggregate and recycle plastic particles, based on the cumulative weight of all streams containing solids fed to the gasifier.

In one embodiment or in combination with any of the mentioned embodiments, the solids fed to the gasifier include a combination of densified textiles aggregate particles and recycle plastic particles as a solid/solid combination, and desirably also solid fossil fuel particles. The weight ratio of densified textile aggregate to recycle plastic particles can be from 1:99 to 99:1, or 10:90 to 90:10, or 20:80 to 80:20, or from 30:70 to 70:30.

If recycle plastic particles are used in combination with the densified textile aggregate, the recycle plastic particles are desirably not more than any of the sizes mentioned above applicable to the densified textile aggregate.

The solids in the feedstock composition desirably do not contain sewage sludge, wastepaper not already embedded in a thermoplastic matrix, or biomass. In one embodiment or in combination with any of the mentioned embodiments, the feedstock composition contains not more than 10 wt. %, or not more than 6 wt. %, or not more than 5 wt. %, or not more than 4 wt. %, or not more than 3 wt. %, or not more than 2 wt. %, or not more than 1 wt. %, or not more than 0.5 wt. %, or not more than 0.25 wt. %, or not more than 0.1 wt. % of any one of sewage sludge, waste paper not embedded in a thermoplastic matrix, biomass, or a combination of two or more, each based on the weight of the solids in the feedstock composition.

The densified textile aggregates may contain some level of inorganic materials other than polymer, such as metals, glass (whether in the form of fibers or particles), mineral fillers, and other inorganic materials. The quantity of such materials in the densified textile aggregates that feed into the feedstock composition, is desirably less than 8 wt. %, or not more than 6 wt. %, or not more than 5 wt. %, or not more than 4 wt. %, or not more than 3.5 wt. %, or not more than 2 wt. %, or not more than 1.5 wt. %, or not more than 1 wt. %, or not more than 0.75 wt. %, or not more than 0.5 wt. %, based on the weight of the densified textile aggregate.

The amount of solid fossil fuel, such as coal, in the feedstock or fed to the gasifier can be at least 10 wt. %, or at least 80 wt. %, or at least 85 wt. %, or at least 90 wt. %, or at least 93 wt. %, or at least 95 wt. %, or at least 97 wt. %, or at least 98 wt. %, or at least 98.5 wt. %, or at least 99 wt. %, and less than 100 wt. %, or less than 99.5 wt. %, based on the weight of solids in the feedstock.

Coal contains a quantity of ash that also contains elements other than carbon, oxygen, and hydrogen. The quantity of elements other than carbon, hydrogen, oxygen, and sulfur in the fossil fuel, or in the feedstock composition, is desirably not more than 15 wt. %, or not more than 13 wt. %, or not more than 10 wt. %, or not more than 9 wt. %, or not more than 8.5 wt. %, or not more than 8 wt. %, or not more than 7.5 wt. %, or not more than 7 wt. %, or not more than 7.5 wt. %, or not more than 7 wt. %, or not more than 6.5 wt. %, or not more than 6 wt. %, or not more than 5.5 wt. %, or not more than 5 wt. %, or not more than 4.5 wt. %, based on the dry weight of the fossil fuel or alternatively based on the weight of all dry solids in the feedstock composition, or based on the weight of the feedstock composition, respectively.

The caloric heat value of densified textile aggregates is desirably similar to or better than that of coal. For example, the densified textile aggregates can have a heat value of at least 13,000, or at least 13,500, or at least 14,000 BTU/lb., or in the range of 13,000 to 15,000 BTU/lb. (30 MJ/Kg-35 MJ/Kg), while bituminous coal can have a heat value in a range of 12,500 to 13,300 BTU/lb. (29-31 MJ/Kg). Further, any ash or non-organic material can be melted and vitrified into the ash or slag matrix that is produced from the inorganics in the coal.

The concentration of solids (e.g. fossil fuel and densified textile aggregates) in the feedstock composition should not exceed the stability limits of a slurry or solids/solids mix, or the ability to pump or feed the feedstock at the target solids concentration to the gasifier. Desirably, the solids content of a slurry should be at least 50 wt. %, or at least 55 wt. %, or at least 60 wt. %, or at least 62 wt. %, or at least 65 wt. %, or at least 68 wt. %, or at least 69 wt. %, or at least 70 wt. %, or at least 75 wt. %, the remainder being a liquid phase that can include water and liquid additives. The upper limit is not particularly limited because it is dependent upon the gasifier design. However, given the practical pumpability limits of a solid fossil fuels feed and maintaining a homogeneous distribution of solids in the slurry, the solids content for a solid fossil slurry fed slagging gasifier desirably should not exceed 75 wt. %, or 73 wt. %, the remainder being a liquid phase that can include water and liquid additives (as noted above, gases are not included in the calculation of weight percentages). The solids concentration of a dry fed gasifier is desirably 95 wt. % or more, or 97 wt. % or more, or 98 wt. % or more, or 99 wt. % or more, or 100 wt. %, based on the weight of the gasifier feedstock composition (excluding the weight of the gas and moisture contained in the solids).

A slurry feedstock composition is desirably stable at 5 minutes, or even 10 minutes, or even 15 minutes, or even 20 minutes, or even ½ hour, or even 1 hour, or even two hours. A slurry feedstock is deemed stable if its initial viscosity is 100,000 cP or less. The initial viscosity can be obtained by the following method. A 500-600 g of a well-mixed sample is allowed to stand still in a 600 mL liter glass beaker at ambient conditions (e.g. 25° C. and about 1 atm). A Brookfield R/S Rheometer equipped with V80-40 vane operating at a shear rate of 1.83/ s is submerged into the slurry to the bottom of the beaker after the slurry is well mixed (e.g. a homogeneous distribution of solids was formed). After a designated period of time, a viscosity reading is obtained at the start of rotation, which is the initial viscosity reading. The slurry is considered to be stable if the initial reading on starting a viscosity measurement is not more than 100,000 cP at the designated period of time. Alternatively, the same procedure can be used with a Brookfield viscometer with an LV-2 spindle rotating at a rate of 0.5 rpm. Since different viscosity value will be obtained using the different equipment, the type of equipment used should be reported. However, regardless of the differences, the slurry is considered stable under either method only if its viscosity is not more than 100,000 cP at the reported time.

The quantity of solids in the feedstock composition and their particle size are adjusted to maximize the solids content while maintaining a stable and pumpable slurry. A pumpable slurry is one which has a viscosity under 30,000 cP, or not more than 25,000 cP, or not more than 23,000 cP, and desirably not more than 20,000 cP, or not more than 18,000 cP, or not more than 15,000 cP, or not more than 13,000 cP, in each case at ambient conditions (e.g. 25° C. and 1 atm). At higher viscosities, the slurry becomes too thick to practically pump. The viscosity measurement to determine the pumpability of the slurry is taken by mixing a sample of the slurry until a homogeneous distribution of particles is obtained, thereafter immediately submerging a Brookfield viscometer with an LV-2 spindle rotating at a rate of 0.5 rpm into the well mixed slurry and taking a reading without delay. Alternatively, a Brookfield R/S rheometer with V80-40 vane spindle operating at a shear rate of 1.83/ s can be used. The method of measurement is reported since the measured values between the two rheometers at their difference shear rates will generate different values. However, the cP values stated above apply to either of the rheometer devices and procedures.

In one embodiment or in combination with any of the mentioned embodiments, the slurry feedstock composition has a viscosity of 80,000 cP or less, or 70,000 cP or less, or 60,000 cP or less, 50,000 cP or less, or 40,000 cP or less, or 35,000 cP or less, or 25,000 cP or less, or 20,000 cP or less, or 15,000 cP or less, or 10,000 cP or less, in each case, at 5 minutes, or even 10 minutes, or even 15 minutes, or even 20 minutes, desirably at 5 minutes or at 20 minutes, or at 20 minutes and desirably at 60,000 cP or less or 40,000 cP or less.

In one embodiment or in combination with any of the mentioned embodiments, the fossil fuel is at least coal. The quality of the coal employed is not limited. Anthracite, bituminous, sub-bituminous, brown coal, and lignite coal can be sources of coal feedstock. To increase the thermal efficiency of the gasifier, the coal employed desirably has a carbon content that exceeds 35 wt. %, or at least 42 wt. %, based on the weight of the coal. Accordingly, bituminous or anthracite coal is desirable due to their higher energy content.

Sulfur is also typically present in solid fossil fuels. Desirably, the content of sulfur is less than 5 wt. %, not more than 4 wt. %, or not more than 3 wt. %, or not more than 2.5 wt. %, and also can contain a measure of sulfur, such as at least 0.25 wt. %, or at least 0.5 wt. %, or at least 0.75 wt. %, based on the weight of the solid fossil fuel.

It is also desirable to employ a solid fossil fuel with a low inherent moisture content to improve the thermal efficiency of the gasifier. Using coal having moisture contents less than 25 wt. % or less than 20 wt. % or less than 15 wt. % or not more than 10 wt. % or not more than 8 wt. % is desirable to improve the energy efficiency of the gasifier.

Desirably, the coal feedstock has a heat value of at least 11,000 BTU/lb., or at least 11,500 BTU/lb., or at least 12,500 BTU/lb., or at least 13,000 BTU/lb., or at least 13,500 BTU/lb., or at least 14,000 BTU/lb., or at least 14,250 BTU/lb., or at least 14,500 BTU/lb.

In a slurry fed gasifier, while it is possible that the feedstock composition may contain minor amounts of liquid hydrocarbon oils leached from densified textile aggregates or coal, the feedstock composition desirably contains less than 5 wt. %, or not more than 3 wt. %, or not more than 1 wt. %, or not more than 0.1 wt. % liquid (at ambient conditions) non-oxygenated hydrocarbon petroleum oils introduced as such into the feedstock composition. Desirably, the feedstock composition contains less than 2 wt. %, or not more than 1 wt. %, or no added liquid fraction from refining crude oil or reforming any such fraction in a slurry feedstock stream or to a slurry fed gasifier.

In a slurry gasifier feedstock, the content of liquids, or the content of water, present in the feedstock composition is desirably not more than 50 wt. %, or not more than 35 wt. %, or not more than 32 wt. %, or not more than 31 wt. %, or not more than 30 wt. %, based on the weight of the feedstock composition. Desirably, in each case, the content of liquids or water in the feedstock composition for a slurry fed gasifier is desirably at least 10 wt. %, or at least 15 wt. %, or at least 20 wt. %, or at least 25 wt. %, or at least 27 wt. %, or at least 30 wt. %, based on the weight of the feedstock composition. The liquids present in the slurry gasifier feedstock desirably contain at least 95 wt. % water, or at least 96 wt. % water, or at least 97 wt. % water, or at least 98 wt. % water, or at least 99 wt. % water, based on the weight of all liquids fed to the gasifier. In another embodiment, other than chemical additives that are chemically synthesized and contain oxygen or sulfur or nitrogen atoms, the liquid content of the feedstock composition is at least 96 wt. % water, or at least 97 wt. % water, or at least 98 wt. % water, or at least 99 wt. % water, based on the weight of all liquids fed to the gasifier.

In one embodiment or in combination with any of the mentioned embodiments, at least a portion of the fuel feedstock to the gasifier is a liquid at 25° C. and 1 atmosphere, such as organic feedstocks, petroleum oils or fractions from refining or distilling crude oil, hydrocarbons, oxygenated hydrocarbons, or synthetic chemical compounds. These liquid feedstocks can be from any fraction from petroleum distillation or refining, or any chemical synthesized at a chemical manufacturing facility, provided they are liquid. These liquids are a carbon fuel source for gasifying into syngas. In one embodiment or in combination with any of the mentioned embodiments, there is now also provided a combination of densified textile aggregates and a hydrocarbon liquid fuel or oxygenated hydrocarbon liquid fuel that are liquid at 25° C. and 1 atmosphere. Depending on the nature of the liquid fuel feedstock, the densified textile aggregate may be insoluble, partially soluble, or soluble in the liquid fuel feedstock.

In an embodiment, the water present in the feedstock stream is not wastewater, or in other words, the water fed to the solids to make the feedstock stream is not wastewater. Desirably, the water employed has not been industrially discharged from any process for synthesizing chemicals, or it not municipal wastewater. The water is desirably fresh water, or potable water.

In one embodiment or in combination with any mentioned embodiments, the feedstock stream comprises at least ground coal and densified textile aggregates. Desirably, the feedstock stream also comprises water. The amount of water in the feedstock stream can range from 0 wt. % up to 50 wt. %, or from 10 wt. % to 40 wt. %, or from 20 wt. % to 35 wt. %. The feedstock stream is desirably a slurry containing water.

In addition to solid fossil fuel and densified textile aggregate, other additives can be added to and contained in the feedstock composition, such as viscosity modifiers and pH modifiers. The total quantity of additives can range from 0.01 wt. % to 5 wt. %, or from 0.05 wt. % to 5 wt. %, or from 0.05 to 3 wt. %, or from 0.5 to 2.5 wt. %, based on the weight of the feedstock composition. The quantity of any individual additive can also be within these stated ranges.

The viscosity modifiers (which includes surfactants) can improve the solids concentration in a slurry gasifier feedstock. Examples of viscosity modifiers include:

(i) alkyl-substituted amine-based surfactant such as alkyl-substituted aminobutyric acid, alkyl-substituted polyethoxylated amide, and alkyl-substituted polyethoxylated quaternary ammonium salt; and (ii) sulfates such as salts of organic sulfonic acids including ammonium, calcium and sodium sulfonates, particularly those with lignin and sulfo-alkylated lignites;

(iii) phosphate salts;

(iv)polyoxyalkylene anionic or nonionic surfactants.

More specific examples of alkyl-substituted aminobutyric acid surfactants include N-coco-beta-aminobutyric acid, N-tallow-beta-aminobutyric acid, N-lauryl-beta-aminobutyric acid, and N-oleyl-beta-aminobutyric acid. N-coco-beta-aminobutyric acid.

More specific examples of alkyl-substituted polyethoxylated amide surfactant include polyoxyethylene oleamide, polyoxyethylene tallowamide, polyoxyethylene laurylamide, and polyoxyethylene cocoamide, with 5-50 polyoxyethylene moieties being present.

More specific examples of the alkyl-substituted polyethoxylated quaternary ammonium salt surfactant include methylbis (2-hydroxyethyl) cocoammonium chloride, methylpolyoxyethylene cocoammonium chloride, methylbis (2-hydroxyethyl) oleylammonium chloride, methylpolyoxyethylene oleylammonium chloride, methylbis (2-hydroxyethyl) octadecylammonium chloride, and methylpolyoxyethylene octadecylammonium chloride.

More specific examples of sulfonates include sulfonated formaldehyde condensates, naphthalene sulfonate formaldehyde condensates, benzene sulfonate-phenol-formaldehyde condensates, and lingosulfonates.

More specific examples of phosphate salts include trisodium phosphate, potassium phosphate, ammonium phosphate, sodium tripolyphosphate or potassium tripolyphosphate.

Examples of polyoxyalkylene anionic or nonionic surfactants have 1 or more repeating units derived from ethylene oxide or propylene oxide, or 1-200 oxyalkylene units.

Desirably, the surfactant is an anionic surfactant, such as salts of an organic sulfonic acid. Examples are calcium, sodium and ammonium salts of organic sulfonic acids such as 2,6-dihydroxy naphthalene sulfonic acid, lignite sulfonic acid, and ammonium lignosulfonate.

Examples of pH modifiers include aqueous alkali metal and alkaline earth hydroxides such as sodium hydroxide, and ammonium compounds such as 20-50 wt. % aqueous ammonium hydroxide solutions. The aqueous ammonium hydroxide solution can be added directly to the feedstock composition prior to entry into the gasifier, such as in the coal grinding equipment or any downstream vessels containing the slurry.

In one embodiment or in combination with any of the mentioned embodiments, the atomic ratio of total oxygen to carbon entering the gasification zone can be a value in the range of 0.70 to less than 2, or from 0.9 to 1.9, or from 0.9 to 1.8, or from 0.9 to 1.5, or from 0.9 to 1.4, or from 0.9 to 1.2, or from 1 to 1.9, or from 1 to 1.8, or from 1 to 1.5, or from 1 to 1.2, or from 1.05 to 1.9, or from 1.05 to 1.8, or from 1.05 to 1.5, or from 1.05 to 1.2. The atomic ratio of free oxygen to carbon entering the gasification zone can also be within these same values. The weight ratio of both total oxygen and free oxygen to carbon in pounds entering the gasification zone can also each be within these stated values.

In one embodiment or in combination with any of the mentioned embodiments, the total carbon content in the feedstock composition is at least 40 wt. %, or at least 45 wt. %, or at least 50 wt. %, or at least 55 wt. %, or at least 60 wt. %, or at least 65 wt. %, and desirably at least 70 wt. %, or at least 75 wt. %, or at least 80 wt. %, or at least 85 wt. %, or at least 90 wt. %, each based on the total solids content.

In one embodiment or in combination with any of the mentioned embodiments, the gasifier feedstock composition is desirably injected along with an oxidizer into a refractory-lined combustion chamber (gasification zone) of the synthesis gas generating gasifier. The feedstock stream (desirably a slurry) and oxidizer are desirably sprayed through an injector into a gasification zone. The gasification zone can be under significant pressure, typically about 500 psig or more, or 600 psig or more, or 800 psig or more, or 1000 psig or more. For an entrained flow gasifier, the velocity or flow rate of the feedstock and oxidizer streams ejected from the injector nozzle into the gasification zone (or combustion chamber) will exceed the rate of flame propagation to avoid backflash.

In one embodiment or in combination with any of the mentioned embodiments, advantageously only one feedstock composition is charged to the gasifier or gasification zone, or in other words, all sources of carbon fuel are fed to the gasifier in only one stream.

In one embodiment or in combination with any of the mentioned embodiments, only one feedstock stream is necessary or employed to produce a syngas or product stream that is a raw material to synthesize a chemical compound.

In another embodiment, a chemical is made from a first syngas sourced from a first gasifier fed with a first feedstock composition containing a solid fossil fuel is not combined with a second syngas stream sourced from any other gasifier fed with second fossil fuel feedstock composition where the solid fossil fuel content between the first and second feedstock compositions differ by more than 20%, or more than 10%, or more than 5%, based on the weight of the all solids fed to the gasifiers. For example, a first syngas stream generated from a first feedstock composition containing 90 wt. % coal would not be combined with a syngas stream generated from a different gasifier fed with a feedstock composition containing 70 wt. % coal or no coal, but could be combined with one containing 72 wt. % coal or more.

In another embodiment, a first syngas sourced from a first gasifier fed with a first feedstock composition containing a first fixed carbon content is not combined with a second syngas stream sourced from any other gasifier fed with a second feedstock containing a second fixed carbon content, where the difference between the first and second fixed carbon contents is more than 20%, or more than 10%, or more than 5% of each other, based on the weight of the all solids fed to the gasifiers. For example, a first syngas stream generated from a first feedstock composition containing 70 wt. % fixed carbon based on the weight of the solids would not be combined with a syngas stream generated from a different gasifier fed with a feedstock composition containing 30 wt. % fixed carbon, but could be combined with one containing 56 wt. % fixed carbon if the limit of 20% is selected.

Prior to entry into the gasifier, the feedstock composition may be subjected to a variety of other optional processes. For example, a slurry can flow through a thickener in which excess water is eliminated from the slurry to obtain the final desired solids concentration of the slurry entering into the gasifier vessel. The feedstock composition may be preheated to prior to entry into the gasifier. In this embodiment, a slurry feedstock composition is heated to a temperature below the boiling point of water at the operating pressure existing in reaction zone. The preheater, when employed, reduces the heat load on the gasifier and improves the efficiency of utilization of both fuel and oxygen.

In one embodiment or in combination with any of the mentioned embodiments, at least 80 wt. % of all of the water required for the generation of synthesis gas in reaction zone is supplied in liquid phase. When petroleum coke is employed as fuel for the gas generator, part of the water, e.g., from 1 to about 90 percent by weight based on the weight of water, may be vaporized in the slurry feed preheater or combined with the oxidizing stream as vaporized water.

The oxidizer is desirably an oxidizing gas that can include air, and desirably is a gas enriched in oxygen at quantities greater than that found in air. The reaction of oxygen and solid fossil fuel is exothermic. Desirably, the oxidant gas contains at least 25 mole % oxygen, or at least 35 mole %, or at least 40 mole %, or at least 50 mol %, or at least 70 mole %, or at least 85 mole %, or at least 90 mole %, or at least 95 mole %, or at least 97 mole %, or at least 98 mole % oxygen, or at least 99 mole %, or at least 99.5 mole % based on all moles in the oxidant gas stream injected into the reaction (combustion) zone of the gasifier. In another embodiment, the combined concentration of oxygen in all gases supplied to the gasification zone is also in the above stated amount. The particular amount of oxygen as supplied to the reaction zone is desirably sufficient to obtain near or maximum yields of carbon monoxide and hydrogen obtained from the gasification reaction relative to the components in the feedstock composition, considering the amount relative to the feedstock composition, and the amount of feedstock charged, the process conditions, and the gasifier design.

In one embodiment or in combination with any of the mentioned embodiments, steam is not supplied to the gasification zone in a slurry fed gasifier. The amount of water in a slurry fed system is typically more than sufficient a co-reactant and heat sink to regulate the gasification temperature. The addition of steam in a slurry fed gasifier will generally unduly withdraw heat from the reaction zone and reduce its efficiency. In one embodiment or in combination with any of the mentioned embodiments, steam is fed to the gasification zone in any type of dry fed gasifier, such as an entrainment flow gasifier, a fluidized bed gasifier, or a fixed or moving bed gasifier. The addition of steam in dry fed gasifiers case is desirable to provide the raw material needed for the production of carbon monoxide.

Other reducible oxygen-containing gases may be supplied to the reaction zone, for example, carbon dioxide, or simply air. In one embodiment or in combination with any of the mentioned embodiments, no gas stream enriched in carbon dioxide or nitrogen (e.g. greater than the molar quantity found in air, or greater than 2 mole %, or greater than 5 mole %, or greater than 10 mole %, or greater than 40 mole %) is charged into a slurry fed gasifier. Many of these gases serve as carrier gases to propel a dry feed to a gasification zone. Therefore, in another embodiment, one or more of these gases are charged to the gasification zone as a carrier gas for the dry feed of solid fossil fuel and densified textile aggregate. Due to the pressure within the gasification zone, these carrier gases are compressed to provide the motive force for introduction into the gasification zone. The expenditure of energy and equipment for compressing carrier gases to the feedstock composition is avoided is a slurry feed. Accordingly, in yet another embodiment, the feedstock composition containing at least densified textile aggregates and solid fossil fuel flowing to the gasifier, or this feedstock composition as introduced to an injector or charge pipe, or this feedstock composition as introduced into the gasification zone, or a combination of all the above, does not contain gases compressed in equipment for gas compression. Alternatively, or in addition, other than the oxygen rich stream described above, no gas compressed in equipment for gas compression is fed to the gasification zone or even to the gasifier. It is noteworthy that high pressure charge pumps that process the slurry feed for introduction into the gasification zone are not considered gas compressing equipment.

In one embodiment or in combination with any of the mentioned embodiments, no gas stream containing more than 0.03 mole %, or more than 0.02 mole %, or more than 0.01 mole % carbon dioxide is charged to the gasifier or gasification zone. In another embodiment, no gas stream containing more than 77 mole %, or more than 70 mole %, or more than 50 mole %, or more than 30 mole %, or more than 10 mole %, or more than 5 mole %, or more than 3 mole % nitrogen is charged to the gasifier or gasification zone. In another embodiment, a gas stream containing more than 77 mole %, or more than 80 mole % nitrogen is charged to the gasifier or gasification zone. In another embodiment, steam is charged into the gasification zone or to the gasifier. In yet another embodiment, a gaseous hydrogen stream (e.g. one containing more than 0.1 mole % hydrogen, or more than 0.5 mole %, or more than 1 mole %, or more than 5 mole %) is not charged to the gasifier or to the gasification zone. In another embodiment, a stream of methane gas (e.g. one containing more than 0.1 mole % methane, or more than 0.5 mole %, or more than 1 mole %, or more than 5 mole % methane) is not charged to the gasifier or to the gasification zone. In another embodiment, the only gaseous stream introduced to the gasification zone is an oxygen rich gas stream as described above.

In one embodiment or in combination with any of the mentioned embodiments, the gasifier can be fed with two or more separate streams to the gasification zone. For example, one feedstock composition can contain natural gas (methane) in a concentration of at least 50 mole % and a second feedstock composition can contain densified textile aggregate as a dry feed or as a slurry or dispersion in fuel liquids other than water or in liquids containing water or containing more than 50 wt. % water based on the weight of the water. In a natural gas fed gasifier, the amount of methane fed to the gasifier is at least 50 mole %, or at least 70 mole % or at least 80 mole % or at least 90 mole % based on the moles of all gases fed to the gasifier, or based on the moles of all feedstock fuel and reactants fed to the gasifier, or even based on the moles of all fuel fed to the gasifier. Suitable liquids as fuel include those mentioned above that are liquid at 25° C. and 1 atm.

The gasification process desirably employed is a partial oxidation gasification reaction. To enhance the production of hydrogen and carbon monoxide, the oxidation process involves partial, rather than complete, oxidization of the fossil fuel and densified textile aggregates and therefore is desirably operated in an oxygen-lean environment, relative to the amount needed to completely oxidize 100% of the carbon and hydrogen bonds. This is in contrast to a combustion reaction which would employ a large stoichiometric excess of oxygen over that needed to make carbon monoxide, leading to the production primarily of carbon dioxide and water. In the particle oxidation gasification process, the total oxygen requirements for the gasifier is desirably at least 5%, or at least 10%, or at least 15%, or at least 20%, in excess of the amount theoretically required to convert the carbon content of the solid fuel and densified textile aggregates to carbon monoxide. In general, satisfactory operation may be obtained with a total oxygen supply of 10 to 80 percent in excess of the theoretical requirements for carbon monoxide production. An example of a suitable amount of oxygen per pound of carbon is in the range of 0.4 to about 3.0-pound free oxygen per pound of carbon, or from 0.6 to 2.5, or from 0.9 to 2.5, or from 1 to 2.5, or from 1.1 to 2.5, or from 1.2 to 2.5 pounds of free oxygen per pound of carbon.

Mixing of the feedstock composition and the oxidant is desirably accomplished entirely within the reaction zone by introducing the separate streams of feedstock and oxidant so that they impinge upon each other within the reaction zone. Desirably, the oxidant stream is introduced into the reaction zone of the gasifier at high velocity both exceed the rate of flame propagation and to improve mixing with the feedstock composition. The oxidant is desirably injected into the gasification zone in the range of 25 to 500 feet per second, or 50 to 400 ft/s, or 100 to 400 ft/s. These values would be the velocity of the gaseous oxidizing stream at the injector-gasification zone interface, or the injector tip velocity.

Figures 3, 4:
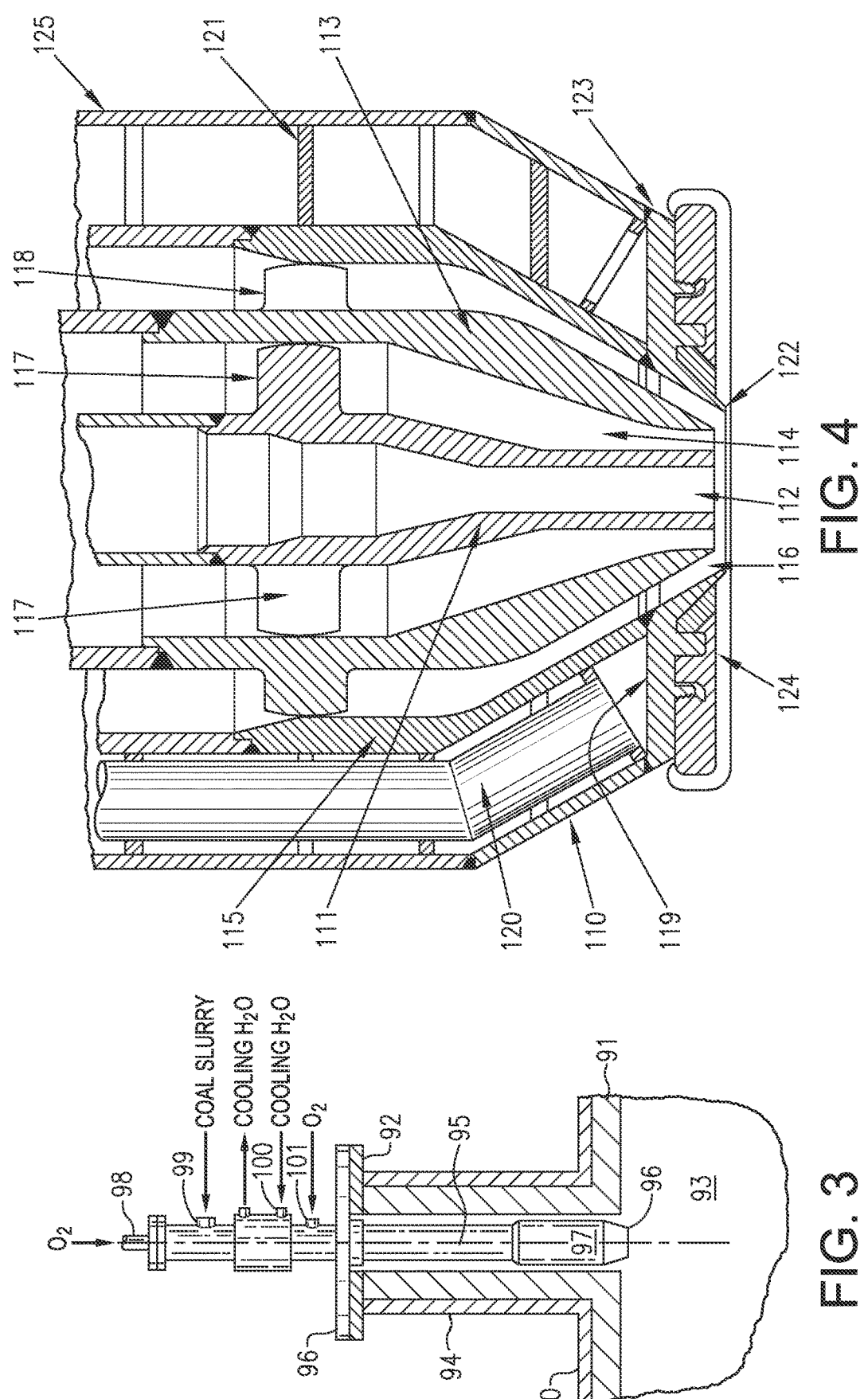
FIG. 3 is a cross section view of a gasifier injector.
FIG. 4 is a more detailed view of the nozzle section of a gasifier injector.

One method for increasing the velocity of the oxidant feed to the gasification zone is by reducing the diameter of the oxidant annulus near the tip of the injector or injector. Near the tip of the injector the annular passage converges inwardly in the shape of a hollow cone as shown in FIGS. 3 and 4. The oxidizing gas is thereby accelerated and discharged from the injector as a high velocity conical stream having an apex angle in the desirably range of about 30° to 45°. The streams from the injector converge at a point located about 0-6 inches beyond the injector face. The high velocity stream of oxidizing gas hits the relatively low velocity feedstock stream, atomizing it and forming a fine mist comprising minute particles of water and particulate solid fossil fuel highly dispersed in the oxidizing gas. The particles of solid carboniferous matter impinge against one another and are fragmented further.

The velocity of the fuel feedstock is determined by the desired throughput of syngas generation. Suitable examples of feedstock velocity introduced into gasification zone prior to contact with the oxidizing agent is in the range of 5 to 50 feet per second.

The feedstock composition and the oxidant can optionally be preheated to a temperature above about 200° C., or at least 300° C., or at least 400° C. Advantageously the gasification process does not require preheating the feedstock composition to efficiently gasify the fuel, and a preheat treatment step would result in lowering the energy efficiency of the process. Desirably, the feedstock composition, and optionally the oxidant, are not preheated prior to their introduction into the gasifier. A preheat treatment step would be contacting the feedstock composition or oxidant with equipment that raises the temperature of the feedstock composition sufficiently such that the temperature of the feedstock composition or oxidant stream is above 200° C., or above 190° C., or above 170° C., or above 150° C., or above 130° C., or above 110° C., or above 100° C., or above 98° C., or above 90° C., or above 80° C., or above 70° C., or above 60° C., immediately prior to introduction into an injector on the gasifier. For example, while coal can be dried with hot air above 200° C., this step would not be considered a preheat of the feedstock composition if the feedstock composition is below 200° C. upon its introduction into the injector.

In another embodiment, no thermal energy (other than incidental heat from processing equipment such as mills, grinders or pumps) is applied to the feedstock composition containing both densified textile aggregates and the solid fossil fuel, or to the oxidant stream, at any point prior to its introduction into the injector, or gasifier, or gasification zone (other than the temperature increase experienced in an injector) that would increase the temperature of the stream by more than 180° C., or more than 170° C., or more than 160° C., or more than 150° C., or more than 140° C., or more than 130° C., or more than 120° C., or more than 110° C., or more than 100° C., or more than 90° C., or more than 80°

C., or more than 70° C., or more than 60° C., or more than 50° C., or more than 40° C., or more than 30° C.

The process employs a gasification process, which is distinct from a incineration process that generates primarily carbon dioxide and water, or a pyrolysis process which is a thermal process that degrades a fuel source in the absence of air or oxygen and generates primarily a liquid, or plasma processes in that gasification does not employ a plasma arc.

In one embodiment, the type of gasification technology employed is a partial oxidation entrained flow gasifier that generates syngas. This technology is distinct from fixed bed (alternatively called moving bed) gasifiers and from fluidized bed gasifiers. In fixed bed (or moving bed gasifiers), the feedstock stream moves in a countercurrent flow with the oxidant gas, and the oxidant gas typically employed is air. The feedstock stream falls into the gasification chamber, accumulates, and forms a bed of feedstock. Air (or alternatively oxygen) flows from the bottom of the gasifier up through the bed of feedstock material continuously while fresh feedstock continuously falls down from the top by gravity to refresh the bed as it is being combusted. The combustion temperatures are typically below the fusion temperature of the ash and are non-slagging. Whether the fixed bed operated in countercurrent flow or in some instances in co-current flow, the fixed bed reaction process generates high amount of tars, oils, and methane produced by pyrolysis of the feedstock in the bed, thereby both contaminating the syngas produced and the gasifier. The contaminated syngas requires significant effort and cost to remove tarry residues that would condense once the syngas is cooled, and because of this, such syngas streams are generally not used to make chemicals and are instead used in direct heating applications, or as liquid fuels. Downdraft fixed or moving bed gasifiers produce less or no tar. Fixed or moving bed gasifiers already equipped or built to be equipped with tar removal processes are suitable to accept a feed of the densified textile aggregate.

In a fluidized bed, the feedstock material in the gasification zone is fluidized by action of the oxidant flowing through the bed at a high enough velocity to fluidize the particles in the bed. In a fluidized bed, the homogeneous reaction temperatures and low reaction temperatures in the gasification zone also promotes the production of high amounts of unreacted feedstock material and low carbon conversion, and operating temperatures in the fluidized bed are typically between 800-1000° C. Further, in a fluidized bed, it is important to operate below slagging conditions to maintain the fluidization of the feedstock particles which would otherwise stick to the slag and agglomerate. By employing an entrained flow gasification, these deficiencies present with fixed (or moving bed) and fluidized bed gasifiers that are typically used to process waste materials is overcome.

In one embodiment or in combination with any of the mentioned embodiments, the feedstock stream is introduced at the top ⅛ section of the gasifier, desirably at the top 1/12 of the gasifier height defined by the gasifier shell (not including the injector height protruding from the top of the shell or pipes protruding from the bottom of the shell). The feedstock composition is desirably not introduced into a side wall of the gasifier. In another embodiment, the feedstock composition is not a tangential feed injector.

In another embodiment, oxidant is introduced at the top ⅛ section of the gasifier, desirably at the top 1/12 of the gasifier height defined by the gasifier shell. The oxidant is desirably not introduced into the side wall of the gasifier or bottom of the flow gasifier. In another embodiment, both the feedstock composition and oxidant are introduced at the top ⅛ section of the gasifier, desirably at the top 1/12 of the gasifier height defined by the gasifier shell. Desirably, the oxidant and feedstock composition are fed co-currently to ensure good mixing. In this regard, a co-current feed means that the axis of the feedstock and oxidant streams are substantially parallel (e.g. not more than a 25° deviation, or not more than a 20°, or not more than a 15°, or not more than a 10°, or not more than a 8°, or not more than a 6°, or not more than a 4°, or not more than a 2°, or not more than a 1° deviation from each other) and in the same direction.

The feedstock and oxidant streams are desirably introduced into the gasification zone through one or more injector nozzles. Desirably, the gasifier is equipped with at least one of the injector nozzles in which through that injector nozzle both a feedstock stream and an oxidant stream are introduced into the gasification zone.

While the feedstock stream can be a dry feed or a slurry feed, the feedstock stream is desirably a slurry.

The syngas produced in the gasification process is desirably used at least in part for making chemicals. Many synthetic processes for making chemicals are at high pressure, and to avoid energy input into pressurizing the syngas stream, desirably the gasifier is also run at high pressure, particularly when the syngas stream is directly or indirectly in gaseous communication with a vessel in which a chemical is synthesized. Dry feeds to a gasifier operating at high pressure are specially treated to ensure that the feed can be effectively blown and injected into the high-pressure gasification zone. Some techniques include entraining a flow of nitrogen at high pressure and velocity, which tends to dilute the syngas stream and reduce the concentration of desirably components such as carbon monoxide and hydrogen. Other carrier or motive gases include carbon monoxide, but like nitrogen, these gases are compressed before feeding into or compressed with the solid fossil fuels, adding to the energy requirements and capital cost of feed lock hoppers and/or compressing equipment. To deal with these issues, many dry feed gasifiers will operate at lower pressures, which for the mere production of electricity is sufficient, but is undesirable for gasifiers producing a syngas stream for making chemicals. With a slurry feed, a motive gas is not necessary and can readily be fed to a high-pressure gasifier that produces syngas as high pressure, which is desirable for making chemicals. In one embodiment or in combination with any of the mentioned embodiments, the feedstock stream is not processed through a lock hopper prior to entering an injector or entering the gasification zone. In another embodiment, the feedstock composition containing size reduced textiles and solid fossil fuel is not pressurized in a lock hopper prior to feeding to the injector or gasification zone.

Desirably, the gasifier is non-catalytic, meaning that gasifier does not contain a catalyst bed, and desirably the gasification process is non-catalytic, meaning that a catalyst is not introduced into the gasification zone as a discrete unbound catalyst (as opposed to captive metals in the size reduced textiles or solid fossil fuel that can incidentally have catalytic activity). The gasification process in the reaction zone is desirably conducted in the absence of added catalysts and contains no catalyst bed. The gasification process is also desirably a slagging gasification process; that is, operated under slagging conditions (well above the fusion temperature of ash) such that a molten slag is formed in the gasification zone and runs along and down the refractory walls.

In another embodiment, the gasifier is not designed to contain a pyrolysis zone. Desirably, the gasifier is not designed to contain a combustion zone. Most preferably, the gasifier is designed to not contain, or does not contain, either a combustion zone or a pyrolysis zone. The pyrolysis zone incompletely consumes the fuel source leading to potentially high amounts of ash, char, and tarry products. A combustion zone, while absent in tars, produces high amounts of CO2 and lower amounts of the more desirably carbon monoxide and hydrogen. Desirably, the gasifier is a single stage reactor, meaning that there is only one zone for conversion of the carbon in the feedstock to syngas within the gasifier shell.

The gasification zone is void or empty space defined by walls in which oxidation reactions occur and allow gases to form within the space. Desirably, gasification zone does not have a bath of molten material or molten material that accumulates at the bottom of the gasification zone to form a bath. The gasification zone is desirably not enclosed on the bottom but rather is in gaseous communication with other zones below the gasification zone. Slag, while molten, does not accumulate at the bottom of the gasification zone but rather runs down the sides of the refractory and into a zone below the gasification zone, such as a quench zone to solidify the slag.

The flow of hot raw syngas in the gasifier is desirably vertically downward, or a down-flow gasifier. Desirably, the flow of syngas generated in the gasifier is downward from the highest point of injecting the feedstock composition, desirably from the point of all feedstock stream locations. In another embodiment, the location for withdrawing the syngas stream from the gasifier is lower that at least one location for introducing the feedstock stream, desirably lower than all locations for introducing a feedstock stream.

The gasifier can contain refractory lining in the gasification zone. While a steam generating membrane or jacket between the gasifier wall and the surfaces facing the gasification zone can be employed, desirably the gasifier does not contain a membrane wall, or a steam generating membrane, or a steam jacket in the gasification zone or between inner surfaces facing the gasification zone and the gasifier shell walls as this removes heat from the gasification zone. Desirably, the gasification zone is lined with refractory, and optionally there is no air or steam or water jacket between the refractory lining the gasification zone (or optionally in any reaction zone such as combustion or pyrolysis) and the outer shell of the gasifier.

The gasification process is desirably a continuous process meaning that the gasifier operates in a continuous mode. The inclusion of densified textile aggregates into the feedstock composition can be intermittent or continuous provided that a continuous feed of fossil fuel is fed to the gasifier since the gasification process in the gasifier is in a continuous mode. By a continuous mode for gasifier operation is meant that the gasification process is continuous for at least 1 month, or at least 6 months, or at least 1 year. Desirably, the inclusion of densified textile aggregates in the feedstock composition is continuous for at least 1 day, or at least 3 days, or at least 14 days, or at least 1 month, or at least 6 months, or at least 1 year. A process is deemed continuous despite shut-downs due to maintenance or repair.

The feedstock can be fed into the gasification zone through one or more injectors. In one embodiment or in combination with any of the mentioned embodiments, the gasifier contains only one injector. In another embodiment, the gasifier contains only one location for introducing feedstock. Typically, the injector nozzle serving the gasification chamber is configured to have the feedstock stream concentrically surround the oxidizer gas stream along the axial core of the nozzle. Optionally, the oxidizer gas stream can also surround the feedstock stream annulus as a larger, substantially concentric annulus. Radially surrounding an outer wall of the outer oxidizer gas channel can be an annular cooling water jacket terminated with a substantially flat end-face heat sink aligned in a plane substantially perpendicular to the nozzle discharge axis. Cool water is conducted from outside the combustion chamber into direct contact with the backside of the heat sink end-face for conductive heat extraction.

The reaction between the hydrocarbon and oxygen should take place entirely outside the injector proper to prevent localized concentration of combustible mixtures at or near the surfaces of the injector elements.

In one embodiment or in combination with any of the mentioned embodiments, the gasification zone, and optionally all reaction zones in the gasifier are operated at a temperature in the range of at least 1000° C., or at least 1100° C., or at least 1200° C., or at least 1250° C., or at least 1300° C., and up to about 2500° C., or up to 2000° C., or up to 1800° C., or up to 1600° C., each of which are well above the fusion temperature of ash, and are desirably operated to form a molten flow of slag in the reaction zone. In one embodiment or in combination with any of the mentioned embodiments, the reaction temperature is desirably autogenous. Advantageously, the gasifier operating in steady state mode is at an autogenous temperature and does not require application of external energy sources to heat the gasification zone. In a fixed bed, moving bed, or fluidized bed gasifier, the gasification zone is generally below 1000° C., or not above 950° C., or not higher than 800° C.

In one embodiment or in combination with any of the mentioned embodiments, the gasifier does not contain a zone within the gasifier shell to dry feedstock such as the coal, pet-coke, or densified textile aggregates prior to gasification. The increase in temperature within the injector is not considered a zone for drying.

Desirably, the gasification zone is not under negative pressure during operations, but rather is under positive pressure during operation. The gasification zone is desirably not equipped with any aspirator or other device to create a negative pressure under steady state operation.

The gasifier can be operated at a pressure within the gasification zone (or combustion chamber) of at least 200 psig (1.38 MPa), or at least 300 psig (2.06 MPa), or at least 350 psig (2.41 MPa), and desirably at least 400 psig (2.76 MPa), or at least 420 psig (2.89 MPa), or at least 450 psig (3.10 MPa), or at least 475 psig (3.27 MPa), or at least 500 psig (3.44 MPa), or at least 550 psig (3.79 MPa), or at least 600 psig (4.13 MPa), or at least 650 psig (4.48 MPa), or at least 700 psig (4.82 MPa), or at least 750 psig (5.17 MPa), or at least 800 psig (5.51 MPa), or at least 900 psig (6.2 MPa), or at least 1000 psig (6.89 MPa), or at least 1100 psig (7.58 MPa), or at least 1200 psig (8.2 MPa). The particular operating pressure on the high end is regulated with a variety of considerations, including operating efficiency, the operating pressures needed in chemical synthesis gasifiers particularly with integrated plants, and process chemistry. Suitable operating pressures in the gasification zone on the high end need not exceed 1300 psig (8.96 MPa), or need not exceed 1250 psig (8.61 MPa), or need not exceed 1200 psig (8.27 MPa), or need not exceed 1150 psig (7.92 MPa), or need not exceed 1100 psig (7.58 MPa), or need not exceed 1050 psig (7.23 MPa), or need not exceed 1000 psig (6.89 MPa), or need not exceed 900 psig (6.2 MPa), or need not exceed 800 psig (5.51 MPa), or need not exceed 750 psig (5.17 MPa). Examples of suitable desirably ranges include 400 to 1000, or 425 to 900, or 450 to 900, or 475 to 900, or 500 to 900, or 550 to 900, or 600 to 900, or 650 to 900, or 400 to 800, or 425 to 800, or 450 to 800, or 475 to 800, or 500 to 800, or 550 to 800, or 600 to 800, or 650 to 800, or 400 to 750, or 425 to 750, or 450 to 750, or 475 to 750, or 500 to 750, or 550 to 750, each in psig.

Desirably, the average residence time of gases in the gasifier reactor are very short to increase throughput. Since the gasifier is operated at high temperature and pressure, substantially complete conversion of the feedstock to gases can occur in a very short time frame. The average residence time of the gases in the gasifier can be as short as less than 30 seconds, or not more than 25 seconds, or not more than 20 seconds, or not more than 15 seconds, or not more than 10 seconds, or not more than 7 seconds. Desirably, the average residence time of gases in all zones designed for conversion of feedstock material to gases is also quite short, e.g. less than 25 seconds, or not more than 15 seconds, or not more than 10 seconds, or not more than 7 seconds, or not more than 4 seconds. In these time frames, at least 85 wt. %, or at least or more than 90 wt. %, or at least 92 wt. %, or at least 94 wt. % of the solids in the feedstock can be converted to gases (substances which remain as a gas if the gas stream were cooled to 25° C. and 1 atm) and liquid (substances which are in liquid state if the gas stream is cooled to 25° C. and 1 atm such as water), or more than 93 wt. %, or more than 95 wt. %, or more than 96 wt. %, or more than 97 wt. %, or more than 98 wt. %, or more than 99 wt. %, or more than 99.5 wt. %.

A portion of ash and/or char in the gasifier can be entrained in the hot raw syngas stream leaving the gasification reaction zone. Ash particles in the raw syngas stream within the gasifier are particles which have not reached the melting temperature of the mineral matter in the solid fuel. Slag is substantially molten ash or molten ash which has solidified into glassy particles and remains within the gasifier. Slag is molten until quenched and then form beads of fused mineral matter. Char are porous particles that are devolatilized and partially combusted (incompletely converted) fuel particles. The particulate matter gathered in the bottom part of the gasifier, or the quench zone, are predominately slag (e.g. above 80 wt. % slag) and the remainder is char and ash. Desirably, only trace amounts of tar or no tar is present in the gasifier, or in the quench zone, or in the gasification zone, or present in the hot raw syngas within the gasifier, or present in the raw syngas discharged from the gasifier (which can be determined by the amount of tar condensing from the syngas stream when cooled to a temperature below 50° C.). Trace amounts are less than 0.1 wt. % (or less than 0.05 wt. % or less than 0.01 wt. %) of solids present in the gasifier, or less than 0.05 volume %, or not more than 0.01 vol %, or not more than 0.005 vol %, or not more than 0.001 volume %, or not more than 0.0005 vol %, or not more than 0.0001 vol % in the raw syngas stream discharged from the gasifier.

In another embodiment, the process does not increase the amount of tar to a substantial extent relative to the same process except replacing the densified textile aggregates with the same amount and type of solid fossil fuel used in the feedstock composition containing the densified textile aggregate.

The quantity of tar generated in the process with the mixed feedstock containing the densified textile aggregate is less than 10% higher, or less than 5% higher, or less than 3% higher, or less than 2% higher, or not higher at all, than the amount of tar generated with the same feedstock replacing the densified textile aggregates with the same solid fossil fuel under the same conditions.

To avoid fouling downstream equipment from the gasifier (scrubbers, CO/H2 shift reactors, acid gas removal, chemical synthesis), and the piping in-between, the syngas stream should have low or no tar content. The syngas stream as discharged from the gasifier desirably contains no or less than 4 wt. %, or less than 3 wt. %, or not more than 2 wt. %, or not more than 1 wt. %, or not more than 0.5 wt. %, or not more than 0.2 wt. %, or not more than 0.1 wt. %, or not more than 0.08 wt. %, or not more than 0.05 wt. %, or not more than 0.02 wt. %, or not more than 0.01 wt. %, or nor more than 0.005 wt. % tar, based on the weight of all condensable solids in the syngas stream. For purposes of measurement, condensable solids are those compounds and elements that condense at a temperature of 15° C./1 atm.

In another embodiment, the tar present, if at all, in the syngas stream discharged from the gasifier is less than 10 g/m3 of the syngas discharged, or not more than 9 g/m3, or not more than 8 g/m3, or not more than 7 g/m3, or not more than 6 g/m3, or not more than 5 g/m3, or not more than 4 g/m3, or not more than 3 g/m3, or not more than 2 g/m3, and desirably not more than 1 g/m3, or not more than 0.8 g/m3, or not more than 0.75 g/m3, or not more than 0.7 g/m3, or not more than 0.6 g/m3, or not more than 0.55 g/m3, or not more than 0.45 g/m3, or not more than 0.4 g/m3, or not more than 0.3 g/m3, or not more than 0.2 g/m3, or not more than 0.1 g/m3, or not more than 0.05 g/m3, or not more than 0.01 g/m3, or not more than 0.005 g/m3, or not more than 0.001 g/m3, or not more than 0.0005 g/m3, in each case Normal (15° C./1 atm). For purposes of measurement, the tars are those tars that would condense at a temperature of 15° C./1 atm, and includes primary, secondary and tertiary tars, and are aromatic organic compounds and other than ash, char, soot, or dust. Examples of tar products include naphthalenes, cresols, xylenols, anthracenes, phenanthrenes, phenols, benzene, toluene, pyridine, catechols, biphenyls, benzofurans, benzaldehydes, acenaphthylenes, fluorenes, naphthofurans, benzanthracenes, pyrenes, acephenanthrylenes, benzopyrenes, and other high molecular weight aromatic polynuclear compounds. The tar content can be determined by GC-MSD.

In another embodiment, the tar yield of the gasifier (combination of tar in syngas and tar in reactor bottoms and in or on the ash, char, and slag) is not more than 4 wt. %, or not more than 3 wt. %, or not more than 2.5 wt. %, or not more than 2.0 wt. %, or not more than 1.8 wt. %, or not more than 1.5 wt. %, or not more than 1.25 wt. %, or not more than 1 wt. %, or not more than 0.9 wt. %, or not more than 0.8 wt. %, or not more than 0.7 wt. %, or not more than 0.5 wt. %, or not more than 0.3 wt. %, or not more than 0.2 wt. %, or not more than 0.1 wt. %, or not more than 0.05 wt. %, or not more than 0.01 wt. %, or not more than 0.005 wt. %, or not more than 0.001 wt. %, or not more than 0.0005 wt. %, or not more than 0.0001 wt. %, based on the weight of solids in the feedstock composition fed to the gasification zone.

The amount of char (or incompletely converted carbon in the feedstock) generated by conversion of the carbon sources in the feedstock composition is not more than 15 wt. %, or not more than 12 wt. %, or not more than 10 wt. %, or not more than 8 wt. %, or not more than 5 wt. %, or not more than 4.5 wt. %, or not more than 4 wt. %, or not more than 3.5 wt. %, or not more than 3 wt. %, or not more than 2.8 wt. %, or not more than 2.5 wt. %, or not more than 2.3 wt. %, or not more than 4.5 wt. %, or not more than 4.5 wt. %, or not more than 4.5 wt. %.

In the process, char can be recycled back to the feedstock composition to the gasifier containing the densified textile aggregate. In another embodiment, the efficiencies and features can be obtained without recycling char back to the gasification zone.

The total amount of char (or incompletely converted carbon in the feedstock) and slag (if any) generated in the gasifier or by the process is desirably not more than 20 wt. %, or not more than 17 wt. %, or not more than 15 wt. %, or not more than 13 wt. %, or not more than 10 wt. %, or not more than 9 wt. %, or not more than 8.9 wt. %, or not more than 8.5 wt. %, or not more than 8.3 wt. %, or not more than 8 wt. %, or not more than 7.9 wt. %, or not more than 7.5 wt. %, or not more than 7.3 wt. %, or not more than 7 wt. %, or not more than 6.9 wt. %, or not more than 6.5 wt. %, or not more than 6.3 wt. %, or not more than 6 wt. %, or not more than 5.9 wt. %, or not more than 5.5 wt. %, in each case based on the weight of the solids in the feedstock composition. In another embodiment, the same values apply with respect to the total amount of ash, slag, and char generated in the gasifier or by the process, based on the weight of the solids in the feedstock composition. In another embodiment, the same values apply with respect to the total amount of ash, slag, char and tar generated in the gasifier or by the process, based on the weight of the solids in the feedstock composition.

The raw syngas stream flows from the gasification zone to a quench zone at the bottom of the gasifier where the slag and raw syngas stream are cooled, generally to a temperature below 550° C., or below 500° C., or below 450° C. The quench zone contains water in a liquid state. The hot syngas from the gasification zone may be cooled by directly contacting the syngas stream with liquid water. The syngas stream can be bubbled through the pool of liquid water, or merely contact the surface of the water pool. In addition, the hot syngas stream may be cooled in a water jacketed chamber having a height that above the top surface of the water pool to allow the hot syngas to both contact the water pool and be cooled in the water jacketed chamber. Molten slag is solidified by the quench water and most of the ash, slag and char are transferred to the water in the quench tank. The partially cooled gas stream, having passed through the water in the quench zone, may be then discharged from the gasifier as a raw syngas stream and passed through a water scrubbing operation to remove any remaining entrained particulate matter.

The pressure in the quench zone is substantially the same as the pressure in the gasification zone located above the water level in the gasifier, and a portion of the quench water and solids at the bottom of the quench tank is removed by way of a lock hopper system. A stream of quench water carrying fine particles exits the gasifier quench zone in response to a liquid level controller and can be directed to a settler. The solids and water from the lock hopper may then flow into a water sump or settler where optionally the coarse particulate solids may be removed by screens or filter thereby producing a dispersion of fine particulate solids.

The raw gas stream discharged from the gasification vessel includes such gasses as hydrogen, carbon monoxide, carbon dioxide and can include other gases such as methane, hydrogen sulfide and nitrogen depending on the fuel source and reaction conditions. Carbon dioxide in the raw syngas stream discharged from the gasification vessel is desirably present in an amount of less than 20 mole %, or less than 18 mole %, or less than 15 mole %, or less than 13 mole %, or not more than 11 mole %, based on all moles of gases in the stream. Some nitrogen and argon can be present in the raw syngas stream depending upon the purity of the fuel and oxygen supplied to the process.

In one embodiment or in combination with any of the mentioned embodiments, the raw syngas stream (the stream discharged from the gasifier and before any further treatment by way of scrubbing, shift, or acid gas removal) can have the following composition in mole % on a dry basis and based on the moles of all gases (elements or compounds in gaseous state at 25° C. and 1 atm) in the raw syngas stream:

a. $H_2$: 15 to 60, or 18 to 50, or 18 to 45, or 18 to 40, or 23 to 40, or 25 to 40, or 23 to 38, or 29 to 40, or 31 to 40 b. CO: 20 to 75, or 20 to 65, or 30 to 70, or 35 to 68, or 40 to 68, or 40 to 60, or 35 to 55, or 40 to 52 c. CO2: 1.0 to 30, or 2 to 25, or 2 to 21, or 10 to 25, or 10 to 20 d. H2O: 2.0 to 40.0, or 5 to 35, or 5 to 30, or 10 to 30 e. CH4: 0.0 to 30, or 0.01 to 15, or 0.01 to 10, or 0.01 to 8, or 0.01 to 7, or 0.01 to 5, or 0.01 to 3, or 0.1 to 1.5, or 0.1 to 1 f. H2S: 0.01 to 2.0, or 0.05 to 1.5, or 0.1 to 1, or 0.1 to 0.5 g. COS: 0.05 to 1.0, or 0.05 to 0.7, or 0.05 to 0.3 h. Total sulfur: 0.015 to 3.0, or 0.02 to 2, or 0.05 to 1.5, or 0.1 to 1 i. N2: 0.0 to 5, or 0.005 to 3, or 0.01 to 2, or 0.005 to 1, or 0.005 to 0.5, or 0.005 to 0.3

The gas components can be determined by FID-GC and TCD-GC or any other method recognized for analyzing the components of a gas stream.

The molar hydrogen/carbon monoxide ratio is desirably at least 0.65, or at least 0.68, or at least 0.7, or at least 0.73, or at least 0.75, or at least 0.78, or at least 0.8, or at least 0.85, or at least 0.88, or at least 0.9, or at least 0.93, or at least 0.95, or at least 0.98, or at least 1.

The total amount of hydrogen and carbon monoxide relative to the total amount of syngas discharged from the gasifier on a dry basis is high, on the order of greater than 70 mole %, or at least 73 mole %, or at least 75 mole %, or at least 77 mole %, or at least 79 mole %, or at least 80 mole %, based on the syngas discharged.

In another embodiment, the dry syngas production expressed as gas volume discharged from the gasifier per kg of solid fuel (e.g. densified textile aggregates and coal) charged to all locations on the gasifier is at least 1.7, or at least 1.75, or at least 1.8, or at least 1.85, or at least 1.87, or at least 1.9, or at least 1.95, or at least 1.97, or at least 2.0, in each case as N m3 gas/kg solids fed.

The carbon conversion efficiency in one pass is good and can be calculated according to the following formula:

$$= \frac{\text{total carbon in feed} - \text{total carbon in char and tar}}{\text{total carbon in feed}} \times 100$$

The carbon conversion efficiency in the process in one pass can be at least 70%, or at least 73%, or at least 75%, or at least 77%, or at least 80%, or at least 82%, or at least 85%, or at least 88%, or at least 90%, or at least 93%.

In another embodiment, the raw syngas stream contains particulate solids in an amount of greater than 0 wt. % up to 30 wt. %, or greater than 0 wt. % up to 10 wt. %, or greater than 0 wt. % up to 5 wt. %, or greater than 0 wt. % up to 1 wt. %, or greater than 0 wt. % up to 0.5 wt. %, or greater than 0 wt. % up to 0.3 wt. %, or greater than 0 wt. % up to 0.2 wt. %, or greater than 0 wt. % up to 0.1 wt. %, or greater than 0 wt. % up to 0.05 wt. %, each based on the weight of solids in the feedstock composition. The amount of particulate solids in this case is determined by cooling the syngas stream to a temperature of below 200° C., such as would occur in a scrubbing operation.

The cold gas efficiency of the process using the densified textile aggregates/solid fossil fuel as a percent can be calculated as:

$$= \frac{\text{Produced gas (mole)} \times HHV(MJ \text{ per mole})}{\text{Feedstock (kg)} \times HHV(MJ \text{ per kg})} \times 100$$

The cold gas efficiency is at least 60%, or at least 65%, or at least 66%, or at least 67%, or at least 68%, or at least 69%, or desirably at least 70%, or at least 71%, or at least 72%, or at least 73%, or at least 74%, or at least 75%, or at least 76%, or at least 77%, or at least 78%, or at least 79%.

In one embodiment or in combination with any of the mentioned embodiments, hydrogen and carbon monoxide from the raw syngas stream discharged from the gasifier or from a scrubbed or purified syngas stream are not recycled or recirculated back to a gasification zone in a gasifier. Desirably, carbon dioxide from the raw syngas stream discharged from the gasifier or from a scrubbed or purified syngas stream is not recycled or recirculated back to a gasification zone in a gasifier. Desirably, no portion of the syngas stream discharged from the gasifier or from a scrubbed or purified syngas stream is recycled or recirculated back to a gasification zone in a gasifier. In another embodiment, no portion of the syngas discharged from the gasifier is used to heat the gasifier. Desirably, no portion of the syngas made in the gasifier is burned to dry the solid fossil fuel.

The feedstock stream is gasified with the oxidizer such as oxygen desirably in an entrained flow reaction zone under conditions sufficient to generate a molten slag and ash. The molten slag and ash are separated from the syngas and quench cooled and solidified. In a partial oxidation reactor, the coal/size reduced textiles/water mixture is injected with oxygen and the coal/rubber will react with oxygen to generate a variety of gases, including carbon monoxide and hydrogen (syngas). The molten slag and unreacted carbon/size reduced textiles accumulate into a pool of water in the quench zone at the bottom part of the gasifier to cool and solidify these residues.

In one embodiment or in combination with any of the mentioned embodiments, the slag is discharged from the gasifier as a solid. Slag is cooled and solidified within the gasifier in a quench zone within the shell of the gasifier, and is discharged from the gasifier shell as a solid. The same applies to ash and char. These solids discharged from the gasifier are accumulated into a lock hopper which can then be emptied. The lock hopper is generally isolated from the gasifier and the quench zone within the gasifier.

The process can be practiced on an industrial scale and on a scale sufficient to provide syngas as a raw material to make chemicals on an industrial scale. At least 300 tons/day, or at least 500 t/d, or at least 750 t/d, or at least 850 t/d, or at least 1000 t/d, or at least 1250 t/d, and desirably at least 1500 t/d, or at least 1750 t/d, or even at least 2000 t/d of solids can be fed to the gasifier. The gasifier is desirably not designed to be mobile and is fixed to and above the ground, and desirably stationary during operations.

The syngas compositional variability produced by gasifying the feedstock containing the solid fossil fuel and densified textile aggregates is quite low over time. In one embodiment or in combination with any of the mentioned embodiments, the compositional variability of the syngas stream is low during a time period when the feedstock composition contains the solid fossil fuel and the densified textile aggregates. The compositional variability of the syngas stream can be determined by taking at least 6 measurements of the concentration of the relevant gaseous compound in moles in equal time sub-periods across the entire time that the feedstock solids content is consistent and contain densified textile aggregates, such entire time not to exceed 12 days. The mean concentration of the gaseous compound is determined over the 6 measurements. The absolute value of the difference between the number farthest away from the mean and the mean number is determined and divided into the mean number x 100 to obtain a percent compositional variability.

The compositional variability of any one of:
a. CO amount, or
b. $H_2$ amount, or
c. CO2 amount, or
d. CH4 amount, or
e. H2S amount, or
f. COS amount, or
g. H2+CO amount, or its molar ratio in sequence (e.g. H2: CO ratio), or
h. H2+CO+CO2 amount, or its molar ratio in sequence, or
i. H2+CO+CH4 amount, or its molar ratio in sequence, or
j. H2+CO+CO2+CH4 amount, or its molar ratio in sequence, or
k. H2S+COS amount, or its molar ratio in sequence, or
l. $H2+CO+CO_2+CH_4+H_2S+COS$,
can be not more than 5%, or not more than 4%, or not more than 3%, or not more than 2%, or not more than 1%, or not more than 0.5%, or not more than 0.25% during the shorter of a 12-day period or the time that densified textile aggregates are present in the feedstock composition.

In another embodiment, variability of the syngas stream generated by all feedstock sources containing fuel (liquid, gas, or solid) at least one of which contains densified textile aggregates ("textile case") is compared to a benchmark variability of the syngas stream generated from the same feedstocks without the densified textile aggregates and the densified textile aggregate amount is replaced by a corresponding amount of the same fuel ("base case") and processed under the same conditions to obtain a switching variability, or in other words, the syngas variability generated by switching between the two feedstock compositions. The syngas variation of the textile case can be less than, or no different than, or if higher can be similar to the syngas variation of the base case. The time periods to determine variations is set by the shorter of a 12-day period or the time that densified textile aggregates are present in the feedstock composition, and that time period is the same time period used for taking measurements in the solid fossil fuels only case. The measurements for the base case are taken within 1 month before feeding a feedstock containing densified textile aggregates to the gasifier or after the expiration of feeding a feedstock containing densified textile aggregates to the gasifier. The variations in syngas composition made by each of the streams is measured according to the procedures states above. The syngas variability from the textile case is less than, or the same as, or not more than 15%, or not more than 10%, or not more than 5%, or not more than 4%, or not more than 3%, or not more than 2%, or not more than 1%, or not more than 0.5%, or not more than 0.25% of the syngas variability of the base case. This can be calculated as:

$$\% \ SV = \frac{V_t - V_b}{V_b} \times 100$$

where % SV is percent syngas switching variability on one or more measured ingredients in the syngas composition; and $V_t$ is the syngas compositional variability using feedstock(s) containing densified textile aggregates and a second source of fuel together in one stream or in separate feedstock streams; and $V_b$ is the syngas compositional variability using the base case streams (same type and amount of fuel feedstock without the densified textile aggregates), where the solids concentration is the same in both cases, the fuel is the same in both cases other than the presence of absence of the densified textile aggregate, and the feedstocks are gasified under the same conditions, other than temperature fluctuations which may autogeneously differ as a result of having densified textile aggregates in the feedstock, and the variabilities are with respect to any one or more of the syngas compounds identified above. In the event that the % SV is negative, then the syngas textile case variability is less than the syngas base case.

In another embodiment, the ratio of carbon monoxide/hydrogen generated from one or more streams that contain densified textile aggregates and other fuel sources (textile case) is similar to the carbon monoxide/hydrogen ratio generated from the same stream(s) replacing the densified textile aggregates content with the same fuel (base case). The carbon monoxide/hydrogen ratio between the textile case and the base case can be within 10%, or within 8%, or within 6%, or within 5%, or within 4%, or within 3%, or within 2%, or within 1.5%, or within 1%, or within 0.5% of each other. The percentage similarity can be calculated by taking the absolute value of the differences in $CO/H_2$ ratios between the textile case and the base case and dividing that number into the CO/H2 ratio of the base case×100.

In another embodiment, the amount of CO2 generated from a textile case is similar to the amount of carbon dioxide generated from a base case. The process can be conducted such that the amount of $CO_2$ generated from textile case is no more than 25%, or no more than 20%, or no more than 15%, or no more than 13%, or no more than 10%, or no more than 8%, or no more than 7%, or no more than 6%, or no more than 5%, or no more than 4%, or no more than 3%, or no more than 2%, or no more than 1%, or no more than 0.75%, or no more than 0.5%, or nor more than 0.25%, or no more than 0.15%, or no more than 0.1% greater than the amount of carbon dioxide generated from a base case. The percentage similarity can be calculated by subtracting the amount of $CO_2$ generated in a syngas stream using the textile case from the amount of $CO_2$ generated in a syngas stream using the base case, and dividing that number by the CO2 generated in a syngas stream using the base case×100.

In another embodiment, there is provided a continuous process for feeding a gasifier with a continuous feedstock composition containing solid fossil fuel and intermittently feeding a feedstock composition containing densified textile aggregates and solid fossil fuel, while maintaining a negative, zero, or minimal syngas compositional switching variability over time frames that includes feedstocks with and without the densified textile aggregates using syngas produced using feedstocks without the densified textile aggregates as the benchmark. For example, switching frequency between feedstocks without the densified textile aggregates (base case) and the identical feedstocks except replacing a portion of the fuel with the densified textile aggregates (textile case) can be at least 52×/yr, or at least 48×/yr, or at least 36×/yr, or at least 24×/yr, or at least 12×/yr, or at least 6×/yr, or at least 4×/yr, or at least 2×/yr, or at least 1×/yr, or at least 1×/2 yr, and up to 3×/2 yr, without incurring a syngas switching variability beyond the percentages express above. One switch is counted as the number of times in a period that the textile case is used.

To illustrate an example of a slurry fed slagging entrained flow process, reference made to FIG. 1. Coal is fed through line 1 into a coal grinding zone 2 wherein it is mixed with a water from stream 3 and ground to the desired particle size. A suitable coal grinding process includes a shearing process. Examples of a suitable apparatus include ball mill, a rod mill, hammer mill, a raymond mill, or an ultrasonic mill; desirably a rod mill. The rod mill is desirably the wet grind type to prepare a slurry. A rod mill contains a number of rods within a cylinder where the rods rotate about a horizontal or near horizontal axis. The coal is ground when it is caught between the rods and cylinder wall by the rolling/rotating action of the rods. The rod mill can be the overflow type, end peripheral discharge, and center peripheral discharge, desirably the overflow type.

The grinder can also be equipped with a classifier to remove particles above the target maximum particle size. An example of a classifier is a vibrating sieve or a weir spiral classifier.

The coal grinder zone (which includes at least the grinding equipment, feed mechanisms to the grinder, and any classifiers) is a convenient location for combining densified textile aggregates particles through line 4 to the coal. The desired amount of coal and densified textile aggregates can be combined onto a weigh belt or separately fed though their dedicated weigh belts that feed the grinding apparatus. The water slurry of ground coal and densified textile aggregates is discharged through line 5 and pumped into a storage/charge tank 6 that is desirably agitated to retain a uniform slurry suspension. Alternatively, or in addition to the grinder 2 location, densified textile aggregates can be added into the charge/storage tank 6 through line 7, particularly when this tank is agitated.

The feedstock composition is discharged from tank 6 directly or indirectly to the gasifier 9 through line 8 into the injector 10 in which the coal/rubber/water slurry is co-injected with an oxygen-rich gas from line 11 into the gasification reaction zone 12 where gasification takes place. The injector 10 may optionally be cooled with a water line 13 feeding a jacket on the injector and discharged through line 14. After start-up and in a steady state, the reaction in the reaction zone 12 takes place spontaneously at an autogenous temperature in the ranges noted above, e.g. 1200° C. to 1600° C. and at a pressure in the ranges note above, e.g. 10-100 atmospheres. The gaseous reaction products of the partial oxidation reaction include carbon monoxide, hydrogen, with lesser amounts of carbon dioxide and hydrogen sulfide. Molten ash, unconverted coal or rubber, and slag may also be present in the reaction zone 12.

Figure 2:
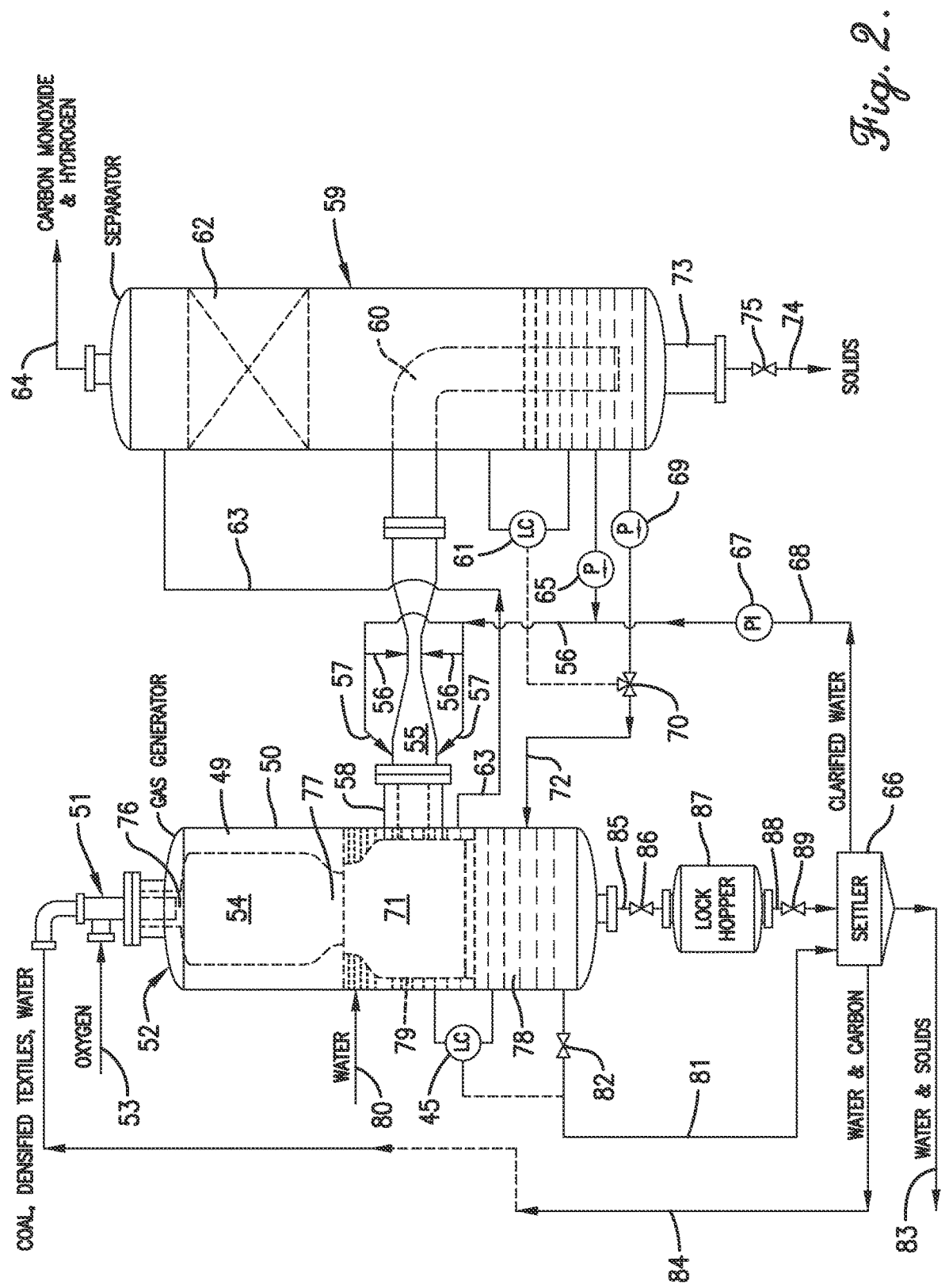
FIG. 2 is another example of a plant design for gasifying a feedstock of densified textile aggregates and solid fossil fuel to produce a syngas stream that is scrubbed.

The gasifier 9 is illustrated in more detail in FIG. 2, also as shown in U.S. Pat. No. 3,544,291, the entire disclosure of which is incorporated herein by reference. The gasifier comprises a cylindrical pressure vessel 50 with a refractory lining 75 defining a cylindrical, compact, unpacked reaction zone 54. The mixture of coal, densified textile aggregates, water and oxygen is injected through an injector axially into the upper end of reaction zone 54 through inlet passageway 76. Products of reaction are discharged axially from the lower end of reaction zone 54 through an outlet passageway 77 into a slag quench chamber 71. The quench chamber 71 and the reaction zone 54 are within the outer shell 50 of the gasifier and are in continuous gaseous and fluid communication with each other during the combustion and reaction in reaction zone 54. A pool of water 78 is maintained in the lower portion of quench chamber 71 and a water jacket 79 is provided in the upper portion of the quench chamber 71 to protect the pressure vessel shell from becoming overheated by hot gases from the gasification zone 54. Unconverted solid fuel and molten slag and ash from the solid fuel is discharged with the product gas stream through outlet 77 into the quench chamber 71 where the larger particles of solid and any molten ash or slag drops into the pool of water. The partially cooled gas is discharged from the quench chamber 71 through line 58, which optionally is also provided with a refractory lining 75.

Turning back to FIG. 1, the hot reaction product gas from reaction zone 12 along with the slag formed on the surfaces of refractory facing the reaction zone 12 are discharged into the quench chamber 15 where they are quickly cooled and solidified below the reaction temperature in zone 12 to form solid slag, ash, and unconverted coal which separates from the hot raw syngas to form a raw syngas stream which is discharged from the gasifier vessel. The process effectuates a separation of ash, slag, and unconverted products from the reaction product gases, and has the advantage over a fixed or moving bed waste gasifier in that within the gasifier vessel, a first step of purification of the gaseous reaction products from the reaction zone 12 has occurred prior to discharging the raw syngas stream from the gasification vessel. At the same time that the slag and vaporized unconverted fossil fuel elements are solidified in the quench water in quench zone 15, and part of the quench water is vaporized producing steam which is useful in subsequent operations, for example, for the water-gas shift reaction of the scrubbed raw syngas stream in which hydrogen is produced by reaction of carbon monoxide with water vapor in the presence of a suitable catalyst such as an iron oxide-chromic oxide catalyst.

The temperature of the raw syngas stream exiting the gasification vessel through line 16 can be within a range of 150° C. to 700° C., or from 175° C. to 500° C. Desirably, the temperature of the raw syngas discharged from the gasifier is not more than 500° C., or less than 400° C., or not more than 390° C., or not more than 375° C., or not more than 350° C., or not more than 325° C., or not more than 310° C., or not more than 300° C., or not more than 295° C., or not more than 280° C., or not more than 270° C. The temperature of the raw syngas exiting the gasification vessel is substantially reduced from the temperature of the reaction product gases within the reaction zone. The temperature reduction between the gasification zone gas temperature (or alternatively all reaction zones if more than one stage is used) and the raw syngas temperature discharged from the gasifier vessel can be at least 300° C., or at least 400° C., or at least 450° C., or at least 500° C., or at least 550° C., or at least 600° C., or at least 650° C., or at least 700° C., or at least 800° C., or at least 900° C., or at least 1000° C., or at least 1050° C., or at least 1100° C.

As shown in FIG. 1, the raw syngas is discharged from the gasifier through line 16 to a suitable scrubber 17 where it is contacted with water from line 18 for the removal of remaining solid particles from the raw syngas stream. Gas scrubber 17 may comprise a venturi scrubber, a plate type scrubber or a packed column, or a combination thereof, in which raw syngas stream is intimately contacted with water to effect the removal of solid particles from the raw syngas stream. The scrubbed raw syngas stream is discharged through line 19 for further use in other processes, such as acid gas (e.g. sulfur compounds) removal processes to make the resulting purified syngas stream suitable for manufacture of chemicals. Suitable process for acid gas removal include the Rectisol™ and Selexol™ acid gas removal processes. Once the sulfur species are removed from the syngas stream, elemental sulfur can be recovered and converted to sulfuric acid and other sulfur products that can be commercialized through processes such as the Claus™ process.

As shown in FIG. 1, the solids-water mixture from gas scrubber 17 is discharged from the scrubber passed through line 20 optionally to line 21 where it is mixed with quench water containing solids drawn from quench zone 15 via line 22 and the mixture passed through pressure reducing valve 23 into settling tank 24. A heat exchanger 25 serves to heat by heat exchange with hot quench water from line 22 the relatively cool make-up and recycle water supplied through line 26 from a suitable source and pumped to lines for quenching and/or scrubbing the product gas from the gas generator.

Solids, including unconverted particulate coal, settle by gravity from the water in settling tank 24 and are drawn off through line 27 as a concentrated slurry of ash, unconverted coal and soot in water. This slurry may be optionally be recycled to grinding zone 2 via line 28. If desired, a portion of the slurry from line 27 may be diverted through line 29 into mix tank 6 to adjust the concentration of solids in the water-coal-rubber slurry feed stream charged to the gasifier. Also, as shown in FIG. 2, water and solids from settler tank 66 may be drawn off in line 83 for processing, while water and ash, unconverted coal and soot may be drawn off the settle tank 66 through line 84 and combined with the feedstock of coal, densified textile aggregates and water.

As shown in FIG. 1, gases released in settler 24 may be discharged through line 30 and recovered as potential fuel gases. Clarified water from settler 24 is withdrawn through line 31 and recirculated to the quench water system through line 32. A portion of the water from line 32, after passing through heat exchanger 25, is supplied to the quench zone 15 through line 33 and a further portion of the water is passed through line 18 to gas scrubber 17. Further, water from the quench zone can be withdrawn through line 22 to settler 24 through a control valve 23. The water level can be controlled through a liquid level controller on the gasifier to maintain a substantially constant water level in quench zone.

Alternatively, or in addition, the quench water through line 33 feeding the quench water zone can supplied from a syngas scrubber downstream from the gasifier as shown in FIG. 2. The quench water stream optionally also fed to the quench zone may be clarified or may contain from about 0.1 weight % soot to about 1.5 weight % soot based on the weight of the quench water stream feeding the gasifier.

If desired, high temperature surfactants can be added to the quench water directly into the quench zone/chamber. Examples of such surfactants include any one of the surfactants mentioned above to stabilize the feedstock composition, such as ammonium lignosulfonate or an equivalent surfactant which is thermally stable at temperatures of about 300° F. to about 600° F. Other surfactants include organic phosphates, sulfonates and amine surfactants. The surfactants are used to establish a stable suspension of soot in the water at the bottom of the quench chamber, where the soot concentration can be at least 1 wt. %, or in the range of about 3.0 weight % to about 15.0 weight %, each based on the weight of the water in the quench chamber. The concentration of active surfactants in the bottom of the quench zone can vary from about 0.01 weight % to about 0.30 weight %.

Also, as illustrated in FIG. 2, an internal water jacket 79 is provided within the pressure vessel shell 50 at the upper portion of the quench zone 71. Water jacket 79 prevents overheating of the pressure vessel shell below the level of refractory 75 surrounding reaction zone 54. Water is introduced into water jacket 79 from line 80 and discharged therefrom through line 81 through valve 82 and can be fed directly or indirectly (through a settler tank 66) to a scrubber 59.

As shown in FIG. 1, periodically slag and other heavy incombustible solids settling to the bottom of quench zone 15 are withdrawn as a water-solids slurry through line 34 and valve 35 into lock hopper 36. Accumulated solid material from lock hopper 36 is discharged through line 37 as controlled by valve 38. In the operation of the lock hopper, valve 35 is opened and valve 38 closed during the filling period in which solid material from quench chamber 15 is transferred to lock hopper 36. Valve 35 is then closed and the lock hopper 36 emptied through line 37 by opening valve 38. From lock hopper 36, solid residue and water are discharged through line 37. The equivalent equipment and lines are shown in FIG. 2 as outlet 85, valves 86 and 88, line 89, and lock hopper 87.

In an alternative embodiment as shown in FIG. 1, fresh water can be charged to the lock hopper 36 to displace the sour water in the lock hopper 36. Cold clean water from line 39 is introduced through valve 40 into the lower part of lock hopper 36. Valve 41 in line 42 is opened to establish communication between line 33 and lock hopper 36. As the cold clean water enters the lower part of lock hopper 36, hot sour water is displaced from the lock hopper and flows through line 42 and line 33 into the quench zone 15 as part of the make-up water for the quench system. After the sour water has been displaced from lock hopper 36 valves 40 and 41 are closed and valve 38 opened to permit discharge of slag and clean water from the lock hopper through line 37.

In an alternate embodiment, as shown in FIG. 1, stripping gas such as carbon dioxide, or gases produced by the gasifier from which acid gases have been removed by chemical treatment, can be introduced into the lower portion of lock hopper 36 through line 43 after the lock hopper has been charged with slag and sour water from the quench zone 15 and valve 35 closed. Stripping gas under pressure is introduced into the lower portion of lock hopper 36 by opening valve 44 in line 43. At the same time, valve 41 in line 42 is opened allowing gas to pass through lines 42 and 33 into the quench zone 15. The stripping gas from line 43 desorbs sour gases, i.e. sulfides, cyanides, and other noxious gases, from the water in lock hopper 36. When the desorbed gases are introduced back into the gasifier, they mix with hot product gases and, after passing through the quench zone are discharged through line 16 to gas scrubber 17 as a part of the product gas stream for further purification and utilization.

An example of the operation of the gasifier and scrubber is illustrated in FIG. 2. The coal/densified textile aggregates feedstock slurry is fed to the gas generator 50 through injector 51 mounted at the top 52 of the gasifier and is fed with oxygen through line 53 and injected into the gasification zone 54 to generate a raw syngas. The raw syngas gases discharged from the gasifier is fed to a contactor 55. Water is injected into contactor 55 from line 56 through injectors 56 and 57. Intimate contact between the raw syngas from line 58 and water from line 56 is effected desirably by way of a venturi, nozzle, or plate orifice. In contactor 55, the syngas stream is accelerated, and water is injected into the accelerated gas stream at the throat of the nozzle, venturi or orifice, from a plurality of injectors 56 and 57.

The resulting mixture of gas and water formed in contactor 55 is directed into scrubber 59 through a dip leg 60 which extends downwardly into the lower portion of scrubber 59. The gas stream from contactor 55 also carries entrained solid particles of unconsumed fuel or ash. A body of water is maintained in the scrubber 59, the level of which may be controlled in any suitable manner, for example by means of a liquid level controller 61, shown diagrammatically. The dip leg 60 discharges the mixture of water and gas below the level of water contained in the scrubber 59. By discharging the mixture of gas and water through the open end of dip leg 60 into intimate contact with water, solid particles from the gas stream are trapped in the water.

Scrubber 59 is suitably in the form of a tower having an optionally packed section 62 above the point of entry of the gas stream from contactor 55. Water from line 63 is introduced into scrubber 59 above the level of the packing material 62. In packed section 62, the gas stream is intimately contacted with water in the presence of suitable packing material, such as ceramic shapes, effecting substantially complete removal of solid particles from the gas stream. Product gas, comprising carbon monoxide and hydrogen and containing water vapor, atmospheric gases, and carbon dioxide, is discharged from the upper end of scrubber 59 through line 64 at a temperature corresponding to the equilibrium vaporization temperature of water at the pressure existing in scrubber 59. Clean syngas from line 64 may be further processed, for example, for the production of higher concentrations of hydrogen by water-gas shift reaction and suitable downstream purification to remove sulfur.

Water from the lower portion of scrubber 59 is passed by pump 65 through line 56 to injectors 56 and 57. Clarified water from settler 66 also may be supplied to line 56 by pump 67 through line 68. Water is withdrawn from scrubber 59 by pump 69 and passed through valve 70 responsive to liquid level control 61 on the scrubber and passed into quench zone 71 via line 72 to control the liquid level in scrubber 59.

Any heavy solid particles removed from the gas stream in the dip leg 60 settling into water slurry are collected the water bath at the bottom of the scrubber 59 and discharged at the bottom leg 73 at periodic intervals through line 74 as controlled by valve 75.

Any suitable scrubber design can be used in the process. Other scrubber designs include a tray type contacting tower wherein the gases are counter currently contacted with water. Water is introduced into the scrubber at a point near the top of the tower.

To illustrate one embodiment of an injector, reference is made to FIG. 3, showing a partial cut-away view of a synthesis gas gasifier at the injector location. The gasifier vessel includes a structural shell 90 and an internal refractory liner 91 (or multiple liners) around an enclosed gasification zone 93. Projecting outwardly from the shell wall is an injector mounting neck 94 for supporting an elongated fuel injection injector assembly 95 within the gasifier vessel. The injector assembly 95 is aligned and positioned so that the face 96 of the injector nozzle 97 is substantially flush with the inner surface of the refractory liner 91. An injector mounting flange 96 secures the injector assembly 95 to a mounting neck flange 97 of the gasifier vessel to prevent the injector assembly 95 from becoming ejected during operation. A feed of oxygen flows into a central inner nozzle through conduit 98. The feedstock stream is fed to the injector assembly through line 99 into an annular space around the central oxidant nozzle. A cooling jacket surrounding the injector assembly 95 above the injector mounting flange 96 is fed with cooling water 100 to prevent the injector assembly from overheating. An optional second feed of oxidant flows through line 101 into an annular space around at least a portion of the outer surface of the shell defining the feedstock annulus.

A more detailed view of the injector is shown in FIG. 4. A sectional view of a portion of the injector assembly 80 toward the injector nozzle tip is illustrated. The injector assembly 80 includes an injector nozzle assembly 125 comprising three concentric nozzle shells and an outer cooling water jacket 110. The inner nozzle shell 111 discharges from an axial bore opening 112 the oxidizer gas that is delivered along upper assembly axis conduit 98 in FIG. 3. Intermediate nozzle shell 113 guides the feedstock stream into the gasification zone 93. As a fluidized solid, this size reduced textile/coal slurry is ejected from the annular space 114 defined by the inner shell wall 111 and the intermediate shell wall 113. The outer, oxidizer gas nozzle shell 115 surrounds the outer nozzle discharge annulus 116. The upper assembly port 101, as shown in FIG. 3, supplies the outer nozzle discharge annulus with an additional stream of oxidizing gas. Centralizing fins 117 and 118 extend laterally from the outer surface of the inner and intermediate nozzle shell walls 111 and 113, respectively to keep their respective shells coaxially centered relative to the longitudinal axis of the injector assembly. It will be understood that the structure of the fins 117 and 118 form discontinuous bands about the inner and intermediate shells and offer small resistance to fluid flow within the respective annular spaces.

The internal nozzle shell 111 and intermediate nozzle shell 113 can both be axially adjustable relative to the outer nozzle shell 115 for the purpose flow capacity variation. As intermediate nozzle 113 is axially displaced from the conically tapered internal surface of outer nozzle 115, the outer discharge annulus 116 is enlarged to permit a greater oxygen gas flow. Similarly, as the outer tapered surface of the internal nozzle 111 is axially drawn toward the internally conical surface of the intermediate nozzle 113, the feedstock slurry discharge area 114 is reduced.

Surrounding the outer nozzle shell 115 is a coolant fluid jacket 110 having an annular end closure 119. A coolant fluid conduit 120 delivers a coolant, such as water, from the upper assembly supply port 100 in FIG. 3 directly to the inside surface of the end closure plate 119. Flow channeling baffles 121 control the path of coolant flow around the outer nozzle shell to assure a substantially uniform heat extraction and to prevent the coolant from channeling and producing localized hot spots. The end closure 119 includes a nozzle lip 122 that defines an exit orifice or discharge opening for the feeding of reaction materials into the injection injector assembly.

The planar end of the cooling jacket 119 includes an annular surface 123 which is disposed facing the combustion chamber. Typically, the annular surface 123 of cooling jacket is composed of cobalt base metal alloy materials. Although cobalt is the preferred material of construction for the nozzle assembly 125, other high temperature melting point alloys, such as molybdenum or tantalum may also be used. The heat shield 124 is formed from a high temperature melting point material such as silicon nitride, silicon carbide, zirconia, molybdenum, tungsten or tantalum.

While this discussion was based on a injector and feed stream arrangement as previously described, it is understood that the injector may consist of only two passages for introducing and injecting the oxidant and feedstock stream, and they may be in any order with the feedstock stream passing through the central axial bore opening while the feedstock is fed through an annulus surrounding at least a portion of the central oxidant conduit, or the order may be reversed as described above In one embodiment or in combination with any of the mentioned embodiments shown in FIG. 3, the size reduced textiles can be introduced at location 100, the main feed belt. The size reduced textiles are metered onto the main feed belt as it moves past with the feed already loaded onto the belt. The size reduced textiles added to the belt using a weigh belt feeder, or other similar device, to measure the mass of the material, and the speed of the belt to determine addition rate. The solid fossil fuel is similarly added to the same belt and would be underneath the size reduced textiles. The combined solid mixture of the solid fossil fuel and size reduced textiles in the proper ratio are then conveyed to surge hoppers and other storage and conveying equipment until it is ultimately fed to the grinding mill. In the grinding mill, the solid fossil fuel, size reduced textiles, water and viscosity modifiers are mixed thoroughly, and the solid fossil fuel is reduced in size to the target grind size distribution, and the mixture becomes a viscous slurry. The size reduced textiles undergo very little size reduction since it is a softer material, but benefits from the extreme mixing in the mill due to its inclusion into the slurry production process. The size reduced textiles have been pre-ground.

In another embodiment, size reduced textiles can be introduced as shown in FIG. 3 location number 110. This is the same process as described in location number 100 above, except that the size reduced textiles are added to the main belt first, before the solid fossil fuel is added. In this manner, solid fossil fuel is on top. Since the size reduced textiles will be pre-ground and may inherently be less dense than the solid fossil fuel, it may be easier for this material to be blown off of the belt in a strong wind. With the more dense solid fossil fuel covering the size reduced textiles, this dusting and loss of material will be greatly reduced.

In another embodiment the invention, the size reduced textiles can be added at location number 120, the grinding mill. The existing equipment, solid fossil fuel, water and viscosity modifiers are already added to the grinding mill to reduce the particle size of the solid fossil fuel and produce a slurry high in solids. The size reduced textiles can be independently conveyed to the entry point of the mill and added directly to the mill in the proper ratio. The mill will then grind the solid fossil fuel, produce the slurry and thoroughly mix in the size reduced textiles in the process. This avoids wind and weather effects on the solid fossil fuel, size reduced textile mixture.

In yet another embodiment, the size reduced textiles can be introduced at location number 130, the slurry storage tank. Since the size reduced textiles are pre-ground to the proper particle size for introduction into the gasifier, it can be added to the slurry storage tank directly after the grinding/slurry operation. Alternatively, it can be added to the tank through a separate screen or the screen used by the slurry to ensure no large particles are passed to the tank. This is the last low-pressure addition point before the slurry is pumped at pressure to the gasifier. This will minimize the amount of material in process that is mixed together. The agitation in the slurry tanks will mix in the size reduced textiles to ensure it is evenly distributed.

The slurry is pumped at high pressure through an injector into the gasifier. Alternatively, to the options above, the size reduced textiles, could be slurried and pumped to the gasifier in a similar way to a second feed injector or even share the slurry injector. This would give ultimate control of the two feed materials and would be desirable on a theoretical basis. However, this method would be extremely expensive to implement in an existing system and even in a new build. Also, the size reduced textiles do not slurry as well as solid fossil fuel (lower slurry solids) and would therefore carry additional unwanted water to the gasifier system.

For gasifiers utilizing small particle feeds (<4 mm), there are several options.

1. The material can be mixed with the coal as it unloads from the coal cars to storage piles or silos. Then subsequently, the mixed material will be processed like the coal or other carbonaceous material in existing equipment per normal operations.

2. The material can be added to the coal as it is fed out of the silo on its way to further processing. This provides some flexibility to add the material only when needed instead of bulk mixing at the onset. Then subsequently, the mixed material will be processed like the coal or other carbonaceous material in existing equipment per normal operations.

3. The material can be added directly to and co-current with the normal feed to the existing size reduction equipment where no expected additional size reduction is expected due to the plastic (non-friable) nature of the material. However, the existing grinding equipment will greatly aide in the mixing of the material with the other constituents such as coal, pet coke or other carbonaceous fuels.

4. The material can be added downstream of existing size reduction equipment and just mixed in with the main stream of slurry or dry feed.

5. The material can be slurried separately and pumped independently to the gasifier injection point as a second gasifier feed or mixed with the initial gasifier feed close coupled to the gasifier to minimize mixing or incompatibility issues with the streams. This would apply to a slurry fed gasifier or a dry feed gasifier that accepts liquid feeds or a natural gas gasifier (PDX) that accepts liquid feeds.

6. For a dry feed gasifier, material could be pneumatically conveyed separately to the gasifier injection point as a second gasifier feed or mixed with the initial gasifier feed close coupled to the gasifier to minimize mixing or incompatibility issues with the streams.

This invention is described for a solid fossil fuel/water slurry gasifier, but would apply directly to a gasifier utilizing petroleum coke, slurry fed gasifier as well as conceptually to a dry coal fed gasifier. In one embodiment of the invention, the size reduced textiles described herein includes consumer plastics for packaging, apparel and durable goods, cellulosic plastics, textiles automotive tires and other polymers and solid wastes with significant chemical/energy content.

In order to fulfill a market need to produce products with an improved environmental footprint, a family of acetyl chemicals, their derivatives and intermediates made from syngas produced from size reduced textiles has been developed. These acetyl chemicals include acetic acid, acetic anhydride and methyl acetate with an intermediate of methanol. Derivatives are many with examples such as solvent esters, cellulose esters certain monomers, polymers and plasticizers.

There is a market need for consumer products in general to contain significant amounts of renewable, recycled, re-used, biodegradable or other materials that will improve carbon emissions, waste disposal and other environmental sustainability issues. Families of acetyl chemicals and their intermediates and derivatives are made from syngas (carbon monoxide and hydrogen) in a multi-step process. The syngas is produced from a gasification process. The problem to be solved is to produce these same acetyl chemicals, intermediates and derivatives from syngas derived from size reduced textiles such as consumer plastics for packaging, textiles, apparel and durable goods, cellulosic plastics, automotive tires, and other polymers and solid wastes with significant chemical/energy content. The acetyl products, intermediates and derivatives can then claim and environmental advantage.

The size reduced textiles are gasified in a gasifier with oxygen and water either alone or as a co-feed with a fossil fuel feed such as coal, petroleum coke, natural gas, oil, and residual oil to produce a syngas comprised primarily of carbon monoxide and hydrogen. In one embodiment, the syngas is reacted in a series of steps starting with methanol, then proceeding through acetic acid, methyl acetate and then acetic anhydride. These processes are the same as the processes used for fossil fuel derived syngas. These acetyl products can then be further combined with other materials to produce many derivative products. Examples include solvent esters such as methyl acetate and butyl acetate, cellulose esters such as cellulose acetate, vinyl acetate monomer, polymers, plasticizers such as triacetin and many others.

Acetic acid and acetic anhydride are key products. They are sold as products and also used to make higher value derivatives such as a family of cellulose esters. In one embodiment or in combination with any of the mentioned embodiments acetic acid and acetic anhydride are produced through a multi-step process that includes methanol and methyl acetate intermediates starting with syngas (primarily a mixture of carbon monoxide and hydrogen). In one embodiment, the syngas is produced from a coal gasifier which is purified and conditioned to produce a clean syngas stream comprised primarily of hydrogen and carbon. The syngas stream and the carbon monoxide stream are reacted in a multi-step process to produce methanol, acetic acid, methyl acetate and acetic anhydride. Textiles can be feed to the gasifier to produce a syngas similar to the gas streams produced in a coal gasifier. Then, this syngas derived from textiles can be used to produce methanol, acetic acid, methyl acetate and acetic anhydride using the very same processes that use syngas derived from coal or other fossil fuels. When textiles are used to produce the syngas then, the acetyl chemicals, their intermediates and derivatives can claim recycle content. In one embodiment or in combination with any of the mentioned embodiments, the organic compound comprises at least one selected from the group consisting acetic acid, methanol, methyl acetate, acetic anhydride, C2-C5 oxygenated compounds, methyl formate, formic acid, formaldehyde, dimethyl ether, MTBE, oxo products, aldehydes, and isobutene. In another embodiment said organic compound comprises at least one selected from the group consisting acetic acid, methanol, methyl acetate, acetate, acetic anhydride, C2-C5 oxygenated compounds, methyl formate, formic acid, formaldehyde, dimethyl ether, MTBE, oxo products, aldehydes, and isobutene. In yet another embodiment, the organic compound comprises at least one selected from the group consisting acetic acid, methanol, methyl acetate, acetate, and acetic anhydride.

In additional embodiments, the textile by-products can be utilized as a feedstock to gasifiers either alone or in combination with traditional feeds by mechanically reducing the size of the material to convert them to a form that is more easily processed by conventional feeding methods.

Once the textiles have been sized reduced, it can be added in multiple locations to optimize cost to implement and mixing efficiency.

Gasifiers that can accept larger particles (up to 4") may not need any size reduction and is more straight-forward.

1. The material can be mixed with the coal as it unloads from the coal cars to storage piles or silos. Then subsequently, the mixed material will be processed like the coal or other carbonaceous material in existing equipment per normal operations.

Figure 6:
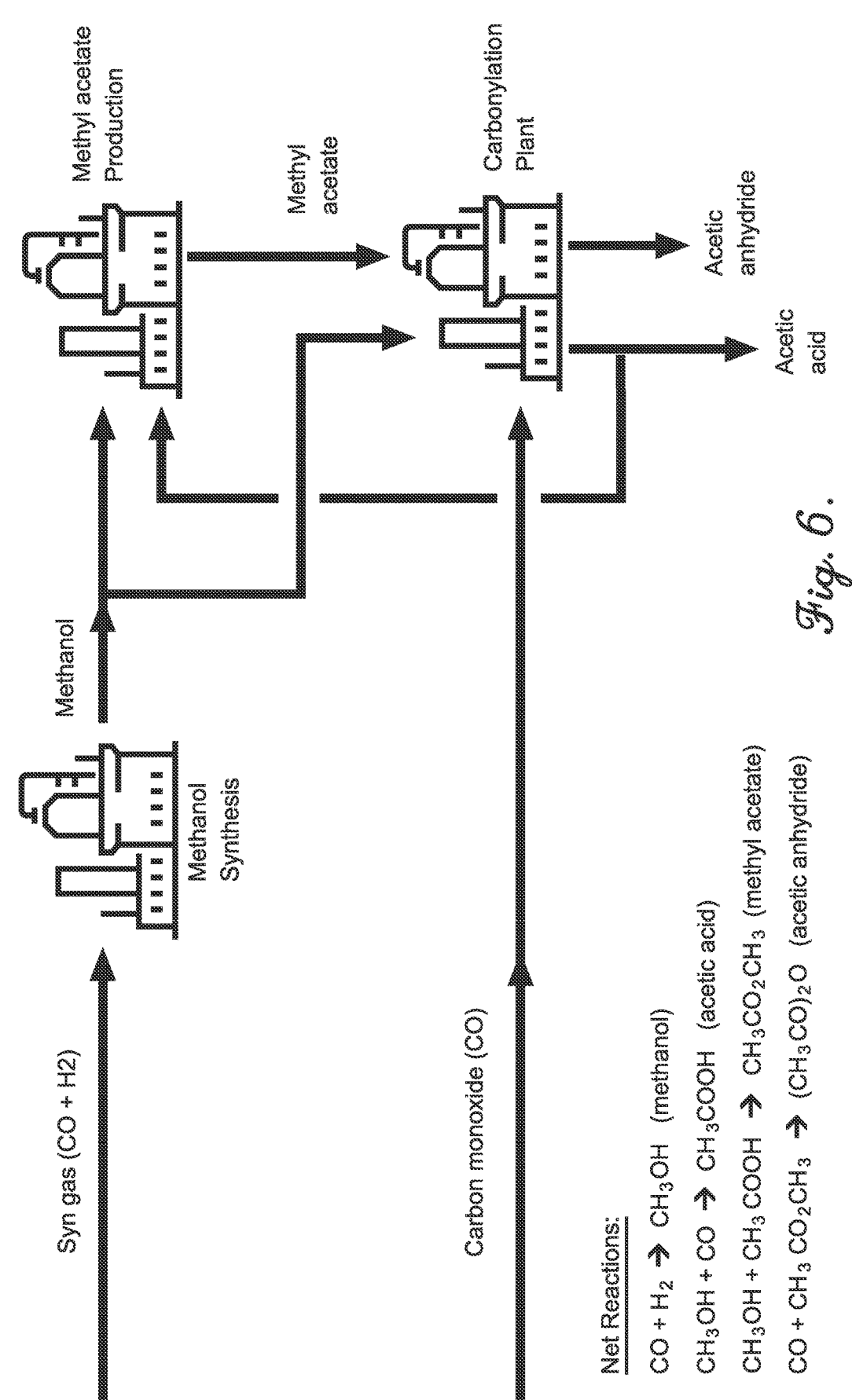
FIG. 6 is a detail view of the some of the organic chemicals that are produce from syngas.

2. The material can be added to the coal as it is fed out of the silo on its way to further processing. This provides some flexibility to add the material only when needed instead of bulk mixing at the onset. Then subsequently, the mixed material will be processed like the coal or other carbonaceous material in existing equipment per normal operations Synthesis gas (syngas) can be used as a feedstock in any chemical process in which one or more of the hydrogen and carbon monoxide in the synthesis gas is converted to a reaction product. In an embodiment of the invention a typical processes are shown in FIG. 6. Any chemical process that can efficiently convert a synthesis gas feedstock into useful chemical product may be used. For example, the chemical process can comprise a process for making methanol, methyl acetate, acetic acid, acetic anhydride, alkyl formates, dimethyl ether, ammonia, methane, hydrogen, Fischer-Topsch products, or a combination thereof.

In one embodiment, synthesis gas is used to produce methanol. Synthesis gas comprised of hydrogen and carbon monoxide in a ratio of approximately 2:1 $H_2$:CO possibly with a small amount of carbon dioxide produced from the gasification of coal or recycled materials is fed to the methanol production plant. It is then contacted with a catalyst to cause the reaction between 2 equivalents of $H_2$ and 1 equivalent of CO to form 1 equivalent of methanol. Concurrently, $CO_2$ is consumed by the reaction of 1 equivalent of $CO_2$ with 3 equivalents of $H_2$ to form 1 equivalent each of methanol and water. The produced methanol can be purified by distillation.

The methanol process can comprise any type of methanol synthesis plant that are well known to persons skilled in the art and many of which are widely practiced on a commercial basis. Most commercial methanol synthesis plants operate in the gas phase at a pressure range of about 25 to about 140 bara using various copper based catalyst systems well known in the art and depending on the technology used. A number of different state-of-the-art technologies are known for synthesizing methanol such as, for example, the ICI (Imperial Chemical Industries) process, the Lurgi process, the Haldor-Topsoe process, and the Mitsubishi process. Liquid phase processes are also well known in the art. Thus, the methanol process according to the present invention may comprise a fixed bed methanol reactor, containing a solid or supported catalyst, or liquid slurry phase methanol reactor, which utilizes a slurried catalyst in which metal or supported catalyst particles are slurried in an unreactive liquid medium such as, for example, mineral oil.

Examples of suitable methanol synthesis catalysts include, but are not limited to, oxides of zinc and chromium; oxides of zinc, copper and chromium; and oxides of zinc, copper, and aluminum; as well as zinc, copper, and aluminum; as well as zinc-copper-chromium-lanthanum oxides.

The synthesis gas stream is typically supplied to a methanol reactor at the pressure of about 25 to about 140 bara, depending upon the process employed. The syngas then reacts over a catalyst to form methanol. The reaction is exothermic; therefore, heat removal is ordinarily required. The raw or impure methanol is then condensed and may be purified to remove impurities such as higher alcohols including ethanol, propanol, and the like or, burned without purification as fuel. The uncondensed vapor phase comprising unreacted syngas feedstock typically is recycled to the methanol process feed.

Methanol produced from synthesis gas can be used to produce acetic acid when methanol is reacted with carbon monoxide. Any method known in the art can be used to produce the acetic acid. In one embodiment, from a synthesis gas mainly consisting of hydrogen and carbon oxides, an acetic acid product consisting of acetic acid, acetic anhydride and/or methyl acetate can be prepared by reactions known in a technically simple reaction sequence and a high conversion degree when the reactions are combined such that in a first step at a pressure of 5-200 bar and a temperature of 150° C. to 400° C., the synthesis gas is converted in the gas phase in a first reactor to methanol (Reaction 1), of which at least a substantial proportion is converted to dimethyl ether (Reaction 2) in the same reactor in the presence of one or more catalysts which together catalyze the reactions and then passing the entire effluent from the first reactor to a second reactor in which methanol and dimethyl ether at a pressure of 1-800 bar and a temperature of 100° C. to 500° C. are carbonylated to the desired product in the presence of one or more catalysts which together catalyze the reactions:

$$CO + 2H_2 \rightarrow CH_3OH \text{ (methanol)} \tag{1}$$

$$2CH_3OH \rightarrow CH_3OCH_3 \text{ (dimethyl ether)} + H_2O \tag{2}$$

and $$CO + H_2O \rightarrow CO_2 \text{ and } H_2 \tag{3}$$

And then passing the entire effluent from the first reactor to a second reactor in which methanol and dimethyl ether at a pressure of 1-800 bar and a temperature of 100 to 500° C. are carbonylated to the desired product in the presence of one or more catalyst which together catalyze the reactions.

$$CH_3OH + CO \rightarrow CH_3COOH \text{ (acetic acid)} \tag{4}$$

$$CH_3OCH_3 \text{ (dimethyl ether)} + CO \rightarrow CH_3COOCH_3 \\ \text{(methyl acetate)} \tag{5}$$

And optionally, $$CH_3OCH_3 + 2CO \rightarrow (CH_3CO)_2O \text{ (acetic anhydride)} \tag{6}$$

And $$CH_3COOCH_3 + CO \rightarrow (CH_3CO)_2O \text{ (acetic anhydride)} \tag{7}$$

And possible even the hydrolysis, $$CH_3COOCH_3 + H_2O \rightarrow CH_3COOH + CH_3OH \tag{8}$$

Or methanolysis, $$CH_3COOCH_3 + CH_3OH \rightarrow CH_3COOH + CH_3COOCH_3 \tag{9}$$

Methanol produced from the synthesis gas can be utilized for the synthesis of methyl acetate. Acetic acid and methanol are contacted with an acid catalyst to produce methyl acetate and water. For example, the contacting can be conducted inside a distillation column. The acetic acid utilized is also derived from synthesis gas as it is produced in the subsequent acetic acid and acetic anhydride production plant. The resulting methyl acetate is removed by distillation out the top of the column and the resulting water is removed from the bottom of the column.

Methyl acetate produced from the synthesis gas derived methanol and acetic acid is fed into the carbonylation plant. It is contacted with CO which was produced by the gasification of coal or recycled materials. Methyl acetate and CO react to form acetic anhydride. This reaction takes place in acetic acid solvent and is catalyzed by a metal catalyst (typically a salt of rhodium or iridium) and lithium iodide (LiI) cocatalysts. Methanol can be co-fed to the reactor; it can be carbonylated to acetic acid via the steps shown above or can contact acetic anhydride and react to form methyl acetate and acetic acid. Methyl acetate formed in the process can ultimately be converted to acetic anhydride or acetic acid. In this way, synthesis gas derived acetic anhydride and acetic acid are produced as co-products. They can be recovered and separated by distillation. This process is described in more detail elsewhere. In the manner described here methanol, methyl acetate, acetic acid, and acetic anhydride are all synthesized entirely from syngas that was derived from the gasification of coal or recycled materials. In the case in which recycled materials are used, the methanol, methyl acetate, acetic acid, and acetic anhydride are comprised of recycled carbon and hydrogen atoms.

The following patent disclose information about the production of chemicals from synthesis gas: U.S. Pat. Nos. 4,525,481; 5,741,440; 6,706,770; 7,253,304; and 7,503,947; all of which are incorporated by reference to the extent they do not contradict the statements herein.

In addition to methanol, dimethyl ether, methyl acetate, acetic acid, and acetic anhydride, it is within the scope of the present invention to produce any chemical that is efficiently obtained from a syngas feedstock such as, for example, alkyl formates, methane, ammonia, dimethyl ether, hydrogen, Fischer-Tropsch products, or a combination of one or more of these chemicals. For example, ammonia and/or hydrogen can be produced. Typical conversions of carbon monoxide to hydrogen and carbon dioxide are greater than 95%. If desired, carbon dioxide can be removed by conventional absorption or adsorption technologies, followed by final purification step. For example, using pressure swing adsorption, the oxygenate content of the hydrogen typically can be reduced to less than 2 ppm by volume. The hydrogen can be sold or used to produce ammonia by the Haber-Bosch process by means known in the art as exemplified by LeBlance et al in "Ammonia", *Kirk-Othmer Encyclopedia of Chemical Technology*, Volume 2, 3$^{rd}$ Edition, 1978, pp. 494-500.

In another embodiment of the invention, Fischer-Tropsch products such as, for example, hydrocarbons and alcohols, can be produced via a Fischer-Tropsch reaction as exemplified in U.S. Pat. Nos. 5,621,155 and 6,682,711. Typically, the Fischer-Tropsch reaction may be effected in a fixed bed, in a slurry bed, or in a fluidized bed reactor. The Fischer-Tropsch reaction conditions may include using a reaction temperature of between 190° C. and 340° C., with the actual reaction temperature being largely determined by the reactor configuration. For example, when a fluidized bed reactor is used, the reaction temperature is preferably between 300° C. and 340° C.; when a fixed bed reactor is used, the reaction temperature is preferably between 200° C. and 250° C.; and when a slurry bed reactor is used, the reaction temperature is preferably between 190° C. and 270° C.

An inlet synthesis gas pressure to the Fischer-Tropsch reactor of between 1 and 50 bar, preferably between 15 and 50 bar, may be used. The syngas may have a H$_2$:CO molar ratio, in the fresh feed, of 1.5:1 to 2.5:1, preferably 1.8:1 to 2.2:1. The synthesis gas typically includes 0.1 wppm of sulfur or less. A gas recycle may optionally be employed to the reaction stage, and the ratio of the gas recycle rate to the fresh synthesis gas feed rate, on a molar basis, may then be between 1:1 and 3:1, preferably between 1.5:1 and 2.5:1. A space velocity, in m$^3$ (kg catalyst)$^{-1}$ hr$^{-1}$, of from 1 to 20, preferably from 8 to 12, may be used in the reaction stage.

In principle, an iron-based, a cobalt-based or an iron/cobalt-based Fischer-Tropsch catalyst can be used in the Fischer-Tropsch reaction stage, although Fischer-Tropsch catalysts operated with high chain growth probabilities (i.e., alpha values of 0.8 or greater, preferably 0.9 or greater, more preferably, 0.925 or greater) are typical. Reaction conditions are generally chosen to minimize methane and ethane formation. This tends to provide product streams which mostly include wax and heavy products, i.e., largely paraffinic C$_{20+}$linear hydrocarbons.

The iron-based Fischer-Tropsch catalyst may include iron and/or iron oxides which have been precipitated or fused. However, iron and/or iron oxides which have been sintered, cemented, or impregnated onto a suitable support can also be used. The iron should be reduced to metallic Fe before the Fischer-Tropsch synthesis. The iron-based catalyst may contain various levels of promoters, the role of which may be to alter one or more of the activity, the stability, and the selectivity of the final catalyst. Typical promoters are those influencing the surface area of the reduced iron ("structural promoters"), and these include oxides or metals of Mn, Ti, Mg, Cr, Ca, Si, Al, or Cu or combinations thereof.

The products from Fischer-Tropsch reactions often include a gaseous reaction product and a liquid reaction product. For example, the gaseous reaction product typically includes hydrocarbons boiling below about 343° C. (e.g., tail gases through middle distillates). The liquid reaction product (the condensate fraction) includes hydrocarbons boiling above about 343° C. (e.g., vacuum gas oil through heavy paraffins) and alcohols of varying chain lengths.

In another example, alkyl formates such as, for example, methyl formate may be produced in the chemical process. There are currently several known processes for the synthesis of alkyl formates from a syngas and alkyl alcohol feedstock such as, for example, as described in U.S. Pat. No. 3,716,619, herein incorporated by reference to the extent it does not contradict the statements herein. Other examples of alkyl formate processes include U.S. Pat. No. 3,816,513, in which carbon monoxide and methanol are reacted in either the liquid or gaseous phase to form methyl formate at elevated pressures and temperatures in the presence of an alkaline catalyst and sufficient hydrogen to permit carbon monoxide to be converted to methanol, and U.S. Pat. No. 4,216,339, in which carbon monoxide is reacted at elevated temperatures and pressures with a current of liquid reaction mixture containing methanol and either alkali metal or alkaline earth metal methoxide catalysts to produce methyl formate. In the broadest embodiment of this invention, however, any effective commercially viable process for the formation of an alkyl formate from a feedstock comprising a corresponding alkyl alcohol and a prepared syngas sufficiently rich in carbon monoxide is within the scope of the invention. The catalyst or catalysts, as well as concentration, contact time, and the like, can vary widely, as is known to those skilled in the art. Examples of suitable catalysts are disclosed in U.S. Pat. No. 4,216,339, but a wide variety of other catalysts known to those skilled in the art also can be used.

EXAMPLES

Example 1

A variety of coal slurries were prepared and tested for stability and viscosity. The reported samples were processed through either an agglomerator, extruder, or a melt press. The resulting material from the agglomerator and extruder were then further ground to a size of <1 mm. Thin material using the Brookfield Rheometer with V80-40 spindle by letting the slurry sit with the spindle submerged for a period of 5, 10, 15, 20, 30, or more minutes, then measuring the viscosity. The viscosity increases with settling and is the slurry is considered to have settled if the initial reading on starting a viscosity measurement is >100,000 cP. Slurries with settling times of less than 10 minutes are considered unstable. The results are reported in Table 1.

TABLE 1

| Substrate ID | Substrate % of solids | Target Solids | Measured Solids | ALS | Avg Viscosity (cP) | 10 min Visc (cP) | 20 min Visc (cP) | Stability |
|---|---|---|---|---|---|---|---|---|
| Control | 0% | 70% | 69.7% | 0.20% | 2749 | 8584 | | Good |
| Densified PET-Cotton Fabric | 2% | 70% | 70.0% | 0.20% | 3394 | 17742 | 50000 | Moderate |
| Melt pressed PET-Cotton Fabric | 2% | 70% | | 0.30% | 2928 | 4808 | 7268 | Good |
| Densified PET-Spandex Fabric | 2% | 70% | 70.0% | 0.20% | 4541 | 21878 | 50000 | Moderate |
| Extruded PET Fabric | 2% | 70% | | 0.10% | 5171 | 10227 | 30343 | Moderate |
| Densified PET Fabric | 5% | 70% | | 0.10% | 4550 | 5216 | 6416 | Good |
| Densified PET-Cotton Fabric | 5% | 70% | | 0.10% | 11705 | 32865 | 35492 | Moderate | on the order of 1 mm or less in width from the melt press was breakable and processed through a rod mill directly as is along with coal. The rod mill successfully crushed the particles to satisfactory size. The PET-Cotton blend may be variable ratios, but is expected to be around 25-35% cotton. The spandex blend may be variable, but is expected to be up to 15% spandex.

Coal was dried and crushed in a Retsch jaw crusher to a nominal size of <2 mm. A predetermined amount of water was added to a 4.5 L metal bucket. A viscosity modifier (ammonium lignosulfonate, ALS) was added to the water and mixed with a spatula until it was distributed evenly. The processed textile material and coal were added to the water and ALS mixture and then the blend was mixed by an overhead mixer. A pH modifier (aqueous ammonia) was added to the slurry to adjust the pH to 8±0.2. After well mixed, the sample was placed in the laboratory rod mill equipped with 5 stainless steel rods at ½"×9", 8 rods at ⅝"×9", 8 rods at ¾"×9", 2 rods at 1"×9", and 1 rod at 1¼"×9". The slurry was milled for 1 hour at approximately 28 rpm (mill outside diameter=11.75 inches). The aqueous ammonia was again used to adjust the pH to 8±0.2 while the slurry was mixed by the overhead mixer. Each batch of slurry was made to be a total of approximately 3000 grams with approximately 70% solids with varying amounts of recycled textile materials.

A 500-550 g sample of coal slurry was transferred to a 600 mL glass beaker to measure the viscosity and stability. The viscosities were measured at room temperature using a Brookfield R/S rheometer with V80-40 vane spindle operating at a shear rate of 1.83/ s. An average of 3 viscosity measurements is reported. The stability was measured by Example 2

A variety of coal slurries were tested with densified and ground textiles following the procedure in example one using a different coal source. The control viscosity with the same ALS loading is much higher than with the coal source in example 1. The important comparison is the control viscosity vs the textile containing viscosities. A good slurry is of similar or lower viscosity to the control having the closest amount of ALS.

The results are reported in Table 2. Each of #1 in Table 2 is the primary slurry. ALS was added to the primary slurry #1 in an amount to make a total amount of ALS reported in Table 2 as #2-4. The ALS was added post rod mill processing in order to decrease the viscosity.

TABLE 2

| Substrate ID | Substrate % of solids | Target Solids | Measured Solids | ALS | Avg Viscosity (cP) |
|---|---|---|---|---|---|
| Control 1 | 0% | 70% | | 0.20% | 51306 |
| Control 2 | 0% | 70% | | 0.38% | 35554 |
| Control 3 | 0% | 70% | | 0.55% | 22745 |
| Densified PET-Cotton Fabric 1 | 2% | 70% | 69.5% | 0.20% | 51450 |
| Densified PET-Cotton Fabric 2 | 2% | 70% | 69.5% | 0.28% | 41144 |
| Densified PET-Cotton Fabric 3 | 2% | 70% | 69.5% | 0.36% | 15980 |
| Densified PET-Cotton Fabric 4 | 2% | 70% | 69.5% | 0.44% | 5668 |
| Densified PET Textiles Fabric 1 | 2% | 70% | | 0.20% | 43569 |

US 12,649,883 B2

79

TABLE 2-continued

| Substrate ID | Substrate % of solids | Target Solids | Measured Solids | ALS | Avg Viscosity (cP) |
|---|---|---|---|---|---|
| Densified PET Textiles Fabric 2 | 2% | 70% | | 0.28% | 41729 |
| Densified PET Textiles Fabric 3 | 2% | 70% | | 0.36% | 16686 |
| Densified PET Textiles Fabric 4 | 2% | 70% | | 0.45% | 6279 |
| Densified Carpet Fiber 1 | 2% | 70% | 70.1% | 0.40% | 75949 |
| Densified Carpet Fiber 2 | 2% | 70% | | 0.71% | 9474 |

What we claim is:

1. A process for the production of syngas comprising:
a. charging an oxidant and a feedstock composition to a gasification zone within a gasifier, said feedstock composition comprising a solid fossil fuel and less than 5 wt. % densified textiles based on the weights of solids in the feedstock composition;
b. gasifying the feedstock composition together with the oxidant in a gasification zone to produce a syngas composition; and
c. discharging at least a portion of the syngas composition from the gasifier; and producing an organic compound from said syngas composition;
wherein the gasifier is an entrained flow gasifier;
wherein the feedstock composition comprises densified textiles, a solid fossil fuel, and water, wherein the densified textiles have a particle size of not more than 2 mm, and the solid fossil fuel in the feedstock composition has a particle size of less than 2 mm, the solids content in the feedstock composition is at least 62 wt. %, the amount of densified textiles present in the feedstock composition is 0.1 wt. % to less than 5 wt. % based on the weight of all solids, and the water is at least 20 wt. % based on the weight of the feedstock composition; and
wherein the feedstock composition is stable as determined by having an initial viscosity of 100,000 cP or less at 5 minutes, or 10 minutes, or 15 minutes, or 20 minutes, or 25 minutes, or even for 30 minutes using a Brookfield R/S Rheometer equipped with V80-40 vane operating at a shear rate of 1.83/s or a Brookfield viscometer with an LV-2 spindle rotating at a rate of 0.5 rpm, measured at ambient conditions; and
wherein the feedstock composition is pumpable as determined by having a viscosity of less than 30,000 cP after mixing to obtain a homogeneous distribution of solids throughout the slurry and using a Brookfield R/S Rheometer equipped with V80-40 vane operating at a shear rate of 1.83/s or a Brookfield viscometer with an LV-2 spindle rotating at a rate of 0.5 rpm, measured at ambient conditions.

2. The process according to claim 1 wherein said organic compound comprises at least one selected from the group consisting acetic acid, methanol, methyl acetate, acetate, acetic anhydride, C2-C5 oxygenated compounds, formaldehyde, dimethyl ether, MTBE, oxo products, aldehydes, and isobutene.

3. The process of claim 1, wherein the feedstock is a slurry.

4. The process of claim 1, wherein the amount of CO2 generated from a stream of densified textiles and solid fossil fuel (mixed stream) is no more than 25% of the amount of carbon dioxide generated from a fossil fuel only stream wherein the amount of densified textiles is replaced with the solid fossil fuel.

5. The process of claim 1, wherein the ratio of carbon monoxide/hydrogen generated from a stream of densified textiles and solid fossil fuel (mixed stream) is within 10 of a carbon monoxide/hydrogen ratio generated from the same stream replacing the densified textiles content with the same solid fossil fuel.

6. The process of claim 1, wherein the fossil fuel comprises coal, pet-coke, or a combination thereof.

7. The process of claim 1, wherein the densified textiles employed comprise at least 70 wt. % truck and/or bus densified textiles, based on the weight of the densified textiles used in the feedstock stream.

8. The process of claim 1, wherein the densified textiles do not receive a thermal treatment prior to their introduction into the gasification zone or their introduction to one or more components of a feedstock stream, wherein the thermal treatment is to subject the densified textiles to a temperature above 150° C.

9. The process of claim 1, wherein the average content of minerals, metals and elements other than carbon, hydrogen, oxygen, nitrogen, and sulfur, in the densified textiles is at least 0.5 wt. %, and in each case does not exceed 10 wt. %.

10. The process of claim 1, wherein the densified textiles in the feedstock composition or as fed to or combined with a solid fuel is 2 mm or smaller.

11. The process of claim 1, wherein the bulk density of the densified textiles without compaction (loose) after final grinding is within 150% of the loose bulk density of the ground fossil fuel after its final grinding.

12. The process of claim 1, wherein the maximum particle size of the ground densified textiles is within 50%, of the maximum particle size of the ground solid fossil fuel.

* * * * *